(12) United States Patent
Champagne et al.

(10) Patent No.: US 12,137,956 B2
(45) Date of Patent: Nov. 12, 2024

(54) ORTHOPEDIC IMPLANTS AND INSTRUMENTS FOR DELIVERING THE SAME

(71) Applicant: Exsomed Corporation, Aliso Viejo, CA (US)

(72) Inventors: Lloyd P. Champagne, Phoenix, AZ (US); Jozef Zoldos, Phoenix, AZ (US); Larry Ehmke, Portland, OR (US); Michael Zwolinski, Willougby, OH (US)

(73) Assignee: ExsoMed Corporation, Aliso Viejo, CA (US)

( * ) Notice: Subject to any disclaimer, the term of this patent is extended or adjusted under 35 U.S.C. 154(b) by 0 days.

(21) Appl. No.: 17/929,425

(22) Filed: Sep. 2, 2022

(65) Prior Publication Data

US 2023/0072157 A1     Mar. 9, 2023

Related U.S. Application Data

(60) Provisional application No. 63/261,028, filed on Sep. 9, 2021.

(51) Int. Cl.
*A61B 17/88*     (2006.01)
*A61B 17/72*     (2006.01)
*A61B 17/56*     (2006.01)

(52) U.S. Cl.
CPC .......... *A61B 17/8897* (2013.01); *A61B 17/72* (2013.01); *A61B 2017/564* (2013.01)

(58) Field of Classification Search
CPC .............. A61B 17/848; A61B 17/1782; A61B 17/1715; A61B 17/1697; A61B 17/86;
(Continued)

(56) References Cited

U.S. PATENT DOCUMENTS 5,259,398 A * 11/1993 Vrespa ................. A61C 8/0025
                                                                411/413
8,236,006 B2    8/2012 Hamada
(Continued)

FOREIGN PATENT DOCUMENTS

WO    2021183647 A1    9/2021

OTHER PUBLICATIONS

International Search Report corresponding to related International Patent Application No. PCT/US2022/075889 mailed Nov. 22, 2022, 7 pages.
(Continued)

*Primary Examiner* — Eduardo C Robert
*Assistant Examiner* — Steven J Cotroneo
(74) *Attorney, Agent, or Firm* — K&L Gates LLP

(57) ABSTRACT

A fracture treatment system can include a pair of implants cross-pinned into the medullary canal of a bone, guided by at least one guide wire with at least two diameters. The system allows for more accurate sizing of the length of implants needed to achieve bicortical purchase for enhanced stability, as well as anti-rotation of the fracture site. The more accurate sizing and placement of the cross-pinned implants additionally allow both ends of the implants to recess beneath or be flush with the outer surface of the bone, which can reduce the risk of infection. The guide wire can allow the implants to be inserted using a cannulated technique for easier surgical procedure and better outcome, with the implants having sufficient wall thickness for the desired length to achieve bicortical purchase while keeping the shaft outer diameter of the implant to be similar to a diameter of the guide wire.

19 Claims, 41 Drawing Sheets

(58) Field of Classification Search
CPC .. A61B 17/17; A61B 17/1717; A61B 17/8897
See application file for complete search history.

(56) References Cited

U.S. PATENT DOCUMENTS

| | | | | |
|---|---|---|---|---|
| 9,763,720 | B2* | 9/2017 | Orsak | A61B 17/1615 |
| 9,993,276 | B2* | 6/2018 | Russell | A61B 17/8695 |
| 11,633,292 | B2* | 4/2023 | Reiley | A61B 17/1659 |
| | | | | 606/279 |
| 2011/0295252 | A1* | 12/2011 | Tipirneni | A61B 17/861 |
| | | | | 606/62 |
| 2013/0090658 | A1* | 4/2013 | Kam | A61B 17/17 |
| | | | | 606/80 |
| 2013/0211468 | A1* | 8/2013 | Huebner | A61B 17/863 |
| | | | | 606/328 |
| 2015/0045839 | A1* | 2/2015 | Dacosta | A61B 17/863 |
| | | | | 606/305 |
| 2015/0265270 | A1* | 9/2015 | Lanois | A61B 17/0401 |
| | | | | 606/232 |
| 2018/0243018 | A1* | 8/2018 | Lintula | A61B 17/8897 |
| 2018/0368893 | A1 | 12/2018 | DiVincenzo et al. | |
| 2019/0247102 | A1 | 8/2019 | Biedermann | |
| 2020/0281608 | A1 | 9/2020 | Sharifi-Mehr et al. | |
| 2023/0293217 | A1* | 9/2023 | Geist | A61B 17/8897 |
| | | | | 606/104 |

OTHER PUBLICATIONS

International Written Opinion corresponding to related International Patent Application No. PCT/US2022/075889 mailed Nov. 22, 2022, 10 pages.

International Preliminary Report corresponding to related International Application No. PCT/US2022/075889, date of mailing Mar. 21, 2024, 10 pages.

* cited by examiner

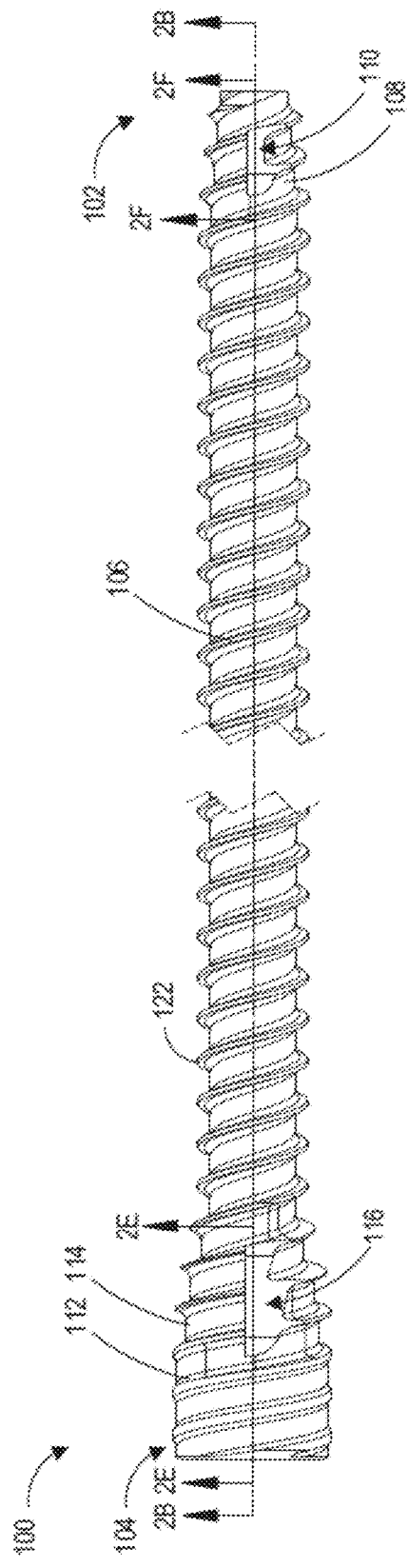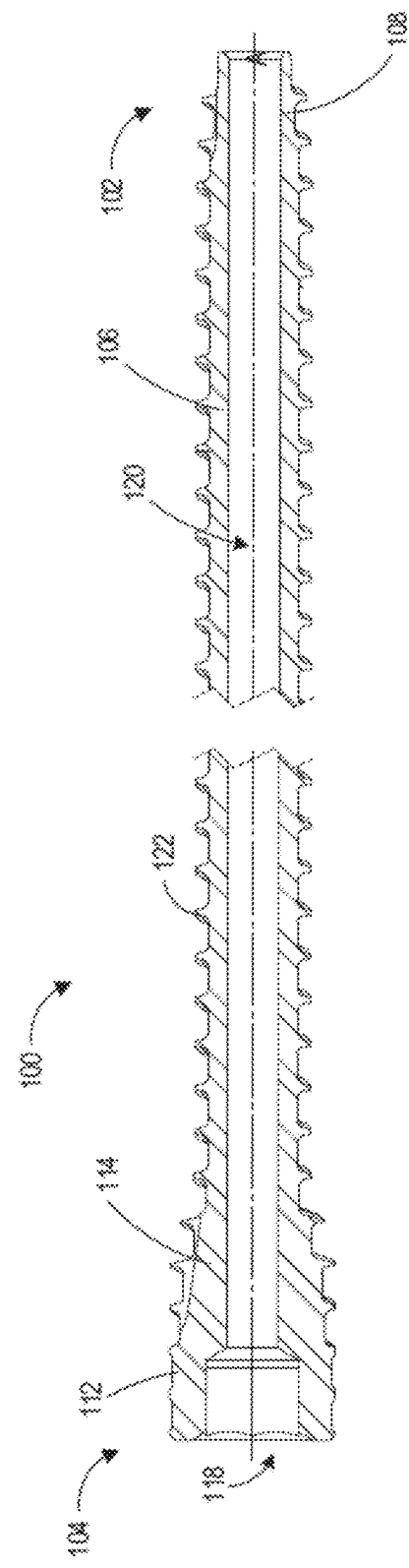
FIG. 2A
FIG. 2B

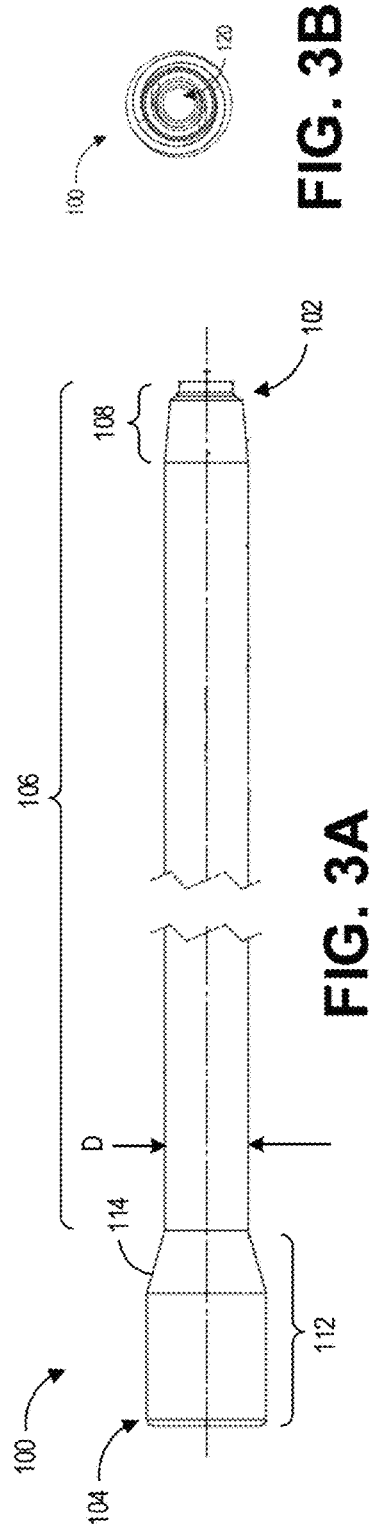
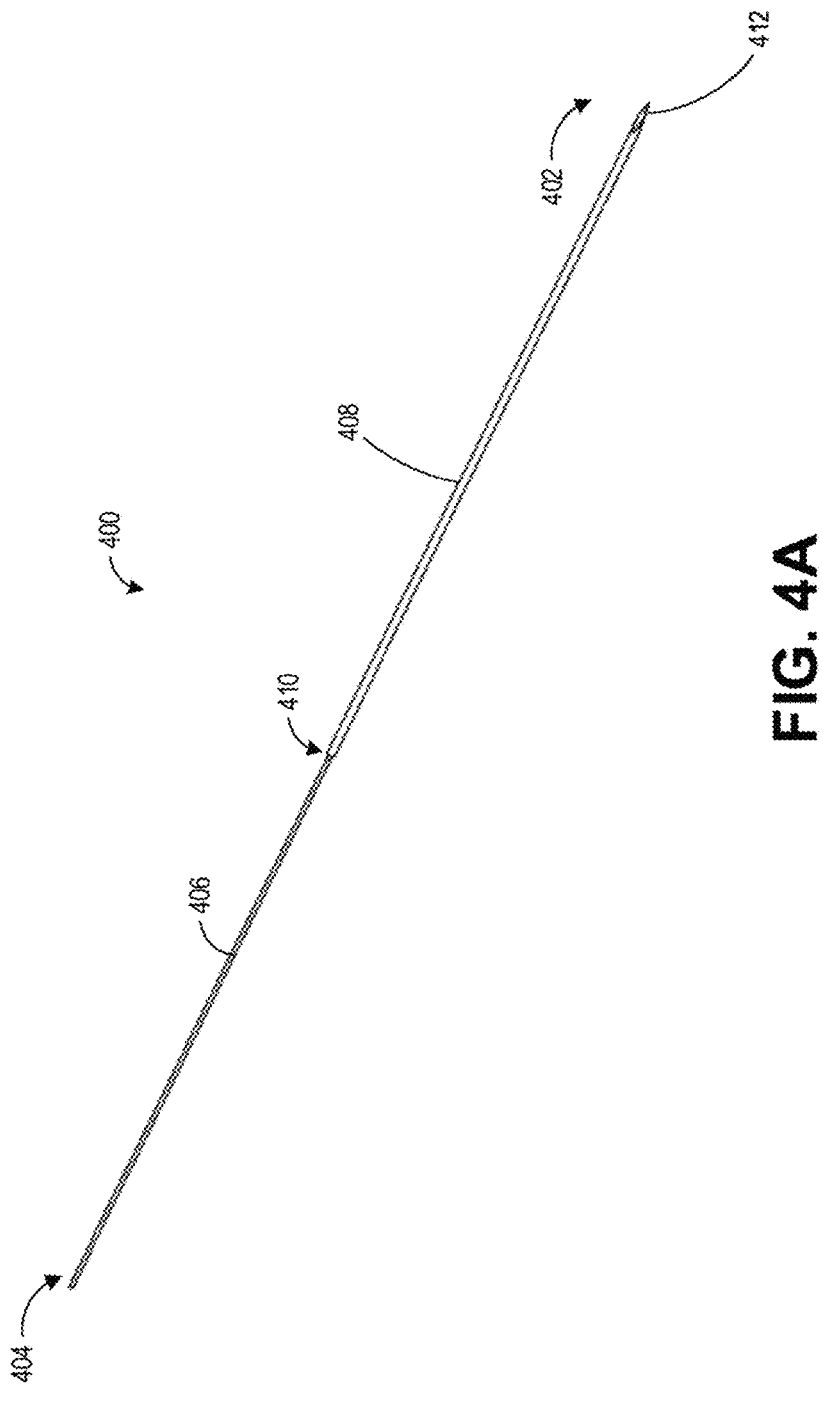
FIG. 3A
FIG. 3B
FIG. 4A

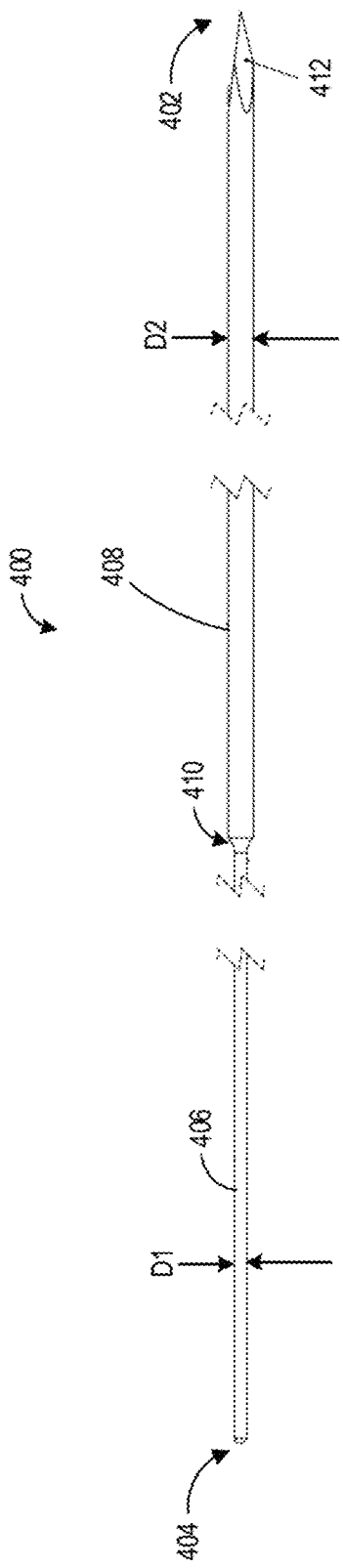
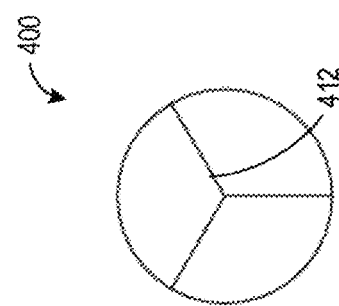
FIG. 4B
FIG. 4C

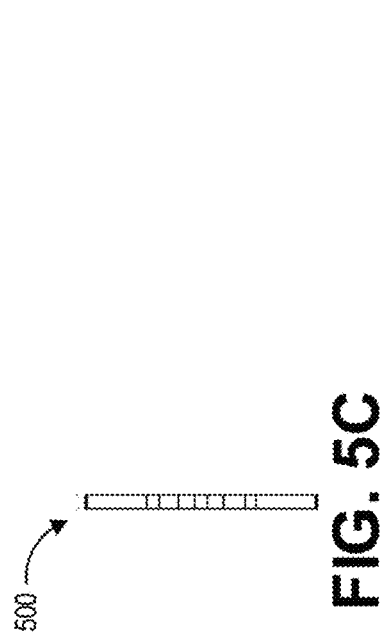
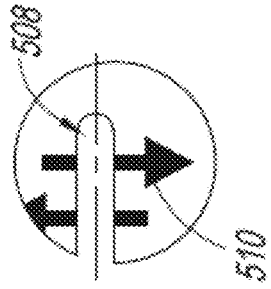
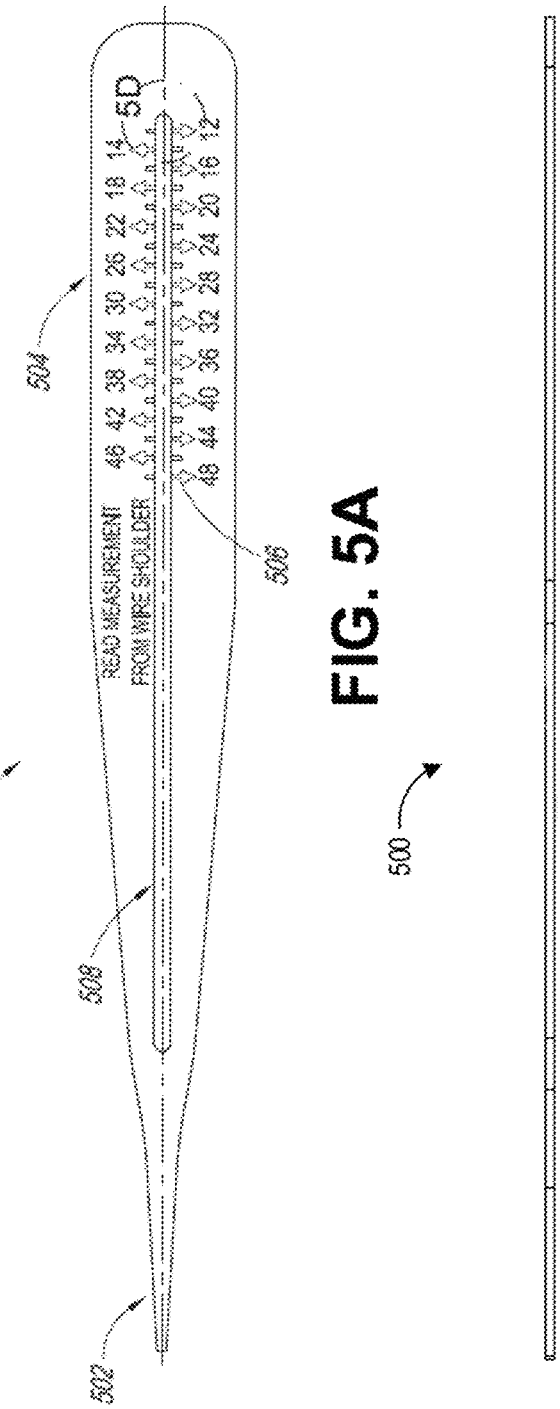
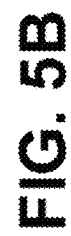
FIG. 5A
FIG. 5B
FIG. 5C
FIG. 5D

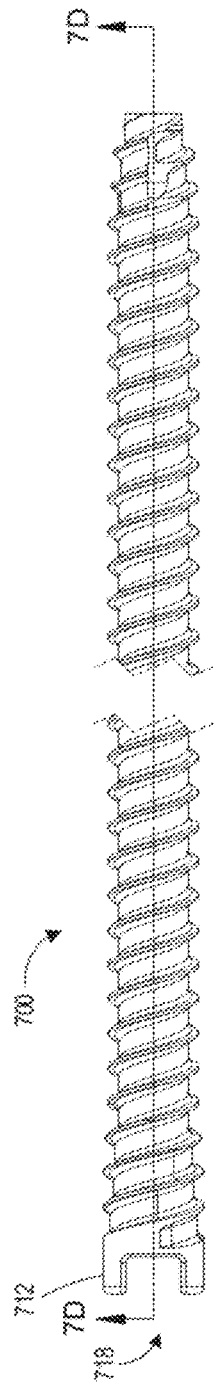
FIG. 7A
FIG. 7B
FIG. 7C
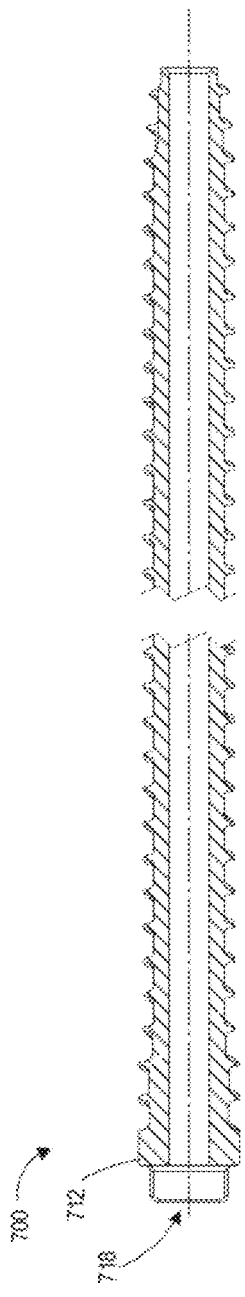
FIG. 7D

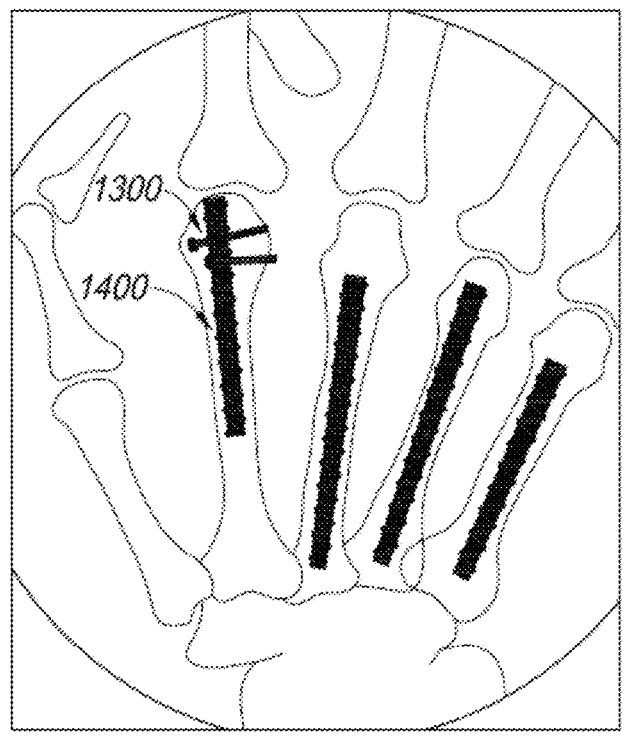
FIG. 16
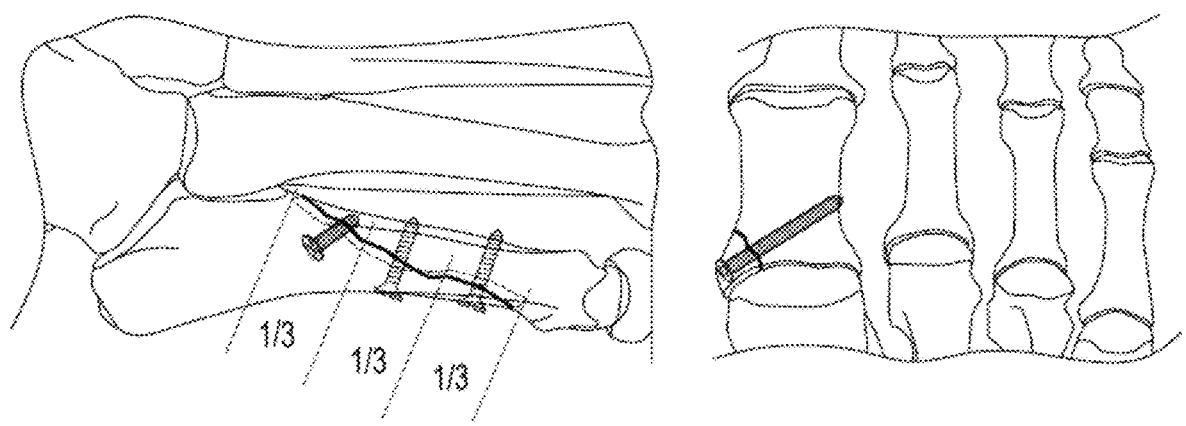
FIG. 17A  FIG. 17B

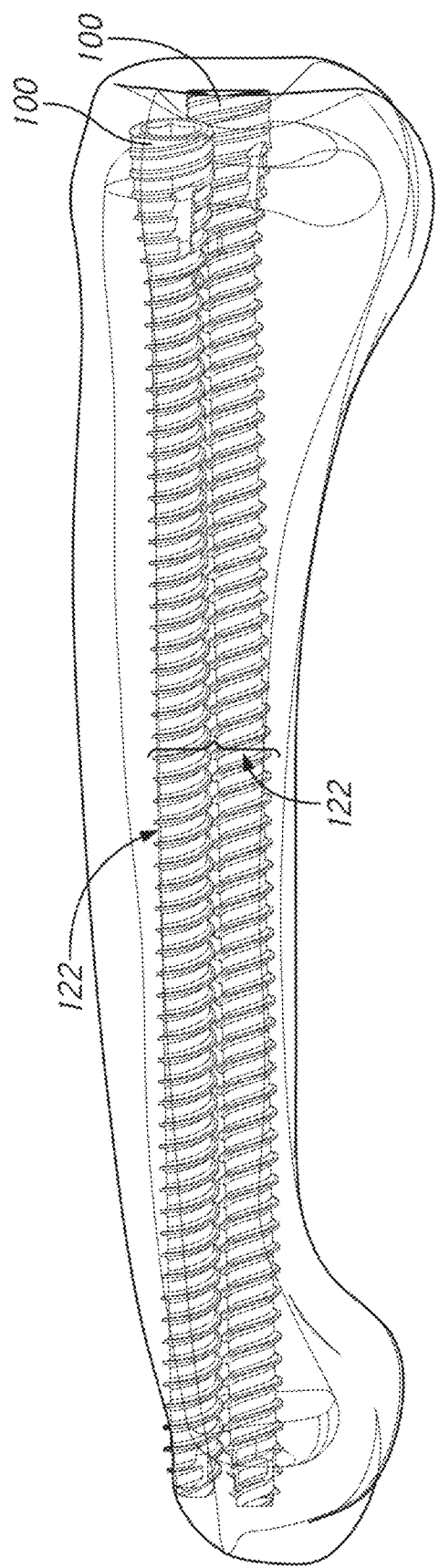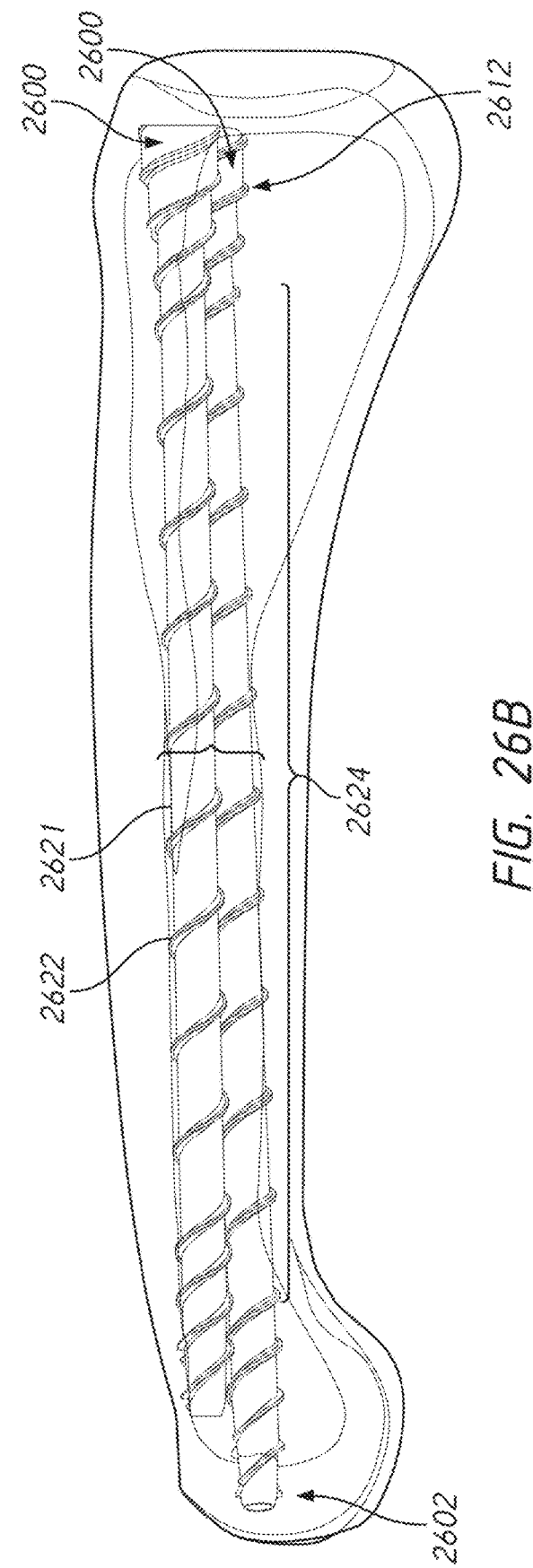
FIG. 26A
FIG. 26B

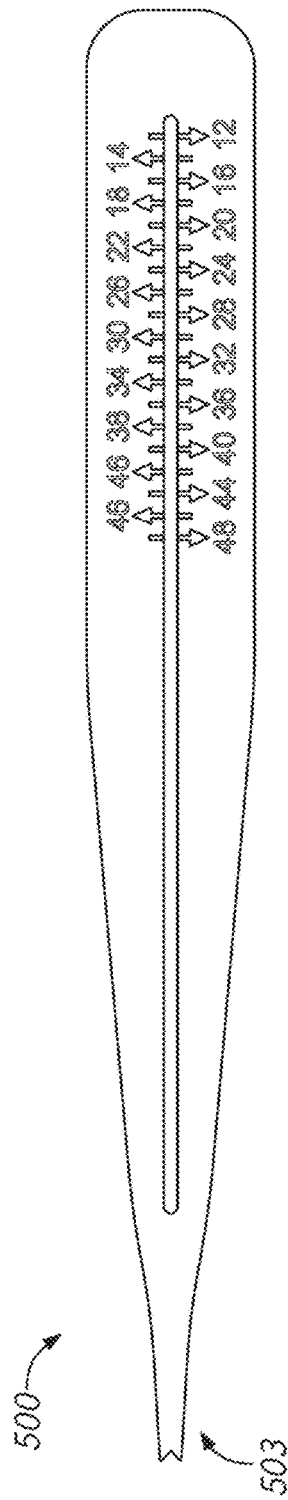
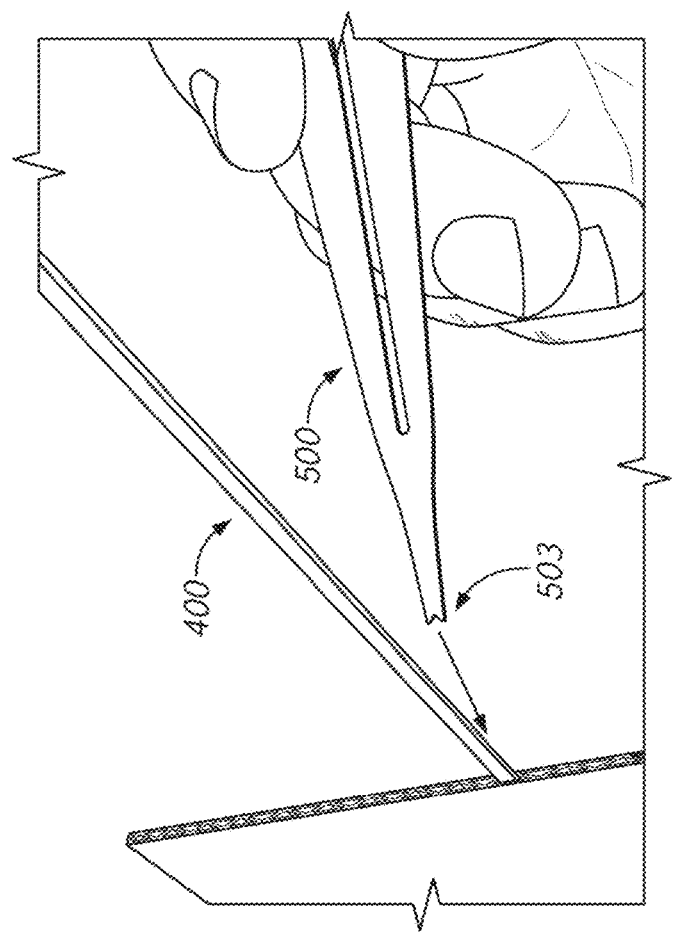
FIG. 28A
FIG. 28B

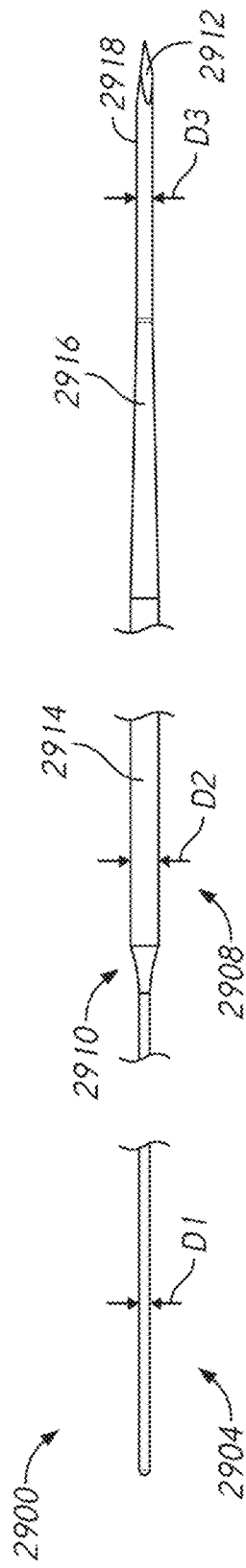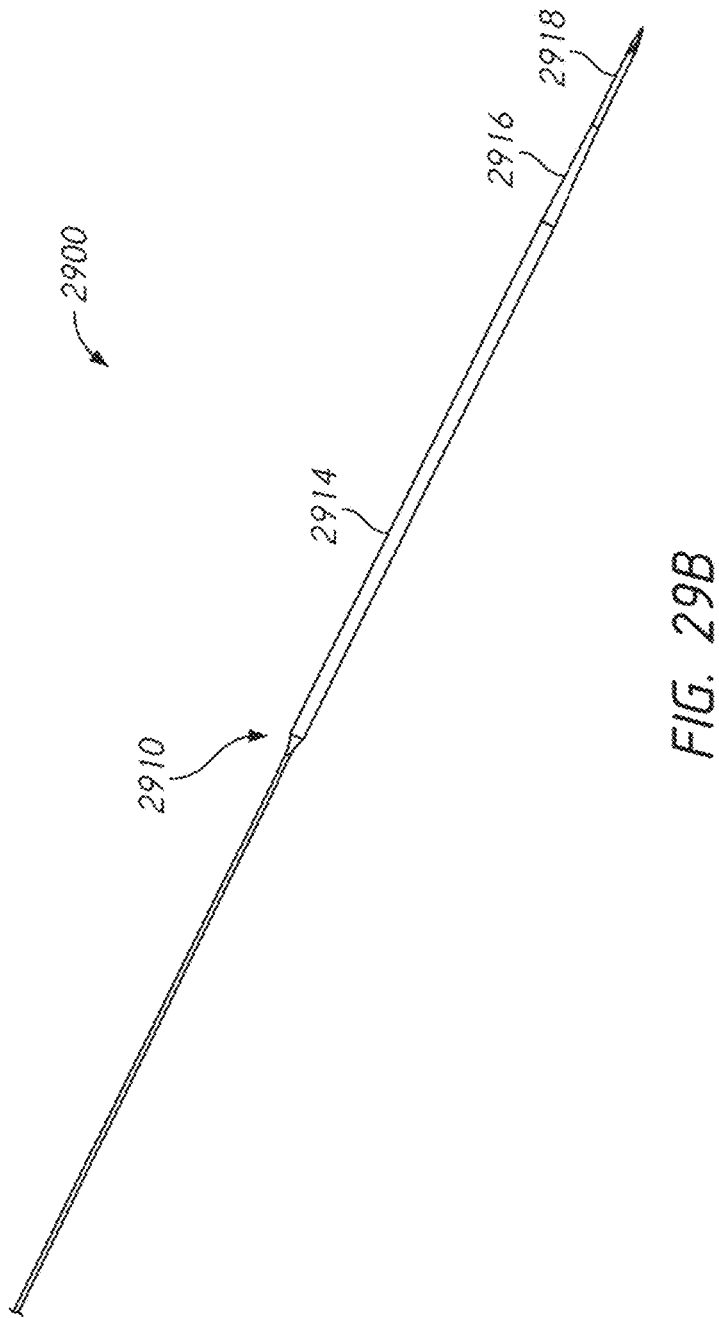
FIG. 29A
FIG. 29B

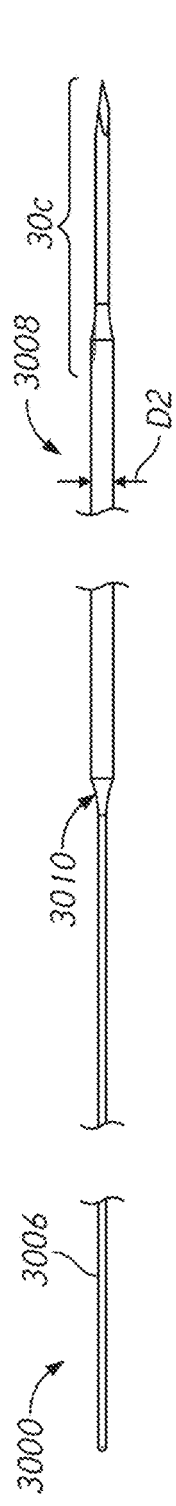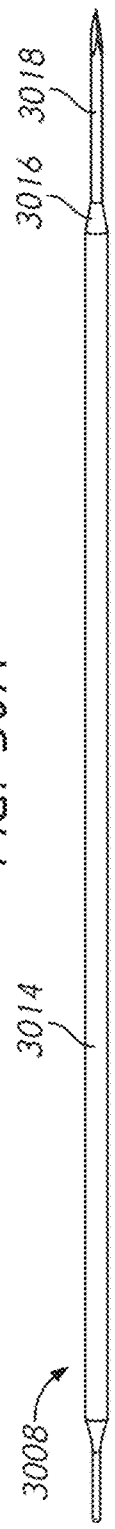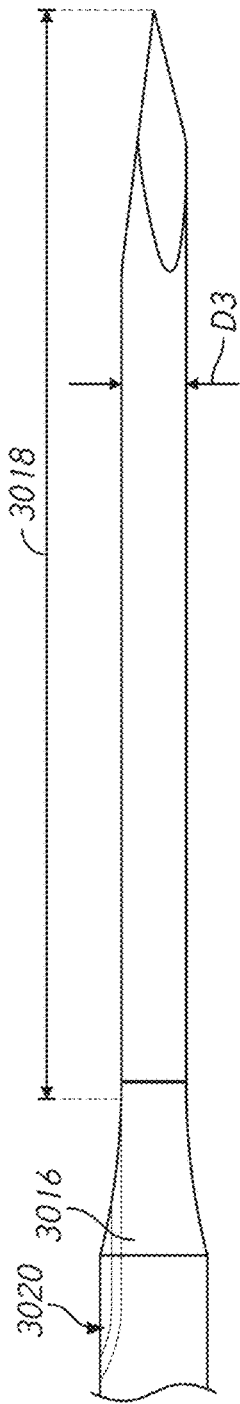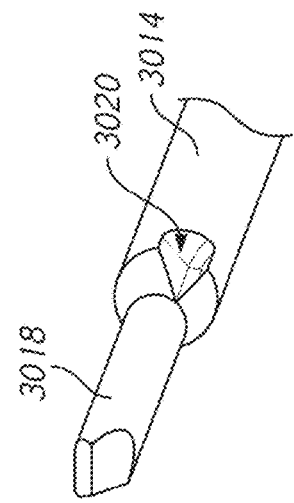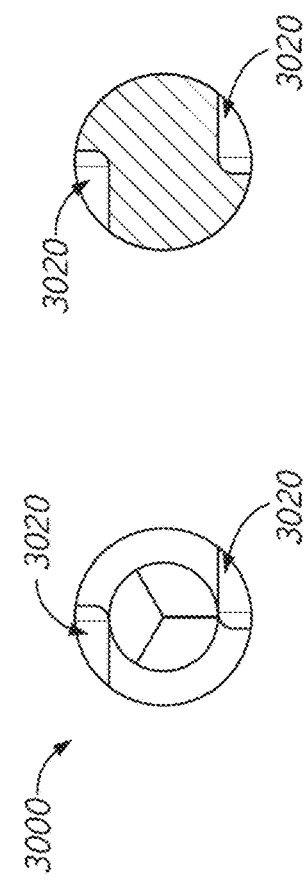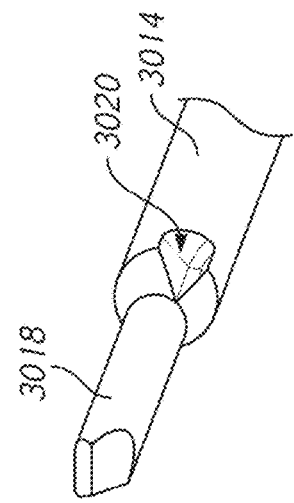
FIG. 30A
FIG. 30B
FIG. 30C
FIG. 30D
FIG. 30E
FIG. 30F

ORTHOPEDIC IMPLANTS AND INSTRUMENTS FOR DELIVERING THE SAME

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the priority benefit of U.S. Provisional Application No. 63/261,028, filed Sep. 9, 2021, the entirety of which is incorporated herein by reference.

BACKGROUND

The present disclosure relates to systems and methods of treating bone fractures, particularly of fractures in a small bone.

FIELD

Hand and foot injuries are common. For example, approximately 20% of all emergency visits are due to traumatic finger injuries. These injuries can include sports and work-related injuries. As many as about 5% of hand injuries may require surgical intervention.

Phalangeal and metacarpal fractures are among the most common skeletal injuries. Fractures are estimated at a domestic incidence rate of 12.5% for the phalanges and 8.4% for the metacarpals per 10,000 people annually. Such fractures can be an inconvenience or even debilitating to the patient. For example, lost productivity associated with phalangeal fractures is estimated to exceed $2 billion per year in the U.S.

The primary objectives of phalangeal and metacarpal fracture treatment include restoring anatomy and preserving function of the fracture bone as early as possible. Small bone fractures, such as phalangeal and metacarpal fractures, can be treated using, for example, K-wires, intraosseous wires, tendon band wires, compression screws, fixation plates, or external fixation. Some of these procedures are performed percutaneously.

SUMMARY

Current standard of care for small bone fractures may result in poor rotation control, delayed mobilization, prolonged stiffness, reduced range of motion, soft tissue irritation, increased operative exposure, and postoperative tendon adhesions, among other disadvantages.

Better rotation control and/or bone reduction can be achieved by implants that hold both cortical walls (also referred to as "bicortical purchase"). Currently this procedure is performed using cross-pinned off-the-shelf K-wires. However, the use of off-the-shelf K-wires has disadvantages. For example, the use of off-the-shelf K-wires results in at least one end of the K-wires to protrude from the bone surface. The protruding end of K-wires can cause pin-site infection.

The present disclosure can improve the surgical outcome of the cross-pinning technique using a combination of fracture fixation implants and guide wires having at least two diameters, for example, a dual-diameter guide wire. The fracture fixation systems disclosed herein can be delivered percutaneously to avoid the need for open reduction. The fracture fixation systems and the methods of delivery disclosed herein can reduce and/or minimize surgical time, recovery time, and/or infection, and can expedite return to activity. The fracture fixation systems and the methods of delivery disclosed herein can also more quickly restore anatomy and enable mobilization of the injured digit (finger or toe) as soon as fracture stability permits. The fracture fixation systems and the methods of delivery disclosed herein can also minimize soft tissue injury and/or impingement.

A fracture fixation system of the present disclosure can include two intramedullary fixation implants, which may be threaded, cross-pinned into the medullary canal guided by the customized guide wires having at least two diameters. Alternatively, the two implants can be implanted substantially parallel with each other. The system allows for more accurate sizing of the length of implants needed to achieve bicortical purchase for enhanced stability, as well as anti-rotation of the fracture site. The more accurate sizing and placement of the implant additionally allow both distal and proximal ends of the implants to be flush or recessed beneath the outer cortical walls, which can reduce the risk of infection. The fixation implants are also designed to reduce displacement after implantation, for example, by having threads or otherwise a non-smooth outer shaft surface.

In the present disclosure, an example guide wire having at least two diameters and configured to deliver a cannulated orthopedic implant can comprise a first portion having a first generally uniform outer diameter; and a second portion, the second portion including at least a first segment and a second segment, the first segment having a second generally uniform outer diameter that is greater than the first generally uniform outer diameter, the second segment having a third outer diameter that is smaller than the second outer diameter, wherein the cannulated orthopedic implant can be configured to be slidably mounted onto the first portion of the guide wire, the second generally uniform outer diameter being substantially the same as a minor or root diameter or an outer diameter of a shaft of the cannulated orthopedic implant.

In a configuration, a free end of the second portion can comprise a sharp tip.

In a configuration, the first generally uniform outer diameter can be between 0.7 mm to 0.9 mm.

In a configuration, the second generally uniform outer diameter can be between 1.5 mm to 2.0 mm.

In a configuration, the first and second segments can be separated by a third segment, an outer diameter of the third segment transitioning from the third outer diameter to the second outer diameter.

In a configuration, the first and second portions can be removably connected.

In a configuration, the second portion can comprise a cannulation configured to receive the first portion.

In a configuration, the cannulation can extend along an entire length of the second portion.

In a configuration, the cannulation can extend along a partial length of the second portion.

In a configuration, one of the first or second portions can include a hook and the other one of the first or second portions can include a loop.

A method of delivering an elongate threaded orthopedic implant into a bone, the implant being at least partially cannulated can use any of the guide wire configurations described above. The method can comprise using the second portion of the guide wire of any configurations described above, preparing a pathway in the bone, the pathway having a diameter substantially the same as the root or minor diameter of the elongate threaded orthopedic implant; inserting the first portion of the guide wire into a cannulation of the implant; and driving the implant through the pathway guided by the first portion of the guide wire.

In the present disclosure, an example method of intramedullary fracture fixation can comprise delivering a guide wire having at least two diameters across fractured portions of a fractured bone, the guide wire comprising a first, trailing portion having a first diameter and a second, leading portion including at least a first segment and a second segment, the first segment having a second diameter greater than the first diameter, the second segment having a third outer diameter that is smaller than the second outer diameter, wherein the delivering can comprise extending the second portion of the guide wire across a medullary canal of the bone until a leading tip of the guide wire is substantially flush with an outer surface of the bone; selecting a cannulated elongate implant by determining a length of the cannulated elongate implant based on a position of the guide wire in the bone; slidably mounting the cannulated elongate implant onto the first portion of the guide wire; inserting the cannulated elongate implant into the bone guided by the guide wire, wherein ends of the cannulated elongate implant may not protrude from the outer surface of the bone; and removing the guide wire from the bone.

In the present disclosure, an example method of intramedullary fracture fixation can comprise delivering a first guide wire having at least two diameters across fractured portions of a fractured bone, the first guide wire comprising a first, trailing portion having a first diameter and a second, leading portion having a second diameter greater than the first diameter, wherein the delivering can comprise extending the second portion of the first guide wire across a medullary canal of the bone until a leading tip of the first guide wire is substantially flush with an outer surface of the bone; selecting a first cannulated elongate implant by determining a length of the first cannulated elongate implant based on a position of the first guide wire in the bone; slidably mounting the first cannulated elongate implant onto the first portion of the first guide wire; inserting the first cannulated elongate implant into the bone guided by the first guide wire; removing the first guide wire from the bone; delivering a second guide wire having at least two diameters across fractured portions of a fracture bone, the second guide wire comprising a first, trailing portion having the first diameter and a second, leading portion having the second diameter greater than the first diameter, wherein the delivering can comprise extending the second portion of the second guide wire across the medullary canal of the bone until a leading tip of the second guide wire is substantially flush with the outer surface of the bone; selecting a second cannulated elongate implant by determining a length of the second cannulated elongate implant based on a position of the second guide wire in the bone; slidably mounting the second cannulated elongate implant onto the first portion of the second guide wire; inserting the second cannulated elongate implant into the bone guided by the second guide wire; and removing the second guide wire from the bone, wherein a root diameter surface of the first implant can be in contact with a root diameter surface of the second implant.

In a configuration, each of the first and second implants can be bi-cortical.

In a configuration, each of the first and second implants can terminate at or prior to the outer surface of the bone.

In a configuration, ends of each of the first and second implants may not protrude into tissue surrounding the bone.

In a configuration, delivering the second guide wire can be performed after removing the first guide wire from the bone.

In a configuration, delivering the second guide wire can be performed after delivering the first guide wire and before inserting the first implant.

In a configuration, the delivering can comprise extending the second portion of the second guide wire across the medullary canal of the bone in a cross pattern with the tunnel in the bone created by the second portion of the first guide wire.

In a configuration, the delivering can comprise extending the second portion of the second guide wire across the medullary canal of the bone to be substantially parallel with the tunnel in the bone created by the second portion of the first guide wire.

In a configuration, the first and/or second cannulated elongate implants can include a thread, the thread in a middle portion having a greater pitch than the thread at or around a driver head or the leading tip.

In a configuration, a major outer diameter of the first and/or second cannulated elongate implants can be smaller in the middle portion than at or around the driver head or the leading tip.

In the present disclosure, an example kit for an intramedullary fracture system can comprise a first elongate implant, the first elongate implant being cannulated and having a first implant shaft outer diameter and a first implant cannulation diameter; a guide wire that can have at least two diameters and configured to deliver the first implant into a fracture bone by intramedullary fixation. The guide wire can comprise a first, trailing portion having a first diameter and a second, leading portion including at least a first segment and a second segment, the first segment having a second diameter greater than the first diameter, the second segment having a third outer diameter that is smaller than the second outer diameter, the second diameter being substantially the same as a first implant shaft outer diameter (or a first implant root or minor diameter), the first implant cannulation diameter configured to accommodate the first portion of the guide wire; and a second elongate implant configured to be implanted with the first implant by intramedullary fixation, the second elongate implant being cannulated and having a second implant shaft outer diameter (or a second implant root or minor diameter) and a second implant cannulation diameter, wherein the second diameter of the guide wire can be substantially the same as the second implant shaft outer diameter or a root or minor diameter of the second implant, and the second implant cannulation diameter can be configured to accommodate the first portion of the guide wire.

In a configuration, the kit can further comprise a second guide wire having at least two diameters and configured to deliver the second implant into the fracture bone for intramedullary fixation, the second guide wire comprising a first, trailing portion having the first diameter and a second, leading portion having the second diameter greater than the first diameter, the second diameter being substantially the same as the second implant shaft outer diameter or the second implant root or minor diameter, the second implant cannulation diameter configured to accommodate the first portion of the second guide wire.

In a configuration, the first and/or second elongate implants can be threaded.

In a configuration, the second elongate implant can be configured to be implanted in a cross pattern with the first implant.

In a configuration, the second elongate implant can be configured to be implanted substantially parallel with the first implant.

A surgical kit can be used for performing fracture fixation using a cannulated implant that can comprise a head and an at least partially threaded shaft. The surgical kit can comprise a guide wire having at least two diameters and configured to guide delivery of the implant into a fracture bone, the guide wire comprising a first, trailing portion having a first diameter and a second, leading portion including at least a first segment and a second segment, the first segment having a second diameter greater than the first diameter, the second diameter being substantially the same as a minor diameter of the shaft of the implant, the first diameter of the first portion configured to slidably engage a cannulation of the implant, the second segment having a third outer diameter that is smaller than the second outer diameter; a sizing tool; and a driver configured to engage the head of the implant to drive the implant into the bone.

In a configuration, the surgical kit can further comprise a sterile sealed packaging, wherein the guide wire, the sizing tool, and the driver can be enclosed within the sterile sealed packaging.

In a configuration, the guide wire, the sizing tool, and/or the driver can be configured for single use.

In a configuration, the guide wire, the sizing tool, and/or the driver can be re-usable by being sterilized after each use.

For purposes of summarization, certain aspects, advantages and novel features are described herein. Of course, it is to be understood that not necessarily all such aspects, advantages or features need to be present in any particular embodiment.

BRIEF DESCRIPTION OF THE DRAWINGS

These and other features, aspects, and advantages of the present disclosure are described with reference to the drawings of certain embodiments, which are intended to schematically illustrate certain embodiments and not to limit the disclosure.

FIG. 2A illustrates a side view of an example implant of the present disclosure.

FIG. 2B illustrates a cross-sectional view along a longitudinal axis (axis B-B) of the implant of FIG. 2A.

FIGS. 3A and 3B illustrate side and leading end views of a non-threaded (also referred to as "blank") version of the implant of FIG. 2A.

FIG. 4A illustrates a perspective view of an example customized guide wire having at least two diameters.

FIG. 4B illustrates a side view of the guide wire of FIG. 4A.

FIG. 4C illustrates a leading end view of the guide wire of FIG. 4A.

FIG. 5A illustrates a front view of an example sizing tool for use in delivery of the device of FIG. 2A.

FIG. 5B illustrate a side view of the sizing tool of FIG. 5A.

FIG. 5C illustrates an end view of the sizing tool of FIG. 5A.

FIG. 5D illustrates a detailed view of a portion of the sizing tool of FIG. 5A.

FIG. 7A illustrates a side view of another example implant of the present disclosure.

FIG. 7B illustrates a trailing end view of the implant of FIG. 7A.

FIG. 7C illustrates a leading end view of the implant of FIG. 7A.

FIG. 7D illustrates a cross-sectional view along a longitudinal axis (axis B-B) of the implant of FIG. 7A.

FIG. 16 illustrates x-ray images of lag screws implanted with an intramedullary implant in a metacarpal bone.

FIGS. 17A-17B illustrate example lag screws for various fixation of bones in a foot.

FIG. 26A illustrates two implants of FIG. 2A inserted with outer diameter to outer diameter (also referred to as thread to thread) contact.

FIG. 26B illustrates two implants of alternative design inserted with root diameter to root diameter contact.

FIGS. 28A-28D illustrate an example sizing tool with a guide wire engaging feature at a tip of the sizing tool.

FIG. 29A illustrates a side view of a guide wire with a second portion of an alternative design.

FIG. 29B illustrates a perspective view of the guide wire of FIG. 29A.

FIG. 30A illustrates an example alternative design of the guide wire of FIG. 29A to include a cutting flute.

FIG. 30B illustrates an enlarged view of the second portion of FIG. 30A.

FIG. 30C illustrates a detailed view of a distal section of the guide wire of FIG. 30A.

FIG. 30D illustrates an end view of the guide wire of FIG. 30A.

FIG. 30E illustrates a cross-sectional view of the guide wire of FIG. 30C along axis B-B.

FIG. 30F illustrates a detailed perspective view of the distal section of the guide wire of FIG. 30A.

DETAILED DESCRIPTION

Although certain embodiments and examples are described below, those of skill in the art will appreciate that this disclosure extends beyond the specifically disclosed embodiments and/or uses and obvious modifications and equivalents thereof. For example, the example cross-pinned intramedullary fixation system may also be implanted in bones in other parts of the human body, such as in the foot. Thus, it is intended that the scope of the disclosure herein should not be limited by any particular embodiments described below.

In fracture treatments, a single elongate intramedullary implant may not have sufficient rotation control when used to stabilize a fractured small bone, for example, the phalanx. The fractured digit tends to spin on the longitudinal axis of the implant. It is beneficial that the implant can resist rotation, not protrude from the bone into the soft tissue, and is also strong enough to allow the patient to regain function of the fractured digit earlier than the current standard of care. Better rotation control and/or bone reduction can be achieved by two cross-pinned intramedullary implants that each hold both cortical walls of the bone, that is, with bicortical purchase. Alternatively, two implants, each with bicortical purchase, can be implanted substantially parallel with each other.

Figure 1:
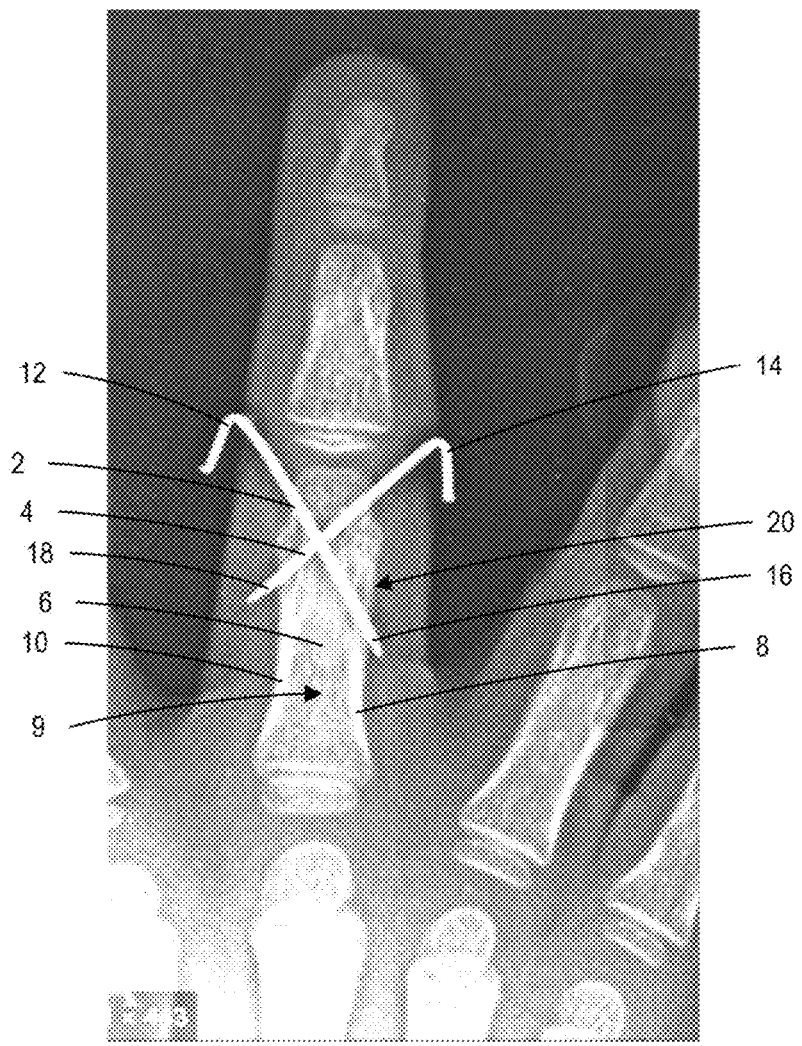
FIG. 1 illustrates an x-ray view of prior art cross-pinned K-wires implanted in a bone of a digit.

Currently the cross-pinning procedure is performed using standard off-the-shelf K-wires. Such K-wires can have an outer diameter of between about 1.1 mm (0.045") to about 1.6 mm (0.060"). FIG. 1 illustrates implantation of a pair of cross-pinned standard K-wires 2, 4 to treat a fractured phalanx 6 of a person's hand. However, the results with the cross-pinned standard K-wires 2, 4 are poor for many reasons. For example, the K-wires 2, 4 have a generally uniform outer shaft diameter and a relatively smooth outer surface and therefore poor bone purchase. The K-wires 2, 4 can be easily displacement post-surgery due to the poor bone purchase.

Additionally, the poor result can be due to the fact that the length of the K-wires 2, 4 cannot be sized properly relative to the size of the phalanx 6. When a K-wire is inserted to treat a fractured bone, the K-wire penetrates the skin, fascia, fat, tendon, periosteum, and the like, before reaching the bone. As shown in FIG. 1, when the K-wires 2, 4 are implanted across cortical walls on generally diametrically opposite sides 8, 10 of the phalanx 6 across a medullary canal 9, portions of the K-wires 2, 4 at the trailing ends 12, 14 are exposed transcutaneously. Portions of the K-wires 2, 4 at the leading end 16, 18 can also protrude outward from, that is, sit proud of, the outer surface 20 of the phalanx 6.

The transcutaneously exposed portions at the trailing ends 12, 14 can be cut off using a wire cutter. However, the K-wires 2, 4 at the trailing end 12, 14 can still sit proud of the outer surface of the phalanx 6. The leading 16, 18 and/or trailing 12, 14 ends of the K-wires 2, 4 can therefore protrude from the outer surface 20 of the phalanx 6 by at least about 1 mm to about 2 mm. A scar can develop from the bone to the skin due to the protruding leading 16, 18 and/or trailing ends 12, 14 of the K-wires 2, 4 from the outer surface 20 of the bone 6. The tissue layers surrounding the bone 6 can slide against the scar, which can cause adhesion of the tissue layers. Moreover, the cut trailing end 12, 14 of the K-wires can still be exposed at the wound on the skin, causing pin-site infection. In one study, metacarpal fractures treated with exposed K-wires were 2 times more likely to be treated for a pin-site infection (17.6% of exposed K-wire cases vs. 8.7% of buried K-wire cases).

Because of the poor fixation and/or the need to reduce occurrence of tissue damage or pin-site infection, the fractured digit may need to be further stabilized using a cast after the implantation of the cross-pinned K-wires, which can cause more inconvenience to the patient and can further delay recovery of the fractured digit.

To improve bone purchase of the fixation implant, threaded implants, such as screws, can be used. The screws may need to be delivered via K-wires and therefore need to be cannulated. The cannulated delivery technique can make the surgical procedure safer and easier as the delivery path can be guided by a pre-inserted guide wire, such as a K-wire. A K-wire suitable for this cannulated delivery technique preferably has an outer diameter of at least about 1.1 mm. K-wires with an outer diameter smaller than 1.1 mm may less stiff and too flexible so that the K-wire can skive when being inserted into the bone with a driver and are more prone to deviating from a straight pathway into the bone. However, standard cannulated off-the-shelf screws can have a diameter that is too large for use in phalanx intramedullary fixation or fixation of other hand and/or foot bones. This is because the screws need to be no smaller than about 2.8 mm to about 3 mm in the shaft outer diameter in order to have a cannulation sized sufficient to accommodate a K-wire having an outer diameter of at least about 1.1 mm. However, the screws with a shaft outer diameter of at least 2.8 mm may result in there being insufficient room for the cross-pin pattern (also referred to as the "cross pattern") in a small bone like the phalanx. Although the wall thickness in the shaft of the screws can be trimmed or reduced, for example, from about 2.8 mm to be less than 2.5 mm, to provide more room, the trimmed screws then may not have a sufficient length to achieve bicortical purchase in the phalanx when implanted in the cross-pin pattern. This is because the maximum allowable screw length is dependent on the shaft wall thickness of the screw. A longer screw requires a greater wall thickness to maintain the screw's structural rigidity and strength.

The present disclosure provides example systems of cross-pinned fixation implants that may be threaded and/or cannulated while having the desired dimensions suitable for phalanx (and other small bones) intramedullary fixation, including having bicortical purchase and improved rotation control. The present disclosure also provides example instruments, including but not limited to a customized guide wire having at least two diameters, to allow easier sizing of the length of the fixation implants and easier delivery of the implants.

Example Intramedullary Fixation System

FIGS. 2A-2F illustrate a non-limiting example orthopedic implant 100 of the present disclosure. FIGS. 3A and 3B illustrate a blank version of the implant 100 of FIGS. 2A-2F. The blank is illustrated with the threads omitted to more clearly illustrate certain features of the implant 100.

The implant 100 can be formed of any suitable material, for example, titanium, stainless steel, or other metals and/or alloys. As shown, the implant 100 can have a leading end 102 and a trailing end 104. A total length between the leading end 102 and the trailing end 104 can be, for example, between about 10 mm to about 50 mm, or between about 12 mm to about 48 mm, or between about 20 mm to about 48 mm, or between about 24 mm to about 46 mm, or between about 28 mm to about 44 mm, or between about 32 mm to about 42 mm, or between about 36 mm to about 40 mm. All the ranges provided in the present disclosure include the end values.

The implant 100 can include a through-cannulation 120 along its longitudinal axis A so as to accommodate a delivery guide wire (for example, the guide wire 400 in FIGS. 4A-4C, which will be described in greater detail below). The through-cannulation 120 can have an inner diameter that can be, for example, smaller than about 1 mm, or between about 0.80 mm to about 0.96 mm, or between about 0.84 mm to about 0.94 mm.

A shaft 106 can extend from the leading end 102 toward the trailing end 104. As shown in FIG. 3A, the shaft 106 can have a generally uniform outer (or major) diameter D except for a leading portion 108 (see also FIG. 2F). The outer diameter D can be less than about 2.5 mm, or less than about 2.4 mm, or less than about 2.2 mm, or less than about 2.1 mm, or less than about 2.0 mm. The leading portion 108 can taper from the outer diameter D to a smaller diameter. The leading portion 108 can have a length of, for example, less than about 2 mm, or less than about 1.5 mm. As shown in FIG. 2A, the leading portion 108 can include one or more cutting features 110, for example, one or more cutting flutes. The taper and/or cutting feature(s) of the leading portion 108 can facilitate easier insertion of the implant 100 into the bone, for example, into a pre-formed tunnel of the bone.

A driver head portion 112 can be located at the trailing end 104 and adjacent to the shaft 106. The driver head portion 112 can be, for example, less than about 4.0 mm, or less than 3.5 mm. As shown in FIGS. 2E and 3A, the driver head portion 112 can include a tapering part 114, transiting from an outer diameter of the driver head portion 112 to the outer diameter D of the shaft 106. The outer diameter of the driver head portion 112 can be, for example, less than about 3.0 mm, or between about 2.5 mm to between about 3.0 mm, or between about 2.6 mm to between about 2.9 mm. As shown in FIG. 2A, the driver head portion 112 can include one or more cutting features 116, for example, one or more cutting flutes, which can be located mostly or at least partially in the tapering part 114.

Figure 2C:
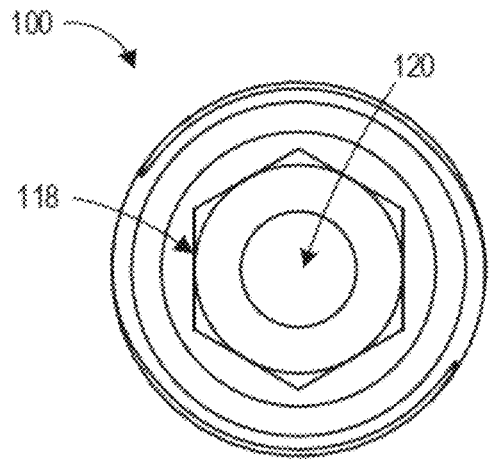
FIG. 2C illustrates a trailing end view of the implant of FIG. 2A.
Figure 2D:
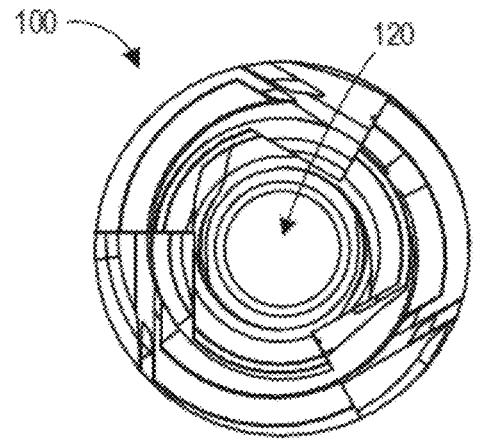
FIG. 2D illustrates a leading end view of the implant of FIG. 2A.
Figure 2E:
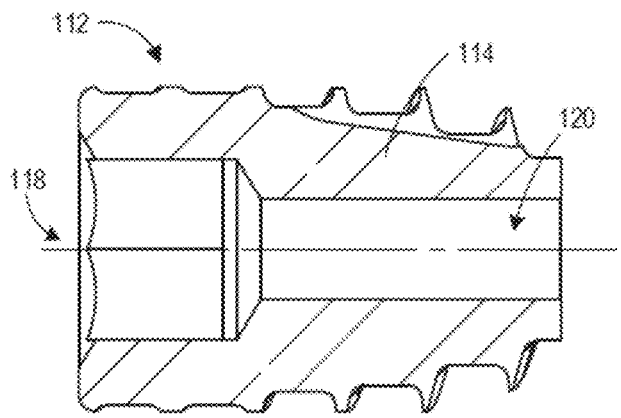
FIG. 2E illustrates a partial cross-sectional view of the implant of FIG. 2A along axis C-C.
Figure 2F:
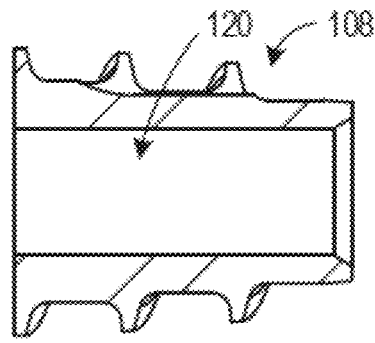
FIG. 2F illustrates a partial cross-section view of the implant of FIG. 2A along axis A-A.

The driver head portion 112 can include a driver interface, for example, a hex interface 118 as shown in FIG. 2C. The hex interface 118 can include a greater inner diameter than the outer diameter of the throughbore 120. The driver interface can allow transmission of torque from a driver (for example, the driver 600 in FIGS. 6A-6D, which will be described in more detail below) to the implant 100 for delivery of the implant 100 into the bone. Alternatively, the driver interface can be a slot interface 718 in a driver head portion 712 of an implant 700 such as shown in FIGS. 7A-7D. The implant 700 can include any of the features of the implant 100 disclosed herein and are not repeated here for brevity. The driver interface can also alternatively accept any other suitable driver configuration, for example, a Torx drive, Pozidriv, Robertson, tri-wing, Torq-Set, Spanner-Head, Triple Square, and the like.

The implant 100 can be threaded. As shown in FIGS. 2A and 2B, a thread 122 can extend along an entire length or substantially an entire length of the shaft 106. The thread 122 can optionally also extend along (entirely or at least partially) the driver head portion 112. The thread height can be lower in the driver head portion 112 than in the shaft 106. The shaft 106 can have a uniform thread height so that the shaft can have a generally uniform root or minor diameter. The thread 122 along the shaft 106 can have any suitable thread height (for example, between about 0.15 mm to about 0.30 mm, or between about 0.20 mm to about 0.25 mm, or otherwise) and/or pitch (for example, between about 0.5 mm to about 1.0 mm, or between about 0.7 mm to about 0.8 mm, or otherwise). The implant 100 can be a noncompression implant, and also alternatively can be a compression implant when compression is indicated, such as when fixing a transverse midshaft fracture. The cutting flute(s) described above in the leading portion 108 and the driver head portion 112 can interrupt the thread 122, making the thread 122 discontinuous and optionally serrated at the cutting flute(s). The interruption and/or serration of the thread 122 at the cutting flute(s) can facilitate delivery of the implant 100 into the bone. Alternatively, the implant 100 can be non-threaded. The non-threaded implant can optionally include other features protruding from an outer surface of the implant to improve bone purchase, for example, spikes, ridges, barbs, an uneven or roughened surface, and/or the like.

Figure 26C:
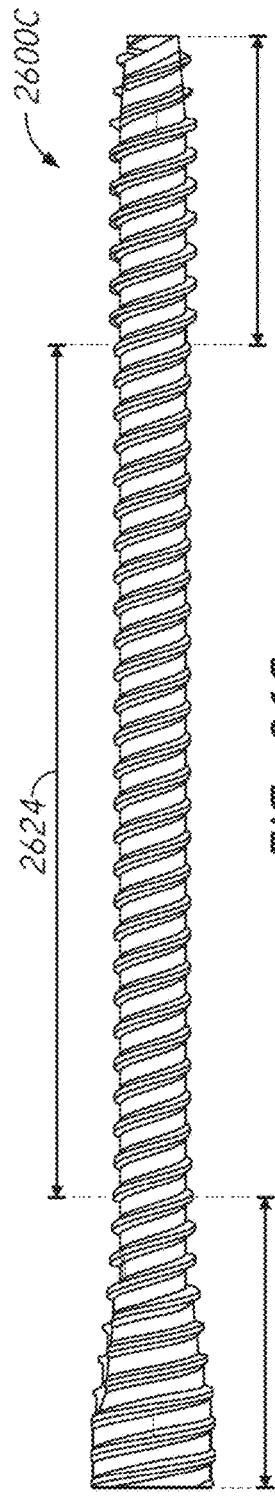
FIGS. 26C-26F illustrate example implants configured to reduce overall implants profile.
Figure 26D:
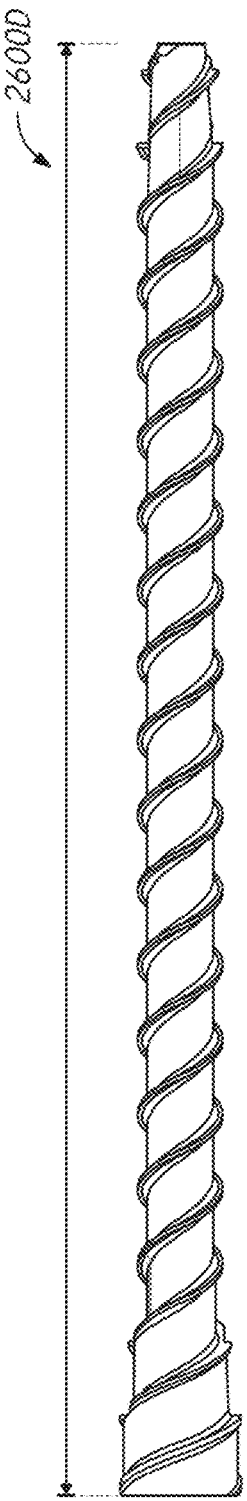
Figure 26E:
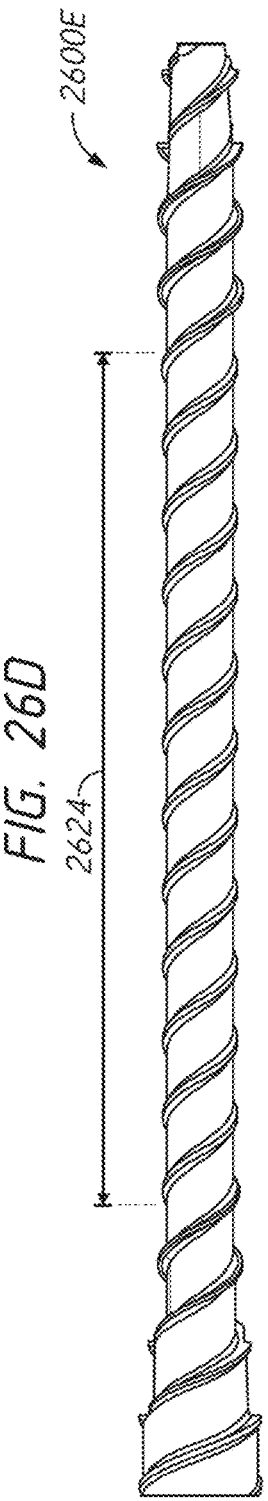

The thread of the implant can have a generally constant pitch or alternatively a varying thread pitch. Variations of the threads are illustrated with reference to FIGS. 26A-26F. The implants 2600, 2600C, 2600D, 2600E, 2600F shown in FIGS. 26B-26F can have any features of the implant 100 disclosed herein. The thread 122 can have a pitch such that when two implants 100 are inserted into the bone (such as using the method described below), the threads 122 of the two implants 100 are in contact, for example, as shown in FIG. 26A. Alternatively, such as shown in FIG. 26B, the threads 2622 of the implant 2600 can have a pitch such that when two implants 2600 are inserted, the implants 2600 make contact on a root diameter surface 2621. The root-to-root contact can further reduce the profile of the implants, which can be advantageous when inserting the implants into small bones with a small intramedullary canal, such as a phalanx. The root-to-root contact can reduce the profile of the implants by, for example, between about 15% to about 40%, or between about 20% to about 35%, or between about 30% to about 35%. The minimum root diameter of the implant can be maintained, thereby preserving the structural integrity and strength of the implant.

Figure 26F:
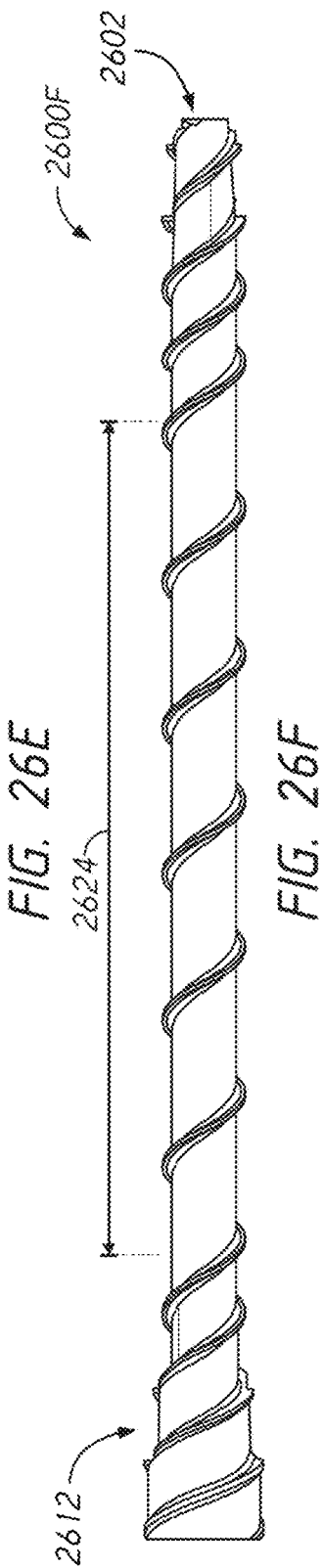

The implants can vary in the major diameter and/or the thread pitch to reduce the overall profile of the implants in the bone. FIGS. 26B-26F illustrate example implants 2600, 2600C, 2600D, 2600E, 2600F that can reduce the profile of the implants. Features of the implants 2600, 2600C, 2600D, 2600E, 2600F can be incorporated into one another. Dimensions shown in FIGS. 26C-26F are for illustration purposes only and are not meant to be limiting. For example, the entire thread of the implant 2600D, 2600E can have a thread pitch large enough to allow root-to-root contact. Alternatively, for example, the implants 2600, 2600F can have a greater thread pitch in a middle portion 2624 of the shaft to allow root-to-root contact when two implants are inserted into a small bone such as the phalanx, and a smaller or finer pitch at or around the driver head portion 2612 and the leading end 2602 to improve fixation strength between the implant and the cortical bone. Alternatively or additionally, the implant 2600C, 2600E may have a smaller major diameter in the middle portion 2624 of the shaft than at or around the driver head portion and the leading end of the implant to reduce the profile of the implant. Having a greater thread pitch and/or a smaller major diameter in the middle portion 2624 (for example, only in the middle portion) of the thread can reduce the profile of the implants, as well as improving fixation strength between the implant and the cortical bone, and not compromising the structural rigidity of the implant. As shown in FIGS. 26C-26F, the thread or a portion of the thread (for example, only at or near the two end of the implant) of the implant 2600C, 2600D, 2600E, 2600F can optionally be dual-lead. In FIG. 26F, having dual lead at the driver head portion 2612 and the leading end 2602 and single lead in the middle portion 2624 can allow the thread to be finer at the driver head portion 2612 and the leading end 2602 and larger in the middle portion 2624.

Various non-limiting examples of a guide wire for delivering the implant disclosed herein (or variations thereof based on this disclosure) is illustrated in FIGS. 4A-4C and 29A-32B. Certain features of the guide wire may be illustrated in certain embodiments of the guide wire. However, a guide wire with at least two diameters in the present disclosure can include features of any of the guide wire embodiments disclosed herein.

Figure 32A:
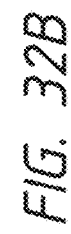
FIGS. 32A-32B illustrate example distal tips of a guide wire of the present disclosure.
Figure 32B:

As shown in FIGS. 4A-4C, a guide wire 400 can be made of any suitable material, for example, the same as the materials for a standard K-wire. The guide wire 400 can include a leading end 402 and a trailing end 404. The leading end 402 of the guide wire 400 can include a sharp tip 412, which, for example, can be a trocar tip with a three-sided cutting tip as shown in FIG. 4C, or can have any other shapes. The sharp tip 412 can facilitate easier insertion of the guide wire 400 into the bone via the leading end 402. The sharp tip at the leading end of the guide wire can have different sizes and/or shapes than the trocar tip shown in FIG. 4C. As shown in FIG. 32A, a trocar tip 3212 can have a smaller size compared to the trocar tip 412, also illustrated in FIG. 32B. As shown in FIGS. 31A-31D, the sharp tip 3112 of a guide wire 3100, which can incorporate any other features of the guide wire examples disclosed herein, can include a diamond style tip.

The guide wire 400 can include a first portion 406 with a first generally uniform diameter D1 and a second portion 408 with a second generally uniform diameter D2. The first portion 406 can be closer to the trailing end 404 and the second portion 408 can be closer to the leading end 402. The first portion 406 can extend from the trailing end 404 to. A transition portion (also referred to as a "wire shoulder" herein) 410 can couple the first portion 406 and the second portion 408. In some implementations, the transition portion can have zero length so that the first portion 406 transitions to the second portion 408 via a stepped transition. The transition portion can have a greater length than the transition portion 410 shown in FIGS. 4A and 4B. An example longer transition portion 2910, 3010 is shown in FIGS. 29A-29D and 30A-30B in different variations of the guide wire 400, compared to the transition portion 410 as shown in FIGS. 4A-4B.

D1 can be configured so that the first portion 406 can slidably receive the implant 100 via the through-cannulation 120. D1 can be, for example, smaller than about 1 mm, or smaller than about 0.8 mm, or between about 0.7 mm to about 0.8 mm. D2 is preferably greater than D1 and greater than the inner diameter of the through-cannulation 120. D2 can be similar or substantially the same as the outer diameter D of the implant 100. D2 can be, for example, greater than about 1 mm, or greater than about 1.1 mm, or between about 1.2 mm to about 2.5 mm, or between about 1.5 to about 2.0 mm.

The second portion of the guide wire may include more than one diameter. For example, as shown in FIGS. 29A-29E, the section portion 2908 of a guide wire 2900 can include a first segment 2914 and a second segment 2918. The first segment 2914 can be adjacent the transition portion 2910. The first segment 2914 can have the second diameter D2 described above. The second segment 2918 can be adjacent the sharp tip 2912. The second segment 2918 can have a third diameter D3 smaller than D2. The second segment 2918 can have a substantially uniform diameter. D3 may or may not be greater than D1. D3 may be, for example, between about 0.6 mm to about 1.5 mm, or between about 0.8 mm to about 1.2 mm, or between about 0.9 mm to about 1.0 mm. The smaller diameter of the second segment 2918 can facilitate insertion of the guide wire 2900 and starting of trajectory into the bone. The first and second segments 2914, 2918 can be separated by a third segment 2916. The third segment 2916 can be tapered so that the diameter of the third segment 2916 transitions from D2 to D3.

Figure 29C:
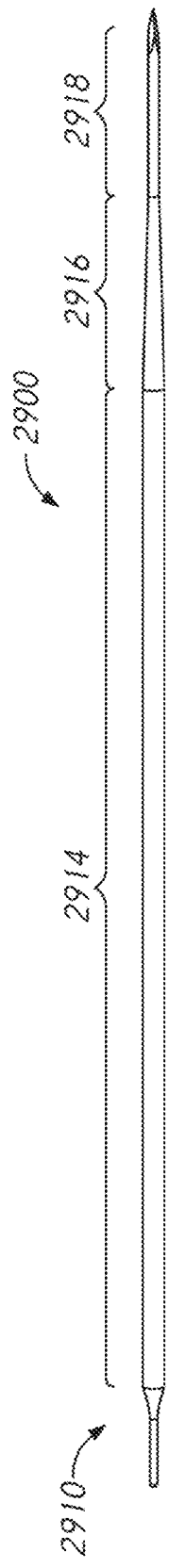
FIG. 29C illustrates an enlarged view of the second portion of FIG. 29A.
Figure 29D:
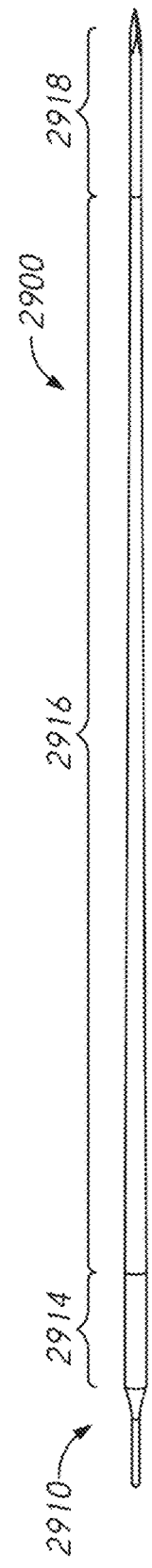
FIGS. 29D-29E illustrate various example alternative designs of a second portion of a guide wire.
Figure 29E:
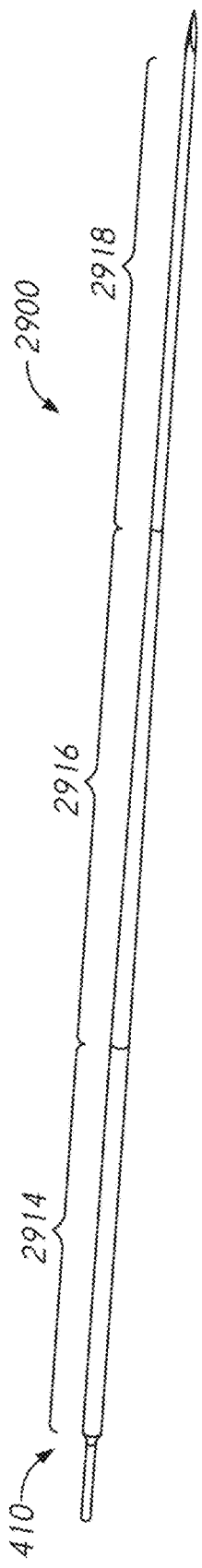
Figure 31A:
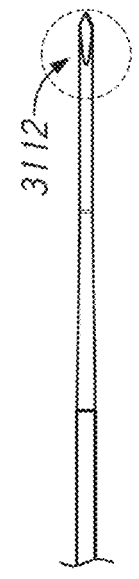
FIG. 31A illustrates an example alternative design of the guide wire of FIG. 29A to include a diamond style tip as the sharp tip.
Figure 31B:
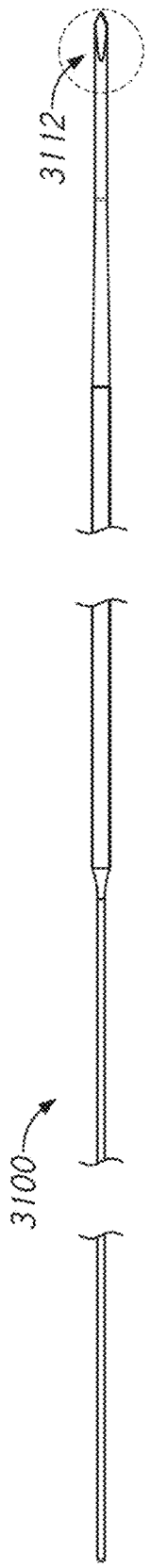
FIG. 31B illustrates a detailed front view of the diamond style tip.
Figure 31C:
FIG. 31C illustrates a side perspective view of the guide wire of FIG. 31A.
Figure 31D:
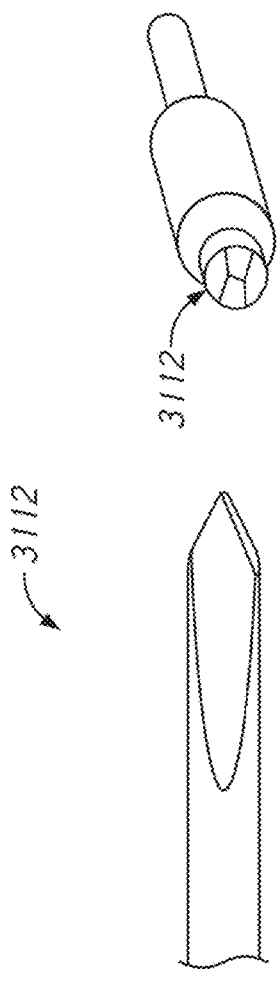
FIG. 31D illustrates a side view of the diamond style tip.

The lengths of the first, second, and third segments 2914, 2916, 2918 can vary. The taper of the third segment 2916 can have an angle of about 2° to about 5°, or greater than 5°. The second segment 2918 may have a length of between about 14 mm to about 30 mm, or between about 16 mm to about 28 mm, or between about 20 mm to about 25 mm. As shown in FIG. 29D, the first segment 2914 can be shorter and the third segment 2916 can be longer compared to the guide wire 2900 shown in FIGS. 29A-29C. As shown in FIG. 29E, the first segment 2914 can be shorter and the second and third segments 2916, 2918 can be longer. The first, second, and third segments 2914, 2916, 2918 may have generally the same or similar length, as shown in FIG. 29E. As shown in FIGS. 30A-30F, a guide wire 3000 may have a longer first segment 3014 and a shorter third segment 3016 compared to the guide wire 2900 shown in FIGS. 29A-29C. The third segment 3016 of the second portion 3008 of the guide wire 3000 can include one or more (for example, two) cutting flutes 3020. The cutting flute 3020 can facilitate insertion of the second portion 3008 of the guide wire 3000 into the bone as the outer diameter of the second portion 3008 increases from D3 to D2.

The guide wire 400 can be inserted into the bone in a facture fixation procedure via the leading end 402, which can include the sharp tip 412. Once the second portion 408 of the guide wire 400 extends through the bone, the length of the second portion 408 embedded in the bone can be measured directly or indirectly to determine the length of the implant 100 to be used so that the implant 100 does not protrude from the outer surface of the bone on either end of the implant 100.

The first portion 406 can have a length greater than the length of the implant 100 so as to slidably accommodate the implant 100 and to allow for easier manipulation of the trailing end 404 of the guide wire 400 and/or easier interface of the driver with the driver interface 118 on the trailing end 104 of the implant 100. The length of the first portion 406 can be, for example, between about 15 mm to about 60 mm, or between about 18 mm to about 60 mm, or between about 20 mm to about 60 mm, or between about 25 mm to about 60 mm, or between about 30 mm to about 60 mm, or between about 35 mm to about 55 mm, or between about 40 mm to about 45 mm. The second portion 408 can have a length greater than is sufficient to extend between opposite sides of the outer surface of the cortical wall. The length of the second portion 408 can be sufficient for easier sizing of the required implant length when the second portion 408 is inserted into the bone. The length of the second portion 408 can be, for example, between about 30 mm to about 70 mm, or between about 40 mm to about 65 mm, or between about 50 mm to about 60 mm.

The required or desired length of the implant 100 can be determined using a sizing tool, which can directly or indirectly measure the desired length of the implant 100. One example of a sizing tool is a depth gauge 500, such as illustrated in FIGS. 5A-5D. The depth gauge 500 can be made of any suitable material, for example, stainless steel, biocompatible plastic, or otherwise. The depth gauge 500 can optionally be disposable. A disposable depth gauge needs not be sterilized for re-use. The sterilization process, for example, by autoclave, may also distort the shape of the depth gauge 500, thereby making the depth gauge 500 inaccurate.

The depth gauge 500 can include a tip portion 502 and a gradated portion 504. As shown in FIG. 5, the tip portion 502 can have a smaller dimension than the gradated portion 504 in one view. For example, the gradated portion 504 can gradually taper down toward the tip portion 502. As shown in FIGS. 5B and 5C, the depth gauge 500 can have a generally uniform thickness, which can be, for example, in the range of millimeters. The length of the depth gauge 500 or a portion thereof, such as the distance of the depth gauge 500 from the free end of the tip portion 502 to a first gradation mark 506, can vary according to the length of the second portion 408 and/or a total length of the guide wire 400.

As will be described in more detail below, when in use, the free end of the tip portion 502 can be placed flush with the insertion point of the guide wire 400 on the outer surface of the bone. The depth gauge 500 can include an elongate slot 508 extending generally along a longitudinal axis CL of the depth gauge 500 for a portion of the depth gauge 500. As shown in FIGS. 5A and 5D, the slot 508 can terminate past the last gradation mark 510 near a free end of the gradated portion 504. A remainder of the guide wire 400 outside the insertion point on the bone can be aligned generally along the slot 508. The gradation mark (for example, numbers such as 48, 46, 44, etc., letters, icons, and/or the like) that aligns with the beginning of the transition portion 410 can indicate the desired length of the implant 100 (for example, in mm). As shown in FIG. 5A, instructions on how to read the measurements can be provided on the surface of the depth gauge 500 to reduce confusion about the proper way of using the depth gauge 500.

Figure 28C:
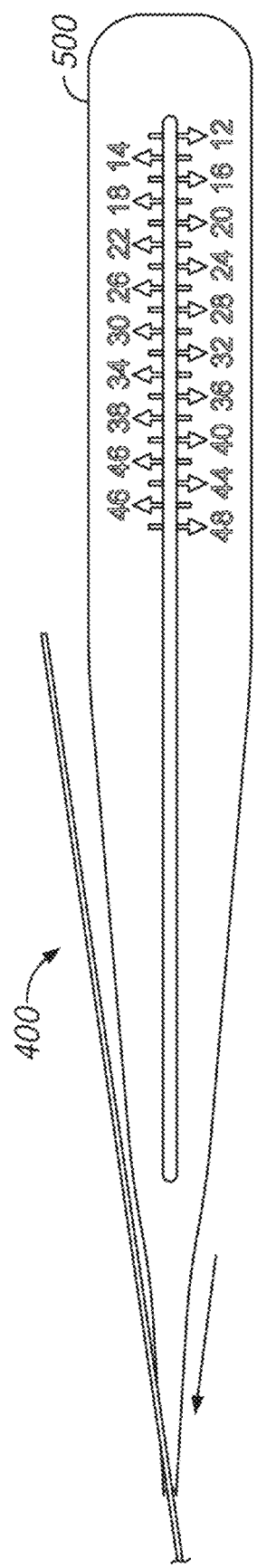
Figure 28D:
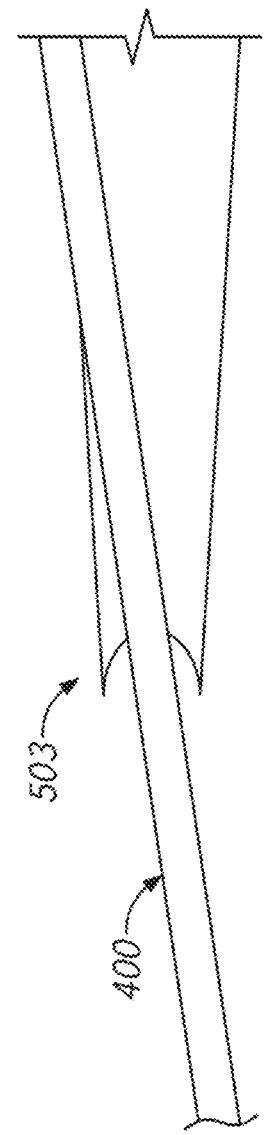

As shown in FIGS. 28A-28B, the depth gauge 500 can include a forked tip 503. The forked tip 503 can improve engagement of the depth gauge 500 with any of the guide wire examples disclosed herein by reducing sliding of the tip of the depth gauge 500 off from the guide wire, so as to improve ease of depth determination. The shape of the fork can range from a general V shape (e.g., FIG. 28A) to an arc or semicircle (e.g., FIG. 28D), and is not meant to be limiting by the examples shown in FIGS. 28A-28D.

Figure 27A:
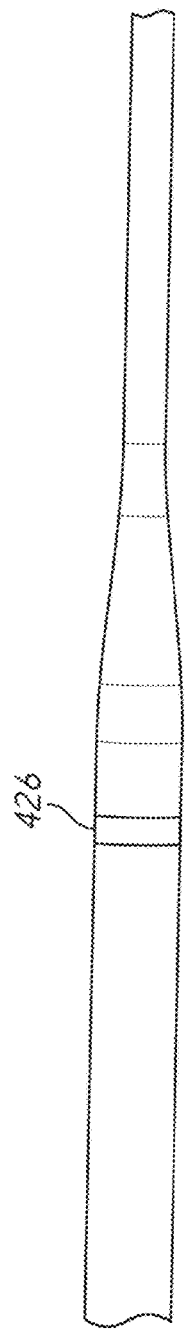
FIGS. 27A-27B illustrate an example guide wire with a laser marking configured to facilitate ease of sizing.
Figure 27B:
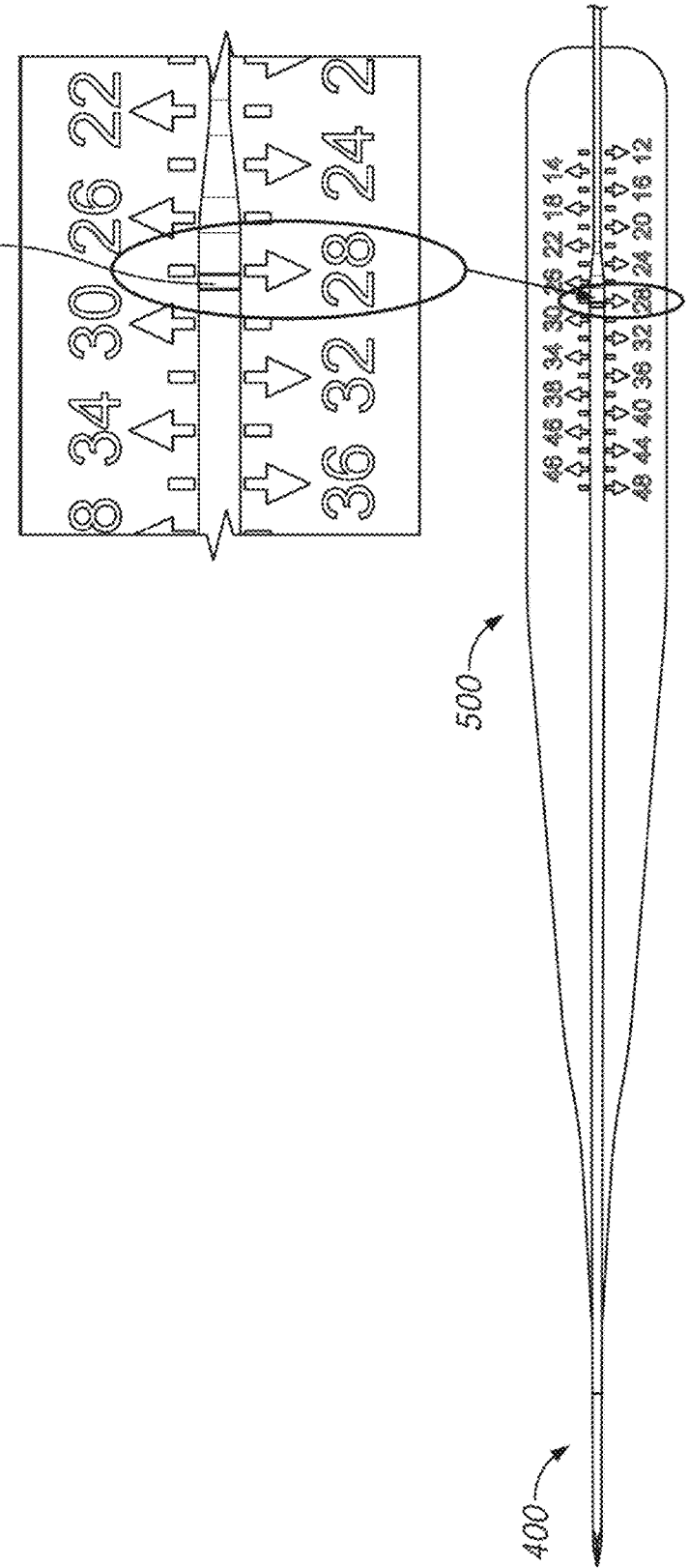

As shown in FIGS. 27A-27B, the guide wire 400 (or any other guide wire examples disclosed herein) can include a marking 426 to facilitate reading of the depth using a sizing tool, such as the depth gauge 500. The marking 426 can be a laser mark, a colored band, or any other suitable marking.

Alternatively or additionally, other types of depth gauges can be used. For example, a depth gauge similar to the depth gauge 500 can measure a distance of the guide wire 400 from the insertion point on the bone to the trailing end 404 of the guide wire 400. Such a depth gauge has a greater total length than the depth gauge 500 as shown in FIGS. 5A-5D. Alternatively, the guide wire 400 itself can include a plurality of depth marks so that a separate sizing tool may not be needed. In some configurations, the depth mark on such a guide wire and closest to the insertion point on the bone can indicate the desired length of the implant 100. In some implementations, depth marks on the portion of the guide wire embedded in the bone can be radiopaque so as to be visible when viewed using fluoroscopy.

Figure 6A:
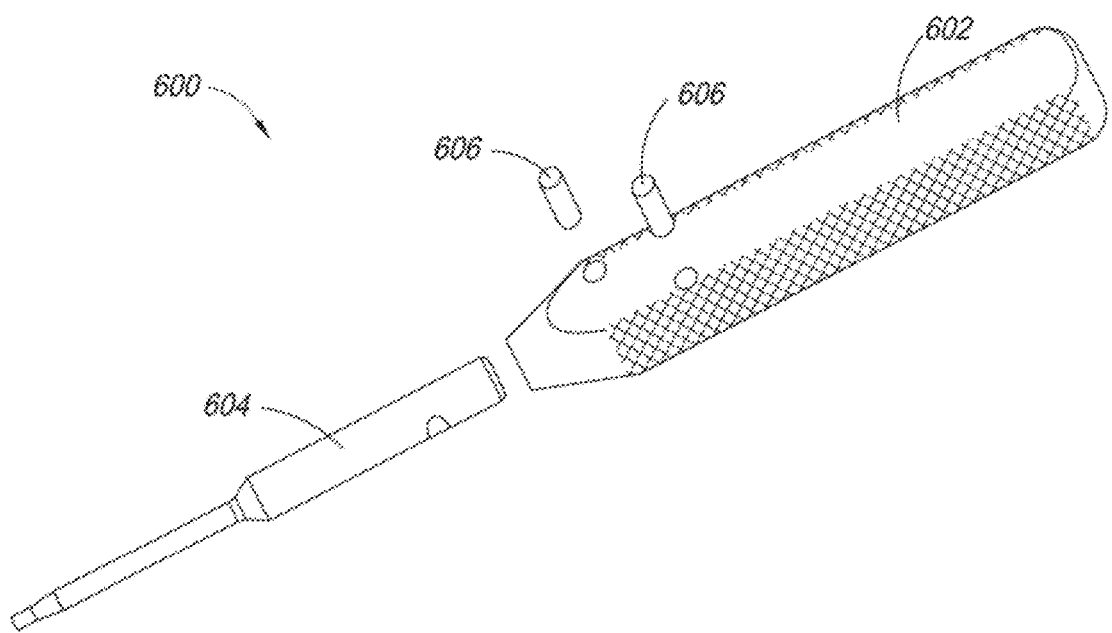
FIG. 6A illustrates an exploded view of an example driver configured to deliver the implant of FIG. 2A.
Figure 6B:
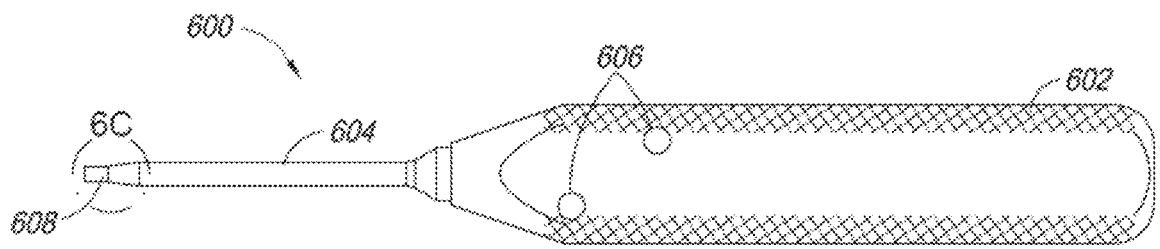
FIG. 6B illustrates a front view of the driver of FIG. 6A.

FIGS. 6A-6D illustrate an example driver 600 configured to deliver the implant 100. The driver 600 can include a driver handle 602 and a driver shaft 604. The driver handle 602 and/or the driver shaft 604 can be made of any suitable material(s), for example, stainless steel, biocompatible plastic, or otherwise. The driver shaft 604 can be coupled to the handle 602 using any suitable method, for example, via one or more dowel pins 606 as illustrated in FIGS. 6A and 6B, overmoulding, or otherwise.

Figure 6C:
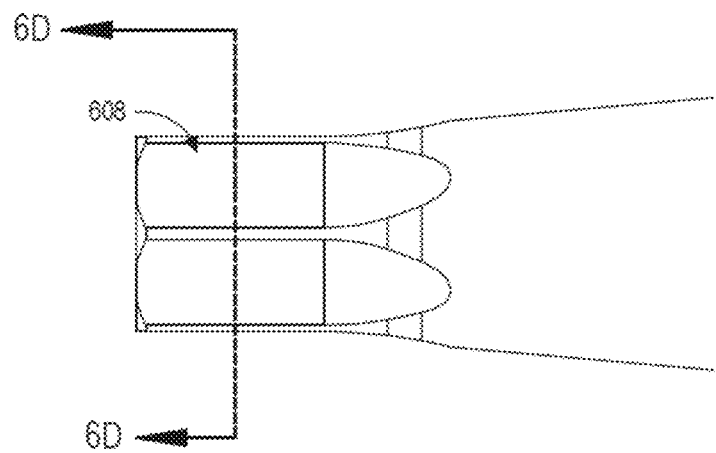
FIG. 6C illustrates a detailed view of a driver head portion of the driver of FIG. 6A.
Figure 6D:
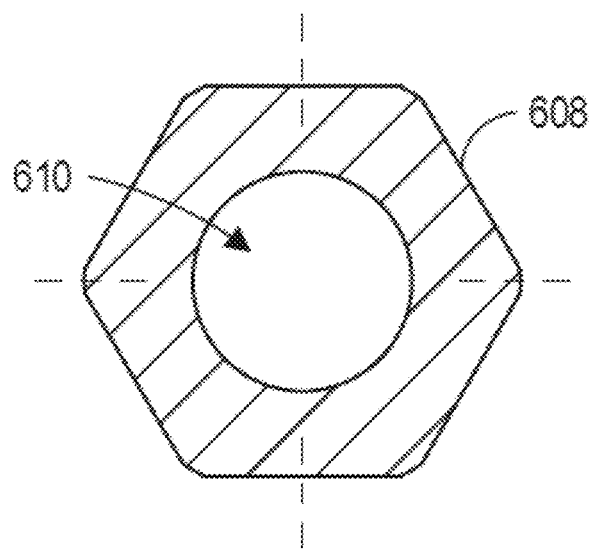
FIG. 6D illustrates a sectional view of the driver head portion in the detailed view of FIG. 6C along axis B-B.

FIGS. 6C and 6D illustrate a head portion 608 of the driver shaft 604. The head portion 608 is configured to interface with the driver interface 118 of the implant 100. In the illustrated example, the head portion 608 can be a hex head compatible with the hex head interface of the implant 100. The head portion 608 can have other configurations depending on the type of driver interface of the implant.

As shown in FIG. 6D, at least the head portion 608 of the driver shaft 604 can be cannulated. In some configurations, the driver 600 can be cannulated along its entire length or substantially its entire length. A diameter of the cannulation 610 can be configured so that, during the implant delivery procedure, the cannulation 610 can slidably receive the first portion 406 of the guide wire 400 in order to interface with the implant 100 that also slidably receives the first portion 406 of the guide wire 400. The diameter of the cannulation 610 can be, for example, the same or substantially similar as the diameter of the through-cannulation 120 of the implant 100.

Example Methods of Delivery of Intramedullary Fixation System Disclosed Herein

Certain steps of a preferred example method of delivering the implant 100, 700 (or any variations thereof based on this disclosure) are illustrated in FIGS. 8A-8F. The guide wire 400 is illustrated in FIGS. 8A-8F. However, the methods described below can be used with any of the guide wire embodiments described herein. The method is illustrated with reference to the implant 100. However, any variation of the implant described herein, for example, the implant 2600C, 2600D, 2600E, 2600F can be inserted using the method described herein.

Figure 8A:
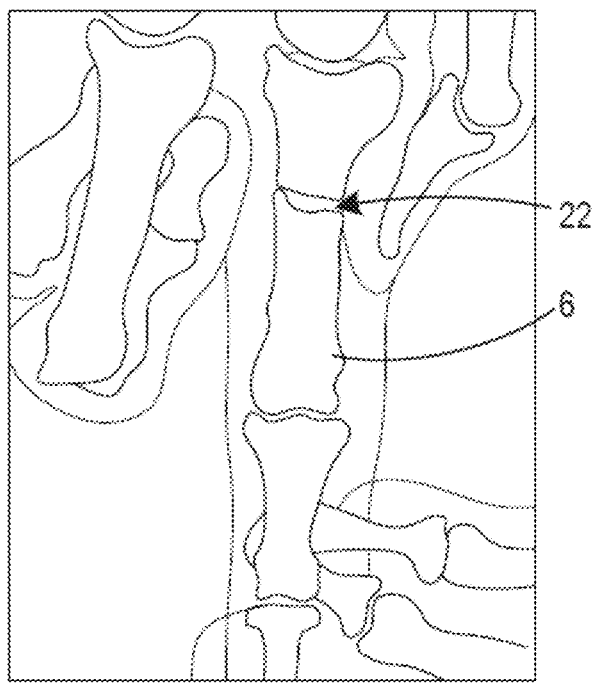
FIGS. 8A-8G illustrate certain steps of an example method of implanting the implant of FIG. 2A.
Figure 8B:
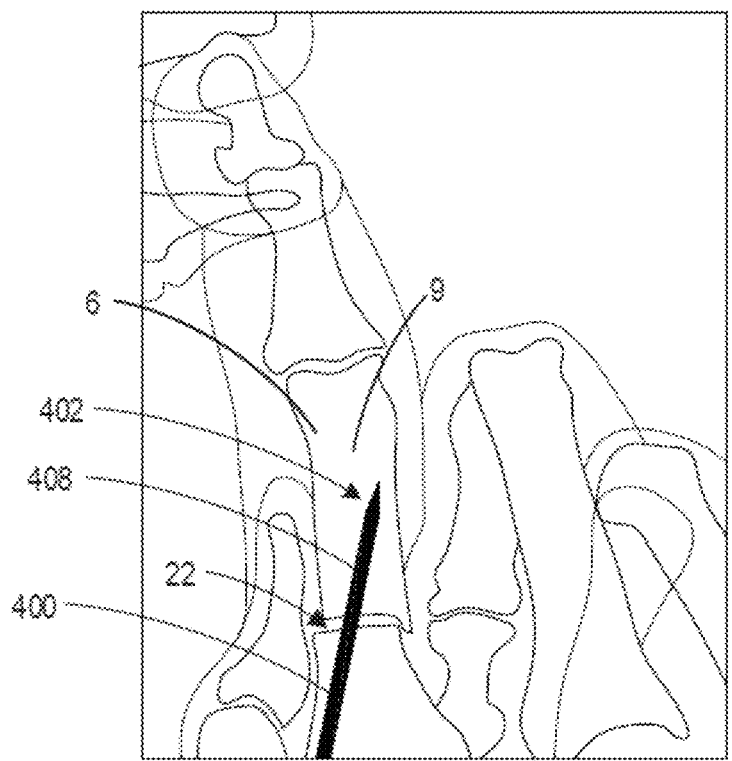

As shown in FIG. 8A, the body anatomy including the injured bone can be viewed using an imaging system, which can be fluoroscopy, for example, using a C-arm or otherwise. As shown in the x-ray image in FIG. 8A, a bone 6, which can be, for example, a phalanx, has sustained a fracture at a fracture site 22. As shown in FIG. 8B, a first guide wire 400 having at least two diameters can be inserted into a medullary canal of the bone 6 from the leading end 402. The second portion 408 of the guide wire 400 is partially inserted into the bone. The guide wire 400 can be inserted percutaneously into a non-articular base (or a non-articular surface close to the base) of the bone. The guide wire 400 can be inserted, for example, in a proximal-to-distal direction. After entering the bone 6, the guide wire 400 can cross the bone medially and laterally (or laterally and medially) and cross the fracture site 22.

Figure 8C:
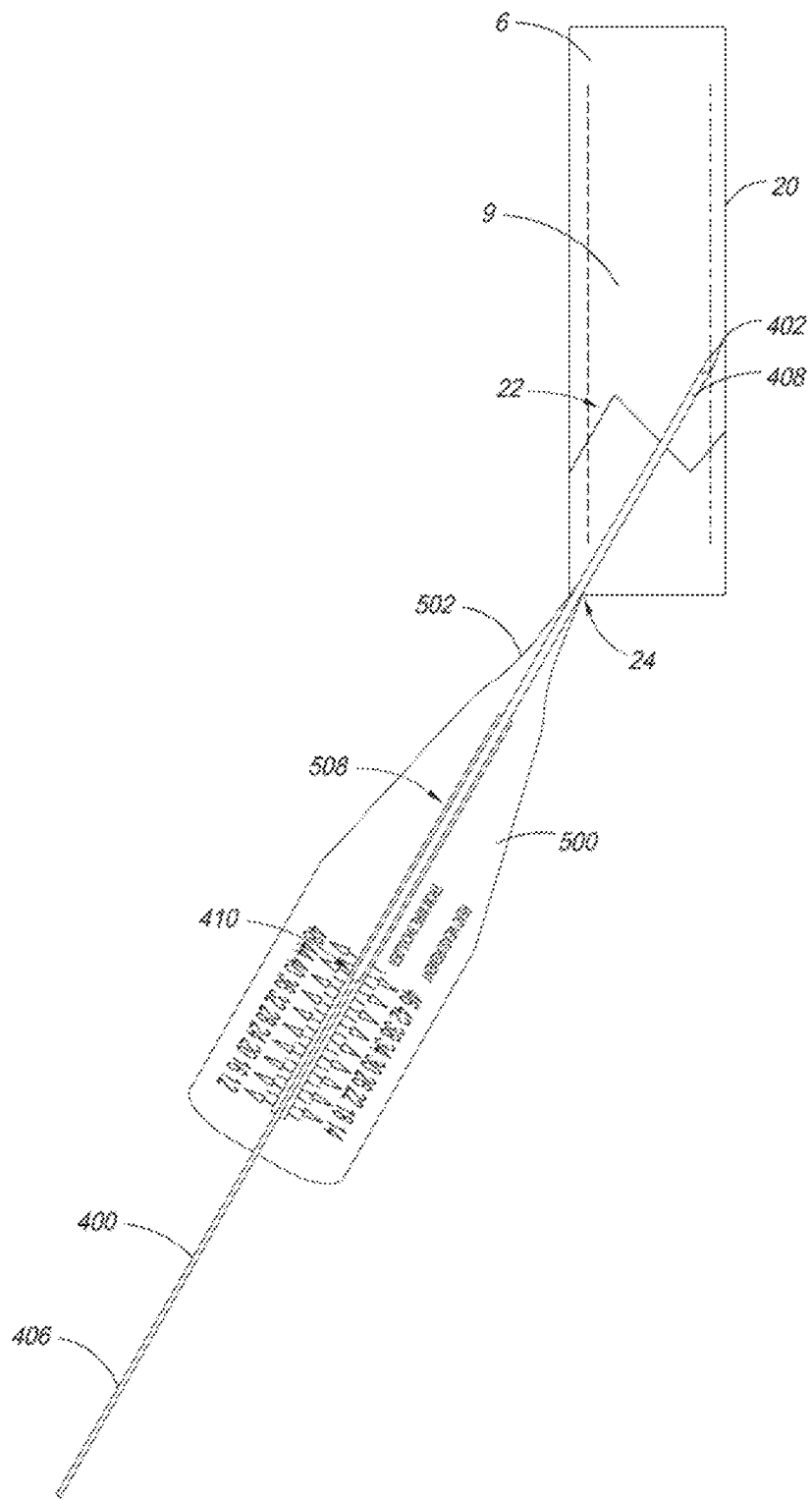

As shown in FIG. 8C, the guide wire 400 can stop being advanced when the leading end 402 of the guide wire 400 sits flush or substantially flush with, or slightly shy of, the outer surface 20 of the bone 6 on the opposite side of the medullary canal 9 from an insertion point 24. The position of the leading end 402 of the guide wire 400 in the bone 6 can be confirmed using the imaging system. The length of the second portion 408 of the guide wire 400 in the bone 6 can be measured using any suitable sizing marks, tools, or otherwise.

For example, a small incision (for example, about 2 mm or otherwise) can be made on the skin over the bone 6. The tip portion 502 of the depth gauge 500 can be inserted into the small incision. In the example shown in FIG. 8C, the free end of the tip portion 502 of the depth gauge 500 can be placed flush onto the insertion point 24 for the guide wire 400 on the bone 6. The guide wire 400 and/or the depth gauge 500 can be adjusted so that the guide wire 400 can be seen in the elongated slot 508 and runs substantially parallel to the slot 508. The gradated mark that is aligned with the transition portion 410 of the guide wire 400 can provide an indication of the desired implant length so that when implanted, the implant 100 can engage both cortical walls of the bone 6, but does not protrude from the outer surface 20 of the bone on either end of the implant 100. As shown in FIG. 8C, the transition portion 410 can be aligned to the gradation mark of 45 mm. An implant having a length of about 45 mm, or the next closest length available that does not exceed 45 mm (such as 44 mm) can be selected. After having sized the implant 100, the depth gauge 500 can be removed.

Figure 8D:
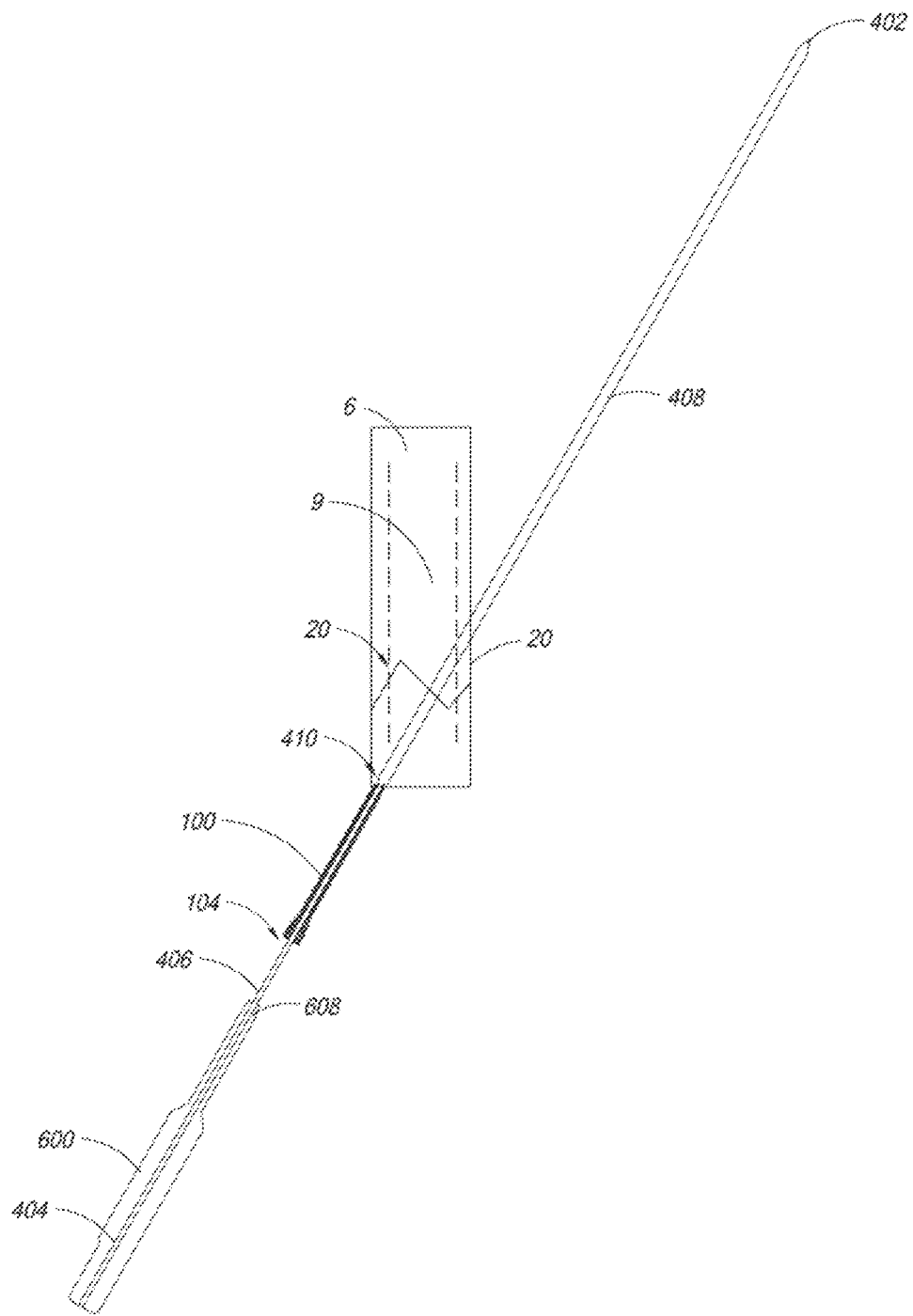

As shown in FIG. 8D, the guide wire 400 can be further advanced through the bone 6 until the transition portion 410 substantially reaches the insertion point 24 of the bone. A first cannulated implant 100 having the desired length, for example, between about 44 mm to about 45 mm in the illustrated example, can be slid onto the first portion 406 of the guide wire 400. The first implant 100 can stop advancing on the first portion 406 of the guide wire 400 when the first implant 100 reaches the transition portion 410. The at least partially cannulated driver 600 can also slide onto a remaining part of the first portion 406 of the guide wire 400 via the trailing end 404 of the guide wire 400.

The driver 600 can be advanced along the first portion 406 of the guide wire 400 until the driver head portion 608 of the driver 600 engages the driver interface of the implant 100 on the trailing end 104 of the implant 100. Alternatively, the implant 100 and the driver 600 can be removably connected prior to being advanced onto the guide wire 400. Using the driver 600, the implant 100 can be delivered through a tunnel in the bone that has been created by the second portion 408 of the first guide wire 400. The root or minor diameter of the shaft 106 of the implant 100 can be substantially the same as the outer diameter D2 (see FIG. 4B) of the second portion 408 of the guide wire 400. The second portion 408 of the guide wire 400 can therefore clear a pathway for the root or minor diameter of the shaft 106 of the implant 100. Alternatively, the outer diameter D2 can be substantially the same as the outer or major diameter D of the shaft 106 of the implant (see FIG. 3A). Due to the at least two diameters D1, D2 (see FIG. 4B) of the guide wire 400, the implant 100 can have a greater wall thickness, thus greater structural rigidity, for the length of the implant 100, while keeping the outer diameter D to be as small as slightly larger than D2 of the second portion 408 of the guide wire 400. The at least two diameters of the guide wire 400 allows the bone tunnel to be created using the second portion 408 of the guide wire 400 so that a smaller torque can be used to drive the implant 100 into the bone 6 and/or so that the insertion of the implant 100 causes little or no additional trauma to the bone 6 than the insertion of the guide wire 400. If greater resistance is felt upon insertion of the implant 100, the driver 600 can be backed out several turns (for example, about 2 turns) before resuming the insertion of the implant 100.

The implant placement can be intermittently (or continuously) confirmed over an imaging system. The thread pitch of the implant 100 can be configured so that control of the distance of advancement of the implant 100 in the bone 6 can be more fine-tuned and more accurate by rotating the driver 600 than when advancing a standard K-wire into the bone by axial advancement of a K-wire driver. The greater control by the driver 600 can further allow the implant 100 to be more precisely placed in the bone 6 and further reduce the likelihood of the leading end 102 or the trailing end 104 of the implant 100 penetrating into the tissue surrounding the bone 6.

Figure 8E:
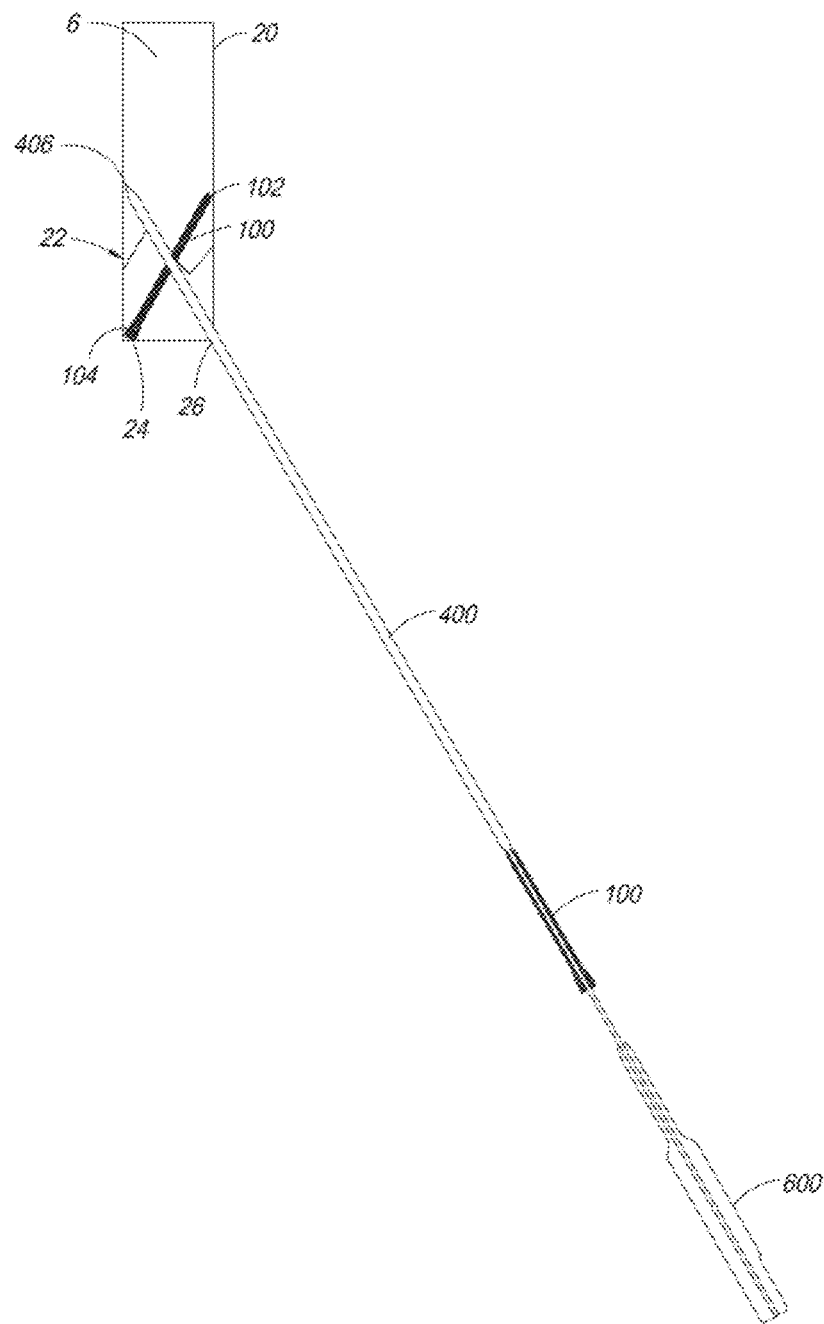

As shown in FIG. 8E, after the first implant 100 has been implanted into the bone 6 to the desired position, the first guide wire 400 can be removed from the first implant 100 and from the bone 6. For example, the first portion 406 of the first guide wire 400 can be removed distally. As D1 of the first portion 406 of the guide wire 400 is smaller than D2 of the second portion 408 of the guide wire 400, pulling the first portion 406 of the guide wire 400 out of the bone 6 does not cause any additional trauma to the bone 6.

The same steps can be repeated with the same guide wire 400 or a second guide wire 400 to deliver a second implant 100. The second implant 100 may or may not have the same length as the first implant. As shown in FIG. 8E, the second portion 408 of the same or second guide wire 400 can be inserted at a different insertion point 26 on the non-articulating base of the bone 6 in a direction so that the guide wire 400 can cross the first implant 100 and that its leading end 402 can terminate on the cortical wall opposite to the cortical wall engaged by the leading end 102 of the first implant 100.

Confirmation can be made that the guide wire 400 and the first implant 100 are separated by a minimum distance so as to ensure that when the second implant 100 is implanted via the guide wire 400 as shown in FIG. 8E, the thread on the second implant 100 does not make contact with the outer surface of the first implant 100. This is because such contact during the insertion of the second implant 100 can cause higher torque values to be transmitted to the driver 600, thereby resulting in failure of the driver 600.

Figure 8F:
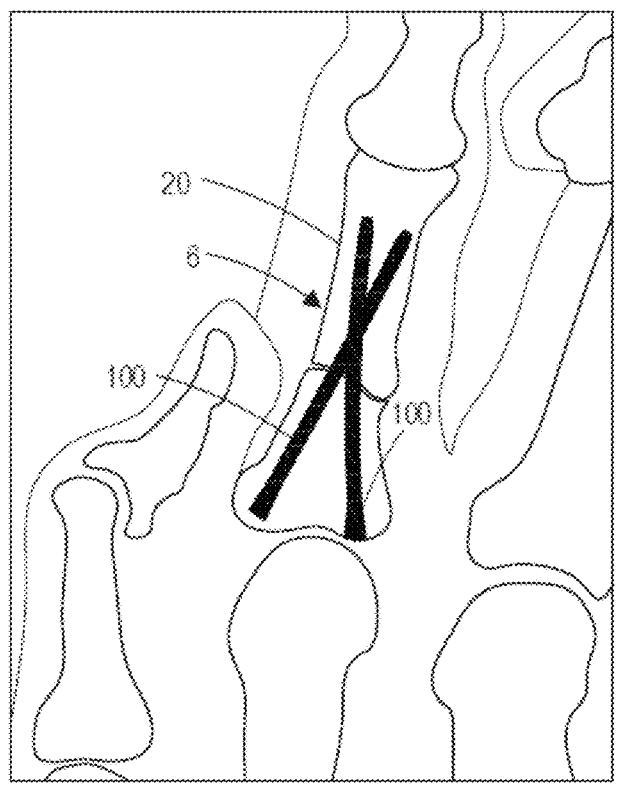
Figure 8G:
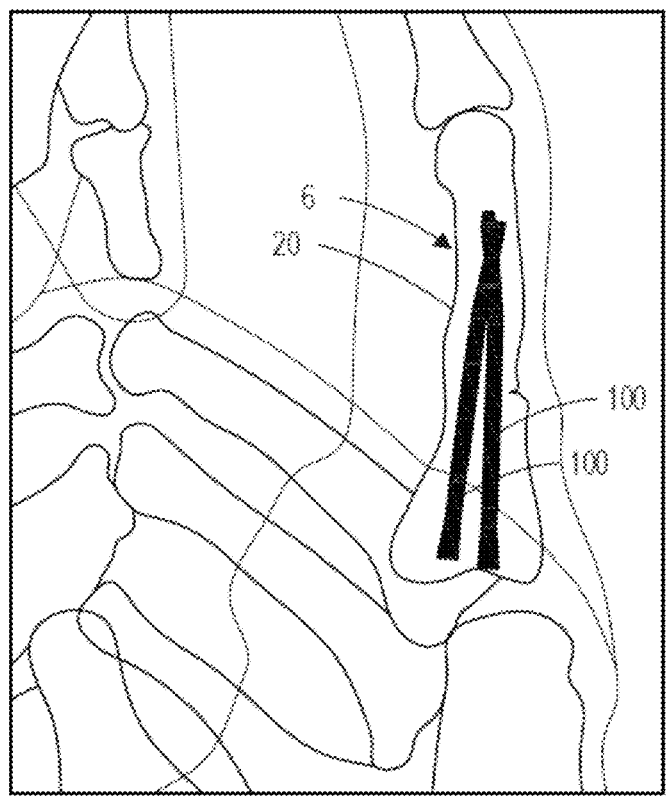

After the second implant 100 has been implanted into the bone 6 to the desired position, the same or second guide wire 400 can be removed from the second implant 100 and from the bone 6 as described above. FIGS. 8F and 8G illustrate x-ray images of the implanted cross-pinned first and second implants 100. FIG. 8F illustrates an approximately x-shaped construct of the two implants. FIG. 8G illustrates an approximately v-shaped construct of the two implants. The ends of neither implant 100 sits proud of the outer surface 20 of the bone 6 so as to avoid interaction with the tissue surrounding the bone 6. The first and second implants 100 are crossed to improve rotation control of the fractured parts of the bone relative to each other.

The cannulated implant 100 delivery method using the guide wire 400 having at least two diameters can also benefit from adopting some of the similar techniques as cross-pinning of the standard K-wires described above. Surgeons likely have already been trained and are familiar with the cross-pinning technique, making the systems and methods disclosed herein safer and more efficiently performed. However, the fixation systems and methods disclosed herein further improve cross-pinning of standard K-wires, for example, by allowing more accurate sizing of the implants, reducing implant displacement post-surgery, and providing the other advantages disclosed herein.

The implants 100 can also be implanted using different delivery methods, such as shown in FIGS. 9A-9H. The alternative method can include any of the relevant steps described above, for example, imaging the bone, the implant 100, and/or the delivery instruments including the guide wire 400, inserting the guide wires 400, sizing the implant 100, and/or inserting the first and second implants 100 using the guide wires 400. Features in the description of FIGS. 9A-9H can also be incorporated into the method described above.

Figure 9A:
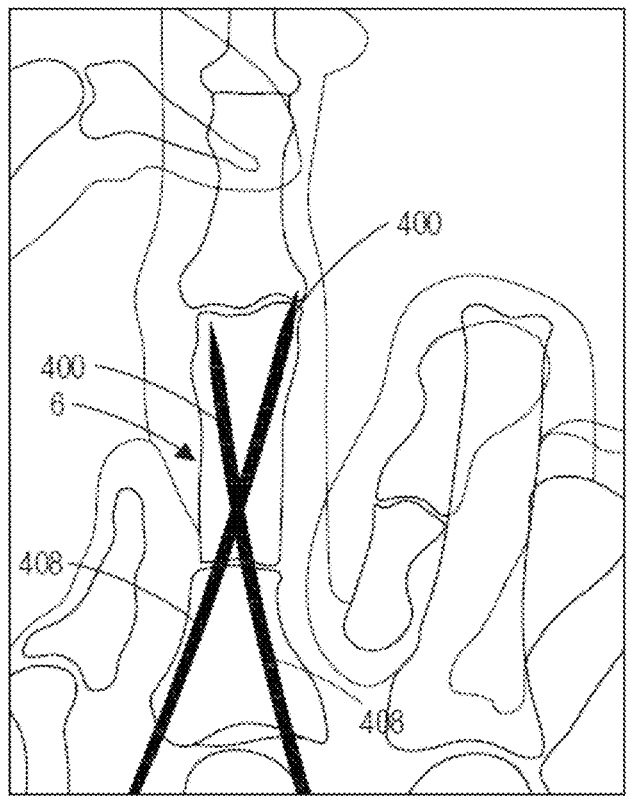
FIGS. 9A-9F illustrate certain steps of another example method of implanting the implant of FIG. 2A.
Figure 9B:
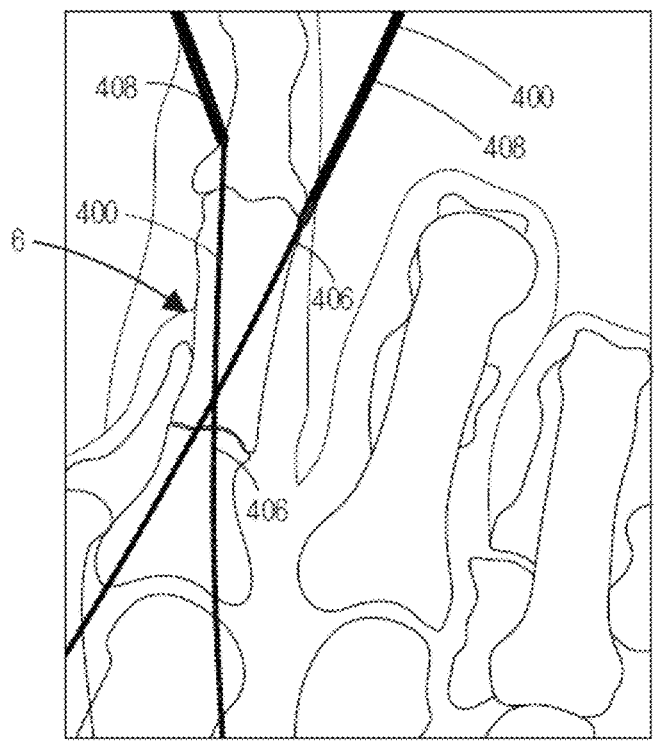

As shown in FIG. 9A, an alternative implantation procedure can include insertion of a first guide wire 400 having at least two diameters and a second guide wire 400 having at least two diameters in a cross pattern prior to inserting either implant 100. A predetermined distance between the second portions 408 of the first and second guide wires 400 can be confirmed using an imaging system to reduce the likelihood of the two implants 100 contacting each other during insertion. As shown in FIG. 9B, the second portions 408 of the guide wires 400 can be pulled out of the bone 6 so as to leave the first portions 406 of the guide wires 400 in the bone in the tunnels created by insertion of the second portions 408.

Figure 9C:
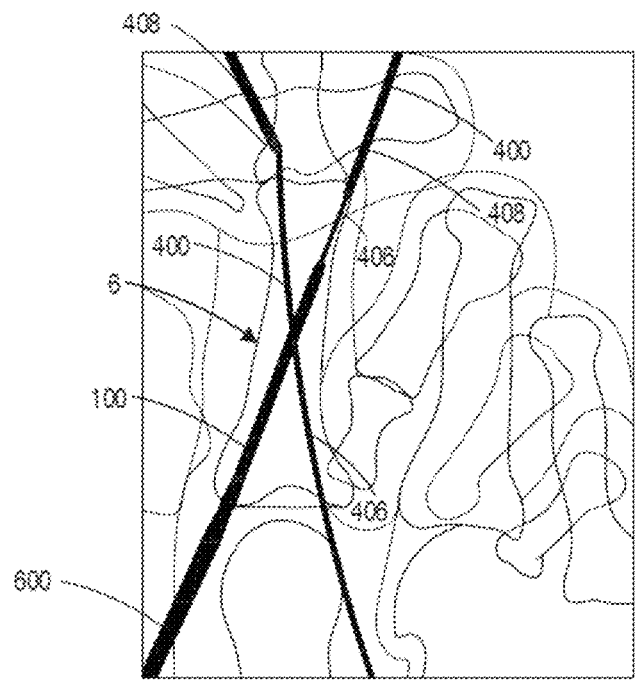
Figure 9D:
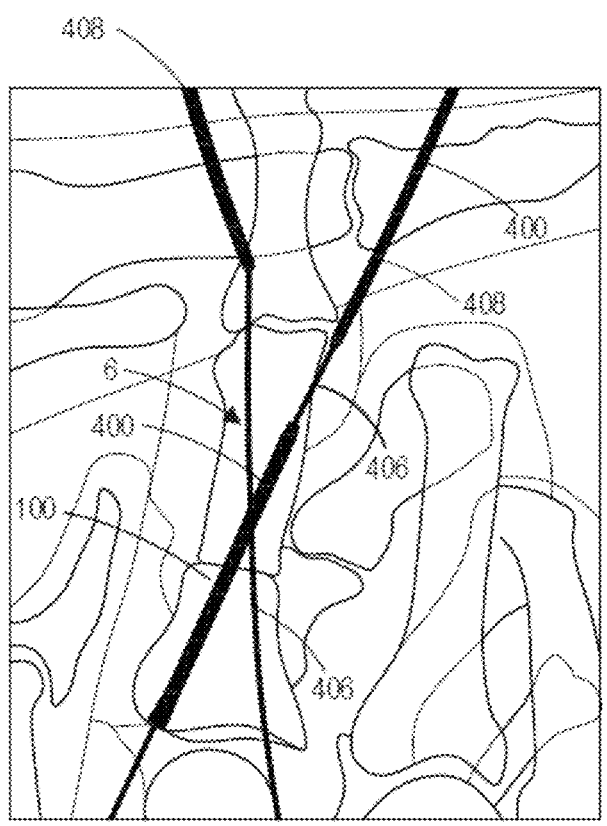
Figure 9E:
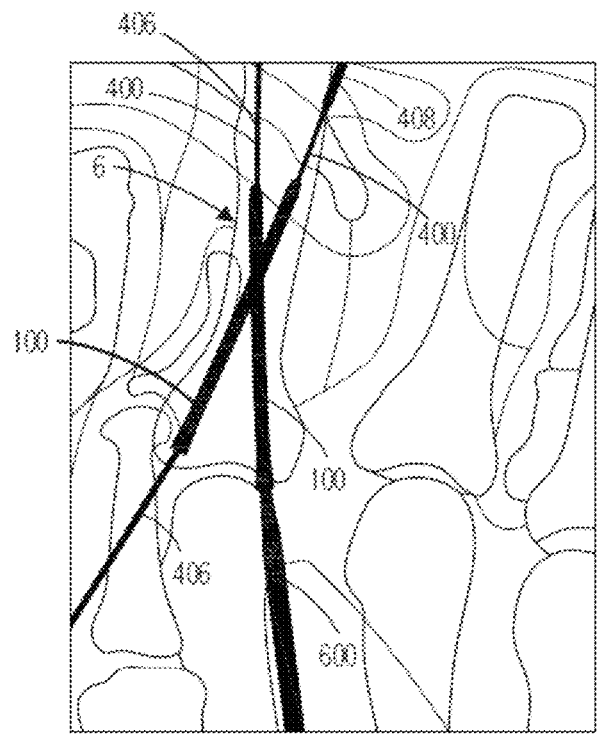
Figure 9F:
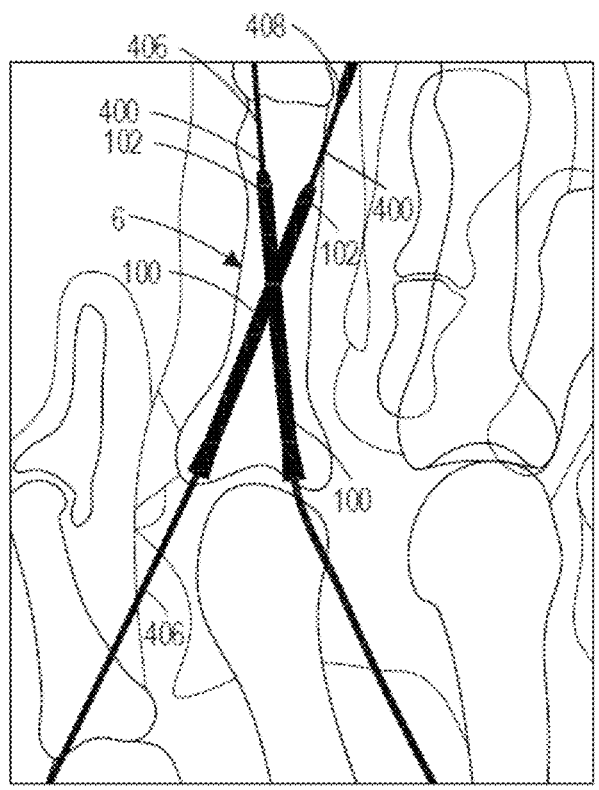

As shown in FIG. 9C, the first implant 100 can be inserted by the driver 600 into the bone tunnel created by the second portion 408 of the guide wire 400, guided by the first portion 406 of the guide wire 400. As shown in FIG. 9D, the driver 600 can be removed after the first implant 100 has been delivered to the desired position. FIGS. 9E and 9F illustrate repeating the steps of FIGS. 9C and 9D to insert the second implant 100 guided by the second guide wire 400. Once both implants 100 are delivered to their respective desired positions, the first and second guide wires 400 can be removed from the first and second implants 100 and from the bone 6.

Alternatively, after the step shown in FIG. 9A, the first and second guide wires 400 can be further advanced into the bone until the transition portions 410 of the first and second guide wires 400 are next to the insertion points on the bone, similar to the step shown in FIG. 8D for a single guide wire 400. The first and second implants 100 can then be inserted into the bone along with the first portions 406 of the first and second guide wires 400 as described above.

Figure 10:
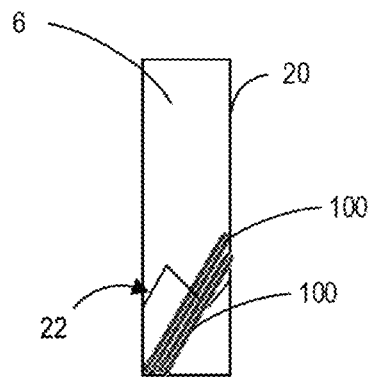
FIG. 10 illustrates schematically another example method of implanting the implant of FIG. 2A.

As another alternative, such as shown in FIG. 10, a first implant 100 and a second implant 100 can be inserted into a bone 6 with a fracture 22 so that the first and second implants 100 are substantially parallel with each other. Neither end of the first implant 100 or the second implant 100 protrudes from the outer surface 20 of the bone 6. The first and second implants 100 may or may not have the same length. This method can incorporate any of the steps of the above-described methods. For example, the first and second implants 100 can be inserted using one or more guide wires, such as the guide wire 400 disclosed herein. If a separate guide wire is used for each implant 100, the guide wires can be both inserted into the bone 6, substantially parallel to each other, prior to insertion of the first and second implants 100 guided by the guide wires. Alternatively, the second guide wire can be inserted after the insertion of the first implant 100 guided by the first guide wire. The first guide wire can be removed or can stay in the bone 6. The second guide wire can be inserted substantially parallel to the implanted first implant 100. Alternatively, two or more implants 100 may be inserted in the bone of a patient at any orientation with respect to each other using the methods disclosed herein.

Figure 11A:
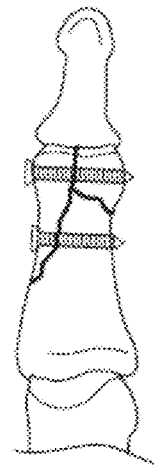
FIGS. 11A-11C illustrate schematically example lag screw fixations for various metacarpal or phalanx fractures.
Figure 11B:
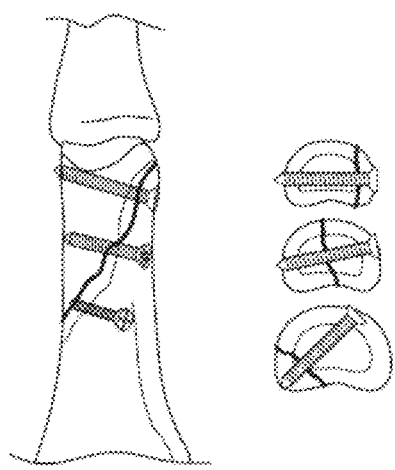
Figure 11C:
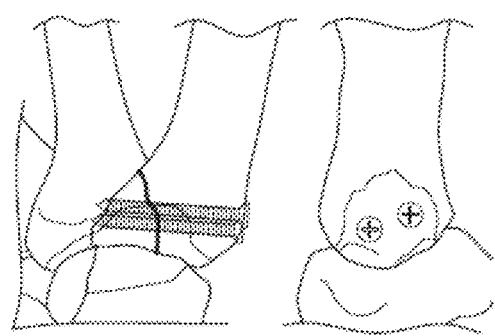

Example Methods of Delivery of A Lag Screw Using Surgical Instruments Disclosed Herein The surgical instruments described above can alternatively or additionally be used to deliver different other types of implants, for example but not limited to lag screws. One or more lag screws and the lag technique can compress fracture bone fragments together to achieve fixation and promote healing at the fracture site. Lag screws can be used for various types of factures, including but not limited to avulsion fixation, mallet fracture fixation, distal uni/bicondylar fixation, spiral/oblique fixation, Rolando fracture fixation, and Bennett's fracture fixation. Lag screws can be used for fixing different types of bones, such as a phalanx illustrated in FIGS. 11A-11B and a metacarpal illustrated in FIG. 11C. The methods below are described with the guide wire 400 as an example. However, the methods described below can be used with any of the guide wire embodiments described herein.

Figure 12A:
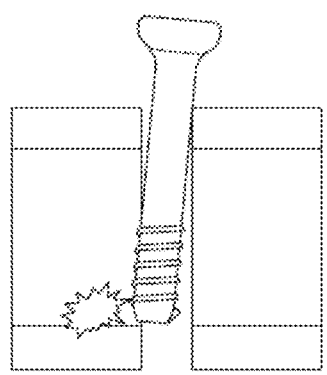
FIGS. 12A-12D illustrate example challenges for a conventional lag screw implantation procedure.
Figure 12B:
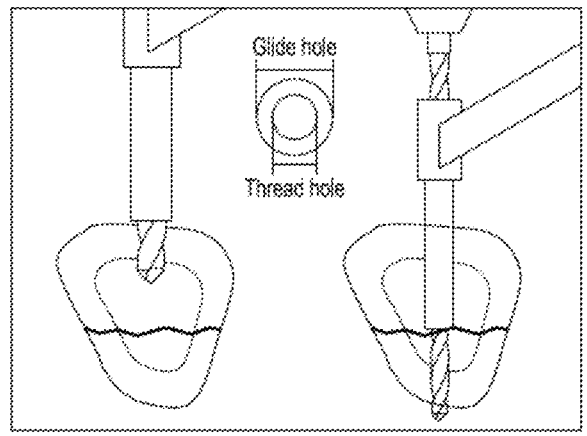
Figure 12C:
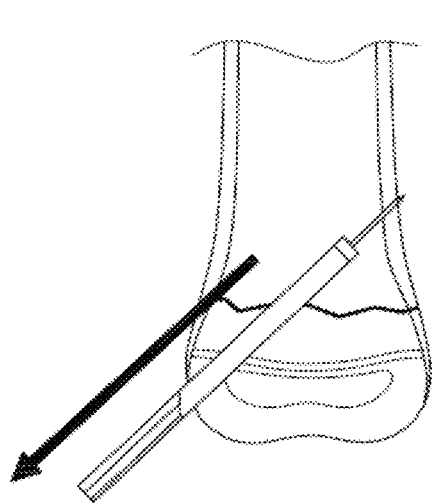
Figure 12D:
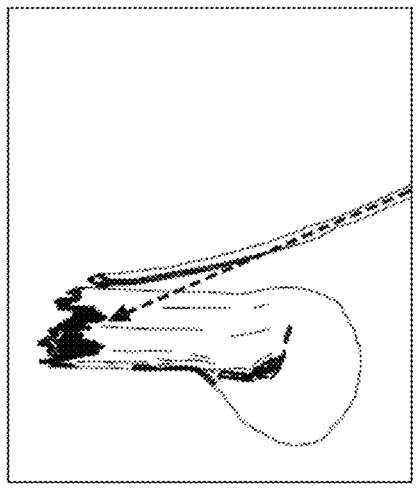

Conventional lag screw implantation techniques may involve pre-drilling through a near cortex and a far cortex of the bone using a reamer. As the screw is tightened, the threads on the terminal end of the screw engages the far cortex and the head of the screw engages the near cortex, compressing the fracture fragments together. In addition to requiring a dedicated reamer to create a bone tunnel, conventional lag screw implantation techniques may have a few other challenges. As shown in FIG. 12A, when inserting a lag screw (without being cannulated) through the bone tunnel created by a bone reamer, it can be difficult for a surgeon to find the far cortex with the tip of the lag screw. As shown in FIG. 12B, a glide hole is required if the lag screw is threaded substantially throughout its shaft length. The step of creating the glide hole is also referred to as overdrilling. As shown in FIG. 12B, the near cortex is overdrilled, using a first reamer, to the major outer diameter of the screw shaft to create the glide hole before the far cortex is drilled using a second and smaller-sized reamer to a diameter that is similar to the minor diameter of the screw shaft. When the screw is inserted, the screw glides through the glide hole and the threads only engage the far cortex through the thread hole. Overdrilling is an extra drilling step and can make the implantation procedure more complicated. The additional step can also increase the risks of iatrogenic injuries or wounds. As shown in FIG. 12C, if a cannulated lag screw is used, a conventional K-wire is first inserted through the near and far cortices before the reamer is introduced. However, the K-wire may be pulled or slip out in the direction shown by the arrow during the procedure (such as when the first reamer for overdrilling is removed) and need to be reintroduced, which can complicate the procedure. Moreover, as shown in FIG. 12D, due to the small outer diameter of a conventional K-wire as discussed above, the K-wire may bend during insertion into the bone and be difficult to use to introduce a cannulated lag screw.

Figure 13:
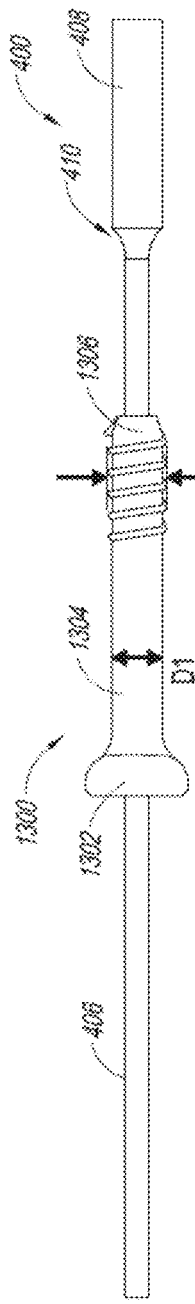
FIG. 13 illustrates an example lag screw coupled to the stepped guide wire disclosed herein.

Using the surgical instruments disclosed herein, in particular, the guide wire 400 of FIGS. 4A-4C, to deliver a lag screw can address some of the challenges discussed above and other challenges. As shown in FIG. 13, an example lag screw 1300 can be delivered using the guide wire 400. The lag screw 1300 can be made of stainless steel, titanium, hard plastic, or otherwise. The lag screw 1300 can include a head 1302 and a shaft 1304. The head 1302 can be a hex drive head or otherwise. The head 1302 can have a greater outer or major diameter than the shaft 1304. The shaft 1304 can have a minor diameter D1. The shaft 1304 can be threaded at its terminal portion 1306. In some embodiments, the shaft 1304 can be fully threaded. The terminal portion 1306 can have a major diameter D2. The lag screw 1300 can be cannulated such that the screw 1300 can slide onto the first portion 406 of the guide wire 400. The outer diameter of the first portion 406 of the guide wire 400 can be, for example, about 0.6 mm or any other values disclosed herein. The minor diameter D1 of the shaft 1304 of the lag screw 1300 can be substantially the same as the outer diameter of the second portion 408 of the guide wire 400. As will be described with reference to FIGS. 14A-14E below, a pathway of the minor diameter D1 of the shaft 1304 of the lag screw 1300 can be prepared by the second (that is, larger diameter) portion 408 of the guide wire 400. D1 of the screw 1300 and/or outer diameter of the second portion 408 the can be, for example, about 1.1 mm. The outer diameter of the threads of the screw 1300 can be greater than 1.1 mm, for example, about 1.5 mm. The length of the screw 1300 can be between about 6 mm to about 22 mm, or between about 7 mm to about 21 mm, or between about 8 mm to about 20 mm, or between about 9 mm to about 19 mm, or between about 10 mm to about 18 mm, or otherwise. The screw 1300 can be available in different lengths.

Certain steps of an example method of delivering the lag screw 1300 (or any other lag screws) are illustrated in FIGS. 14A-14E. This method does not include the use of a cannulated drill like in a conventional cannulated lag screw implantation procedure. No predrilling before introducing the guide wire 400 into a bone 6 is required, whereas most conventional cannulated screw systems require use of a guide wire and a separate cannulated drill. Even though some systems may eliminate the cannulated drilling step through use of cutting flute features on the leading end of a screw such that the screw is self-drilling or self-tapping, those systems are still limited to a K-wire with a very small diameter for initial targeting. As the cannulated screw slides over and is guided by the K-wire during insertion into the bone, the outer diameter of such a K-wire is limited by the size of the cannulation of the screw. And as described above, a K-wire with a small diameter may deflect or bend during insertion into the bone, and thus may be hard to use for initial targeting. In comparison, the guide wire 400 includes a second portion 408 with a greater outer diameter at the leading end 402 (and clears a pathway for the screw). The outer diameter of the second portion 408 is greater than the size of cannulation of the screw. The second portion 408 is stiffer and more easily inserted into bone, with less bending than a conventional K-wire. A screw can then slide onto the first portion 406 of the guide wire 400 with a smaller outer diameter to be inserted into the bone.

Figure 14A:
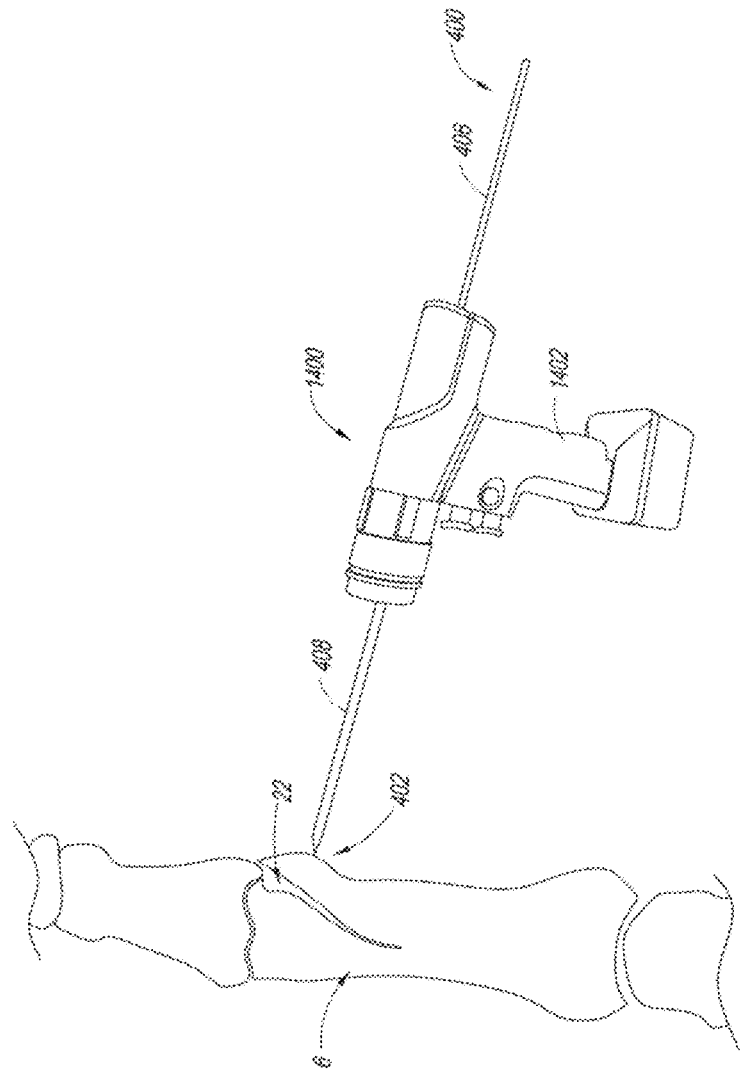
FIGS. 14A-14E illustrate certain steps of an example method of implanting a lag screw of FIG. 13.

As shown, the bone 6, which can be, for example, a phalanx, has sustained a fracture at a fracture site 22. The guide wire 400 can be inserted into the bone 6 from the leading end 402. The insertion of the guide wire 400 can be aided by a suitable guide wire driver 1400. The guide wire driver 1400 shown in FIGS. 14A, 14C, and 14D are for illustration purpose only and is not limiting. The guide wire driver 1400 can include a handle 1402 for a user's hand to facilitate pushing and/or pulling of the guide wire 400. The guide wire driver 1400 can include a collet or collet system to grab onto the second portion 408 of the guide wire 400. The guide wire driver 1400 may not need to have a specialized collect or collet system for grabbing the thinner first portion 406 of the guide wire 400. The thinner first portion 406 may be too small to be engaged an off-the-shelf collet.

Figure 14B:
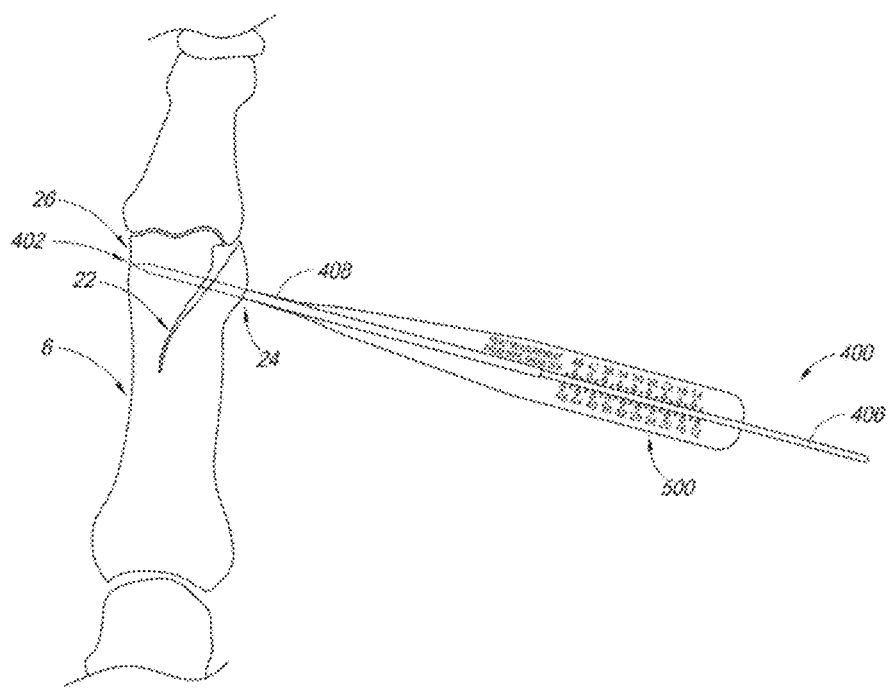
Figure 14C:
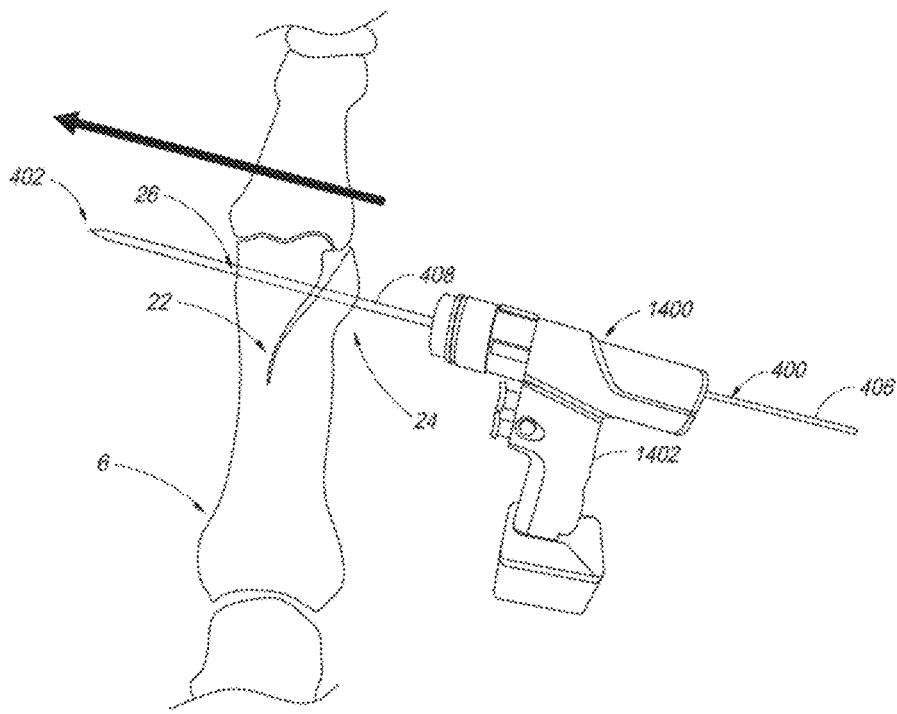
Figure 14D:
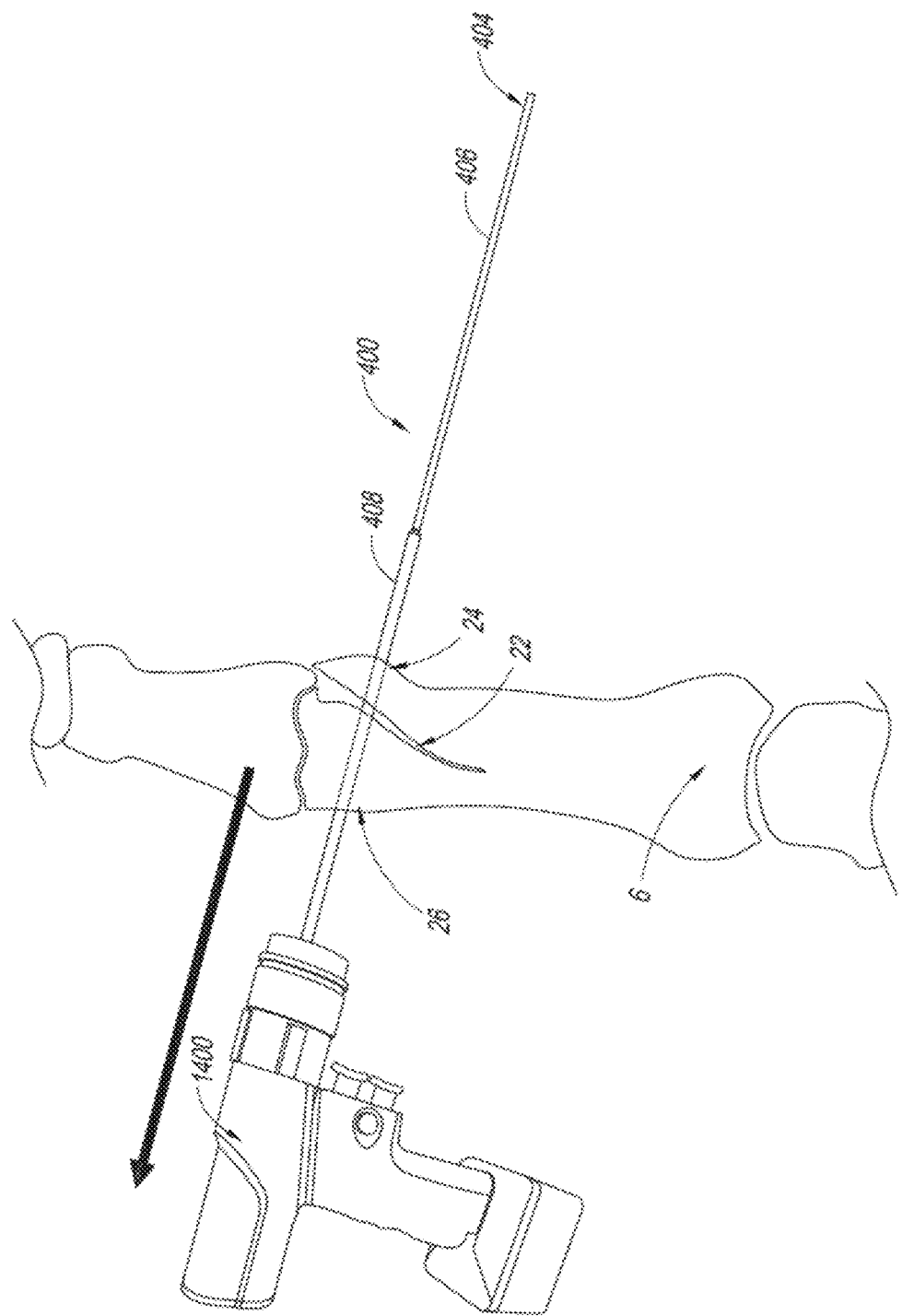

As shown in FIG. 14B, the second portion 408 of the guide wire 400 can be partially inserted into the bone 6 to a desired final implant depth, at least penetrating a near cortex 24 of the bone 6. As shown in FIG. 14B, the leading end 402 of the guide wire 400 can be just about to penetrate the bone surface at the far cortex 26. The position of the leading end 402 of the guide wire 400 in the bone 6 can be confirmed using an imaging system. The guide wire driver 1400 can be temporarily disengaged from the guide wire 400 and the depth gauge 500 described above with reference to FIG. 8C can be used to determine the desired length or size of the lag screw. After having sized the lag screw, the depth gauge 500 can be removed. The length of the second portion 408 of the guide wire 400 in the bone 6 can be measured using any suitable sizing marks, tools, or otherwise. As shown in FIG. 14C, the guide wire driver 1400 can re-engage the guide wire 400 to continue advancing the leading end 402 of the guide wire 400 in the direction of the arrow through the far cortex 26 of the bone.

As shown in FIG. 14D, the guide wire driver 1400 can be disengaged from the second portion 408 of the guide wire 400 at the side of the near cortex 24 and re-engage the second portion 408 of the guide wire 400 at the side of the far cortex 26 of the bone 6. The guide wire driver 1400 can be pulled away from the bone 6 so as to pull the guide wire 400 to pull the first portion 406 of the guide wire 400 towards the near cortex 24 of the bone 6.

Figure 14E:
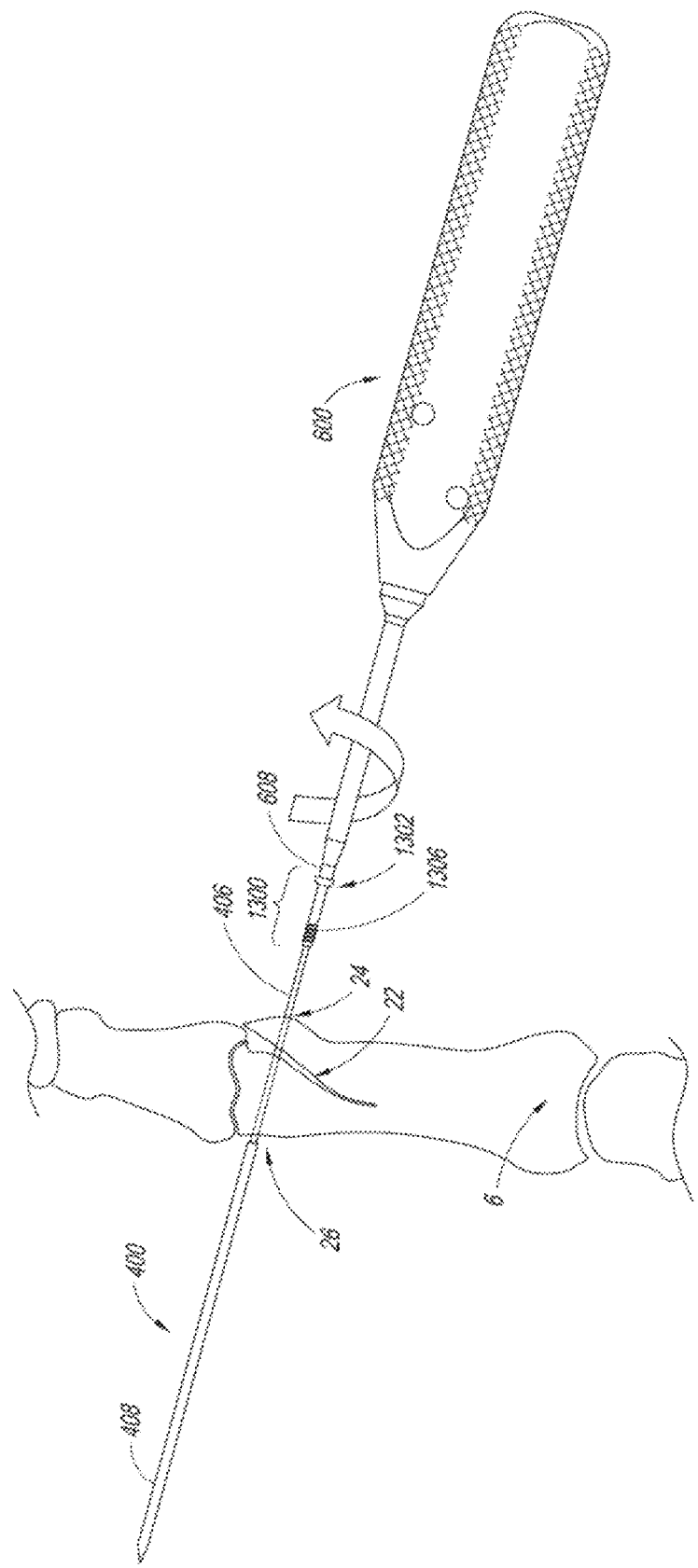

As shown in FIG. 14E, the guide wire driver 1400 can be pulled away from the bone 6 so as to pull the guide wire 400 until the first portion 406 of the guide wire 400 enters the bone 6 from the near cortex 24. The guide wire driver 1400 can be removed from the guide wire 400. A lag screw 1300 having the desired length as determined using the depth gauge or otherwise can be slid onto the first portion 406 of the guide wire 400. The at least partially cannulated driver 600 as described above can slide onto a remaining part of the first portion 406 of the guide wire 400 via the trailing end 404 of the guide wire 400. The driver 600 can be advanced along the first portion 406 of the guide wire 400 until the driver head portion 608 of the driver 600 engages the driver interface of the lag screw 1300 on the head 1300 of the lag screw 1300. Alternatively, the lag screw 1300 and the driver 600 can be removably connected prior to being advanced onto the first portion 406 of the guide wire 400. As described above, the minor diameter of the shaft 1304 of the lag screw 1300 can be substantially the same as the outer diameter of the second portion 408 of the guide wire 400. Using the driver 600, the lag screw 1300 can be delivered through a tunnel in the bone that has been created by the second portion 408 of the first guide wire 400. The threaded terminal portion 1306 of the screw 1300 can engage the far cortex 26 and the head 1302 of the screw 1300 can engage the near cortex 24 to compress the fracture fragments together. The screw placement can be intermittently (or continuously) confirmed using an imaging system. The screw 1330 can alternatively be driven into the bone 6 using a different driver than the driver 600 in FIG. 14E.

Using the instruments including at least the guide wire 400 to deliver the lag screw 1300, such as shown in FIGS. 14A-14E, can eliminate the pre-drilling step and the need for a separate reamer (or drill), and/or the need for a special collet for a K-wire driver to engage a conventional K-wire, which has a small outer diameter (for example, smaller than about 0.7 mm). The delivery method shown in FIGS. 14A-14E can eliminate pull-out of the K-wire, especially after overdrilling when switching to a different sized reamer, and maintain reduction of the bone by keeping the guide wire 400 in place while advancing the screw 1300. Moreover, the larger diametered second portion 408 of the guide wire 400 can be stiffer, less prone to bending, and easier to insert into the bone 6 than a convention K-wire with a smaller outer diameter.

Figure 15:
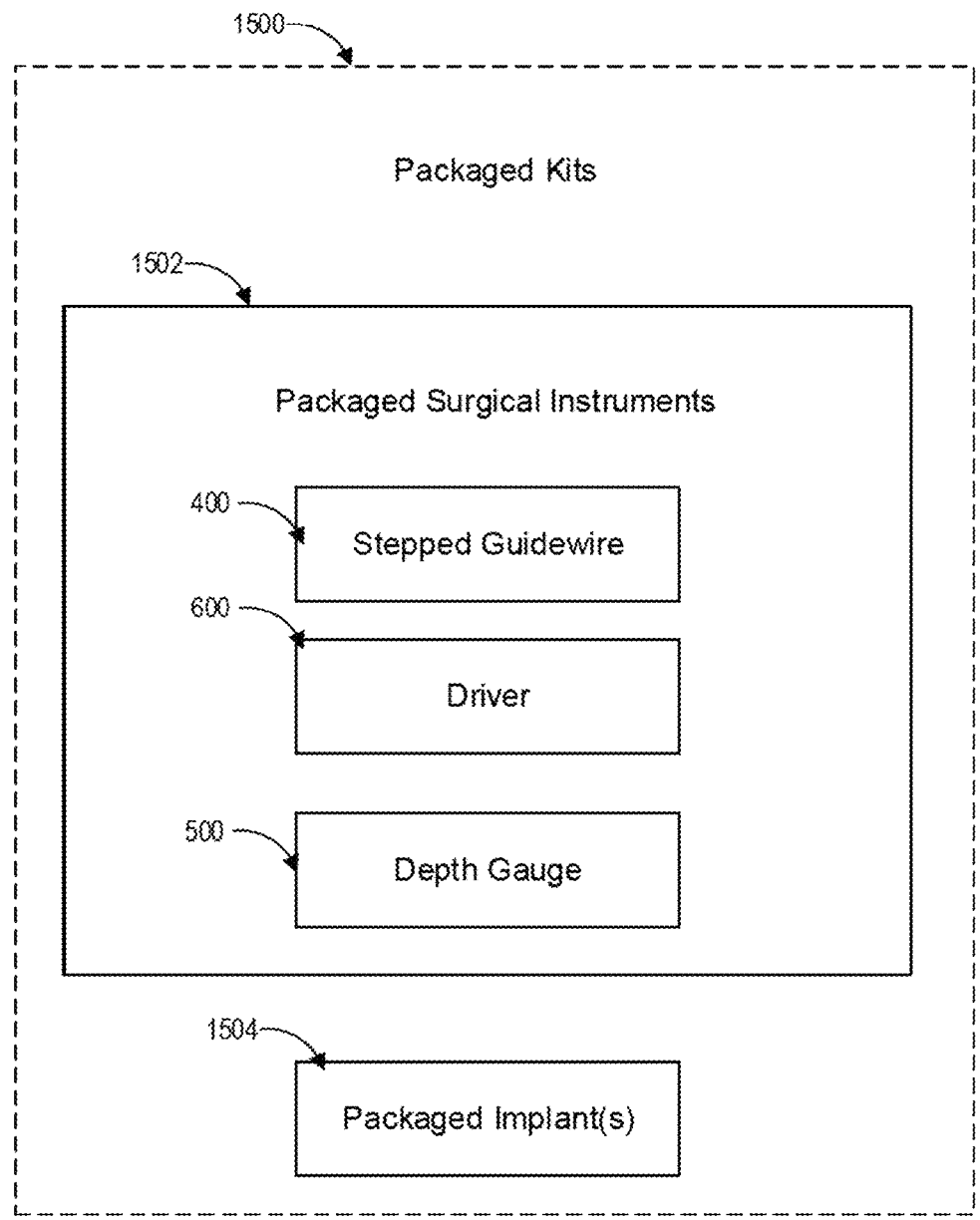
FIG. 15 illustrates schematically example packaging of the implants and surgical instruments disclosed herein.

The elimination of the need for a reamer or drill, which is typically reusable and sterilized after each use, allow the surgical tools and/or the screws or any other implants disclosed herein to be prepackaged into sterile (and optionally disposable or single-use) kits. As shown in FIG. 15, the packaged kits 1500 can include a sterile surgical instrument package 1502 and a sterile implant package 1504. The sterile surgical instrument package 1502 can include the guide wire 400, the driver 600, and the depth gauge 500. The guide wire 400, the driver 600, and/or the depth gauge 500 can be for single use or for re-use. To re-use the guide wire 400, the driver 600, and/or the depth gauge 500, these instruments can be re-sterilized after each use.

The stepped or dual-diameter guide wire, such as the guide wire 400 in FIGS. 4A-4C, or the guide wire examples in FIGS. 29A-32B, can provide flexibility in the surgical technique according to user (for example, surgeon) preference. For example, in Jones fracture fixation or another fracture fixation procedure, users may like the cannulated technique, but prefer solid screws for increased implant strength. Having a stepped guide wire with a larger diameter leading end that prepares for an implant pathway with a connected smaller diameter trailing end that allows insertion of a cannulated device can allow for both a solid and cannulated technique. For a solid technique, the solid screw may include a small recess and/or be partially cannulated at the leading end for interaction with the thinner portion of a dual-diameter guide wire disclosed herein. Furthermore, the stepped guide wire can provide the ability to insert a cannulated screw with a larger wall thickness (cannulation of a smaller diameter) with strength that is closer to the strength of a solid screw than a cannulated screw with a bigger cannulation diameter.

The lag screw 1300 disclosed herein can be used in other applications. For example, as shown in FIG. 16, a plurality of the lag screws 1330, which can be delivered using the instruments disclosed herein, such as the guide wire 400, can be used in combination with an intramedullary nail for fracture. The intramedullary nail 1400 can be threaded and can include a first section with a first major diameter and a second section with a second major diameter. There can be a transition portion between the first and second sections. The transition portion can have a major diameter that changes from the first major diameter to the second major diameter. Additional details of the intramedullary nail 1600 are described in International Patent Publication No. 2019/050833, published on Mar. 14, 2019, the entirety of which is incorporated herein by reference. The combination of the lag screw(s) 1300 and the intramedullary nail 1400 can be used for fixation in more complex fracture cases. As shown in FIGS. 17A-17B, the instruments and deliver method disclosed herein can deliver the lag screws for fracture fixation not only in the hand as shown above, but also in the metatarsal (FIG. 17A) and phalanx (FIG. 17B) of a foot.

Example Alternative Delivery Tools to a Stepped Guide Wire

Alternative to the stepped guide wire in FIGS. 4A-4C and 29A-32B and methods of using the guide wire disclosed herein, additional tools and methods for introducing a cannulated implant (for example, the cannulated implant 100, 2600, 2600C, 2600D, 2600E, 2600F, the lag screw 1300, the intramedullary nail as described in International Patent Publication No. 2019/050833, or otherwise), a partially cannulated implant, or a non-cannulated implant will be described with reference to FIGS. 18-25B. The alternative examples described below are not limiting. Features of any one of the various examples described below can be combined or incorporated into features of another one of these examples.

The stepped guide wire in FIGS. 4A-4C and 29A-32B and the alternative examples described below with reference to FIGS. 18-25B may be used to deliver any threaded (any helical thread regardless of the pitch size) or partially threaded implants, such as example orthopedic implant 100 and the lag screws 1300 disclosed herein, and/or any other elongate implants that may not necessarily include a thread, but may include one or more protrusions on a shaft of the implant. If the implant is fully or partially threaded, the thread can have any pitch size. The one or more protrusions can include barb(s), fin(s), ridge(s), and/or the like. The one or more protrusion can have any shape or size. The partially or fully threaded implant can be driven into the bone by rotation. The non-threaded implant can be driven into the bone by impaction.

Figure 18A:
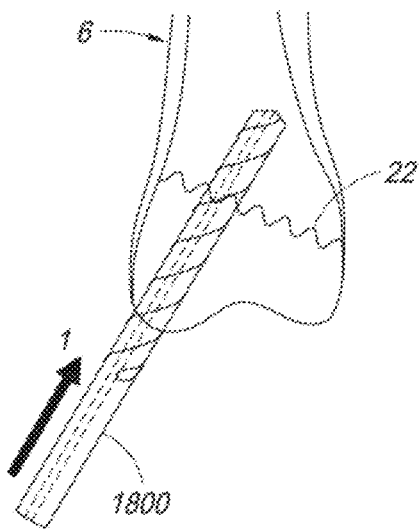
FIGS. 18A-25B illustrate schematically various example alternative delivery tools to a stepped guide wire for delivering the implants disclosed herein.
Figure 18B:
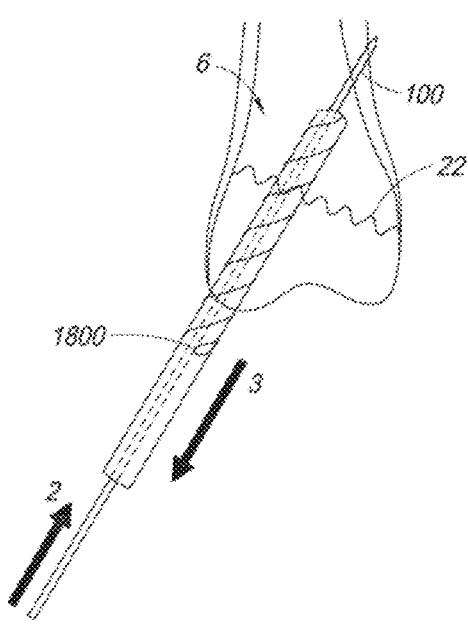

FIGS. 18A-18B illustrate steps of using a cannulated drill 1800 to deliver a cannulated implant. All the drills illustrated in FIGS. 18-25B can include a guide wire with a greater outer diameter (for example, substantially similar to a minor diameter to a shaft of an implant to be used for fracture fixation) than a conventional K-wire. As shown in FIG. 18A, in a first step, the cannulated drill 1800 can be inserted into a bone 6 across a fracture line 22 in the direction shown by arrow 1. The insertion of the cannulated drill 1800 can provide an implant pathway in the bone 6. As shown in FIG. 18B, in a second step, a K-wire 1810 with a smaller outer diameter can be inserted into a cannulation of the cannulated drill 1800 in the direction shown by arrow 2. In a third step, the cannulated drill 1800 can be removed along the direction shown by arrow 3, with the K-wire 1810 remaining in the implant pathway to maintain fracture reduction and provide guidance for implanting a cannulated implant over the K-wire 1810.

Figure 19:
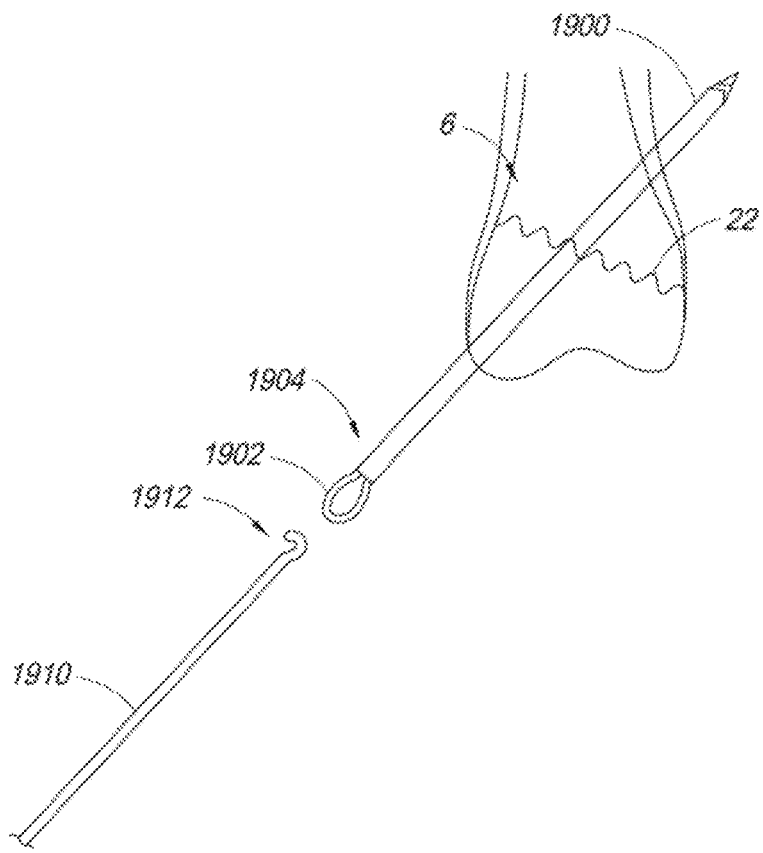

FIG. 19 illustrates a drill or guide wire 1900 including a wire loop 1902 attached to a trailing end 1904 (opposite a drilling tip end, which can including a trocar or any other sharp tip) of the drill 1900. The drill 1900 can be non-cannulated or substantially non-cannulated. The drill 1900 can be inserted into a bone 6 across a fracture line 22 to provide an implant pathway in the bone 6. A corresponding K-wire 1910 with a smaller outer diameter than the drill 1900 can include a hook 1912. The hook 1912 can engage the wire loop 1902 so that when the drill 1900 is pulled through the implant pathway on a far side of the bone 6, the K-wire 1910 can be pulled into the bone 6 following the drill 1900 and through the implant pathway. After the drill 1900 is removed, the K-wire 1910 can remain in the implant pathway to maintain fracture reduction and provide guidance for implanting a cannulated implant over the K-wire 1910. The drill 1900 can be disengaged from the K-wire 1910 by removing the hook 1912 from the wire loop 1902. The configuration shown in FIG. 19 can be reversed so that the hook can be on the trailing end 1904 of the drill 1900 and the loop can be on the K-wire 1910. Optionally, the connection point between the hook and the loop can be crimped to reduce likelihood of disconnection between the hook and the loop as the drill 1900 is pulled through the bone 6.

Figure 20:
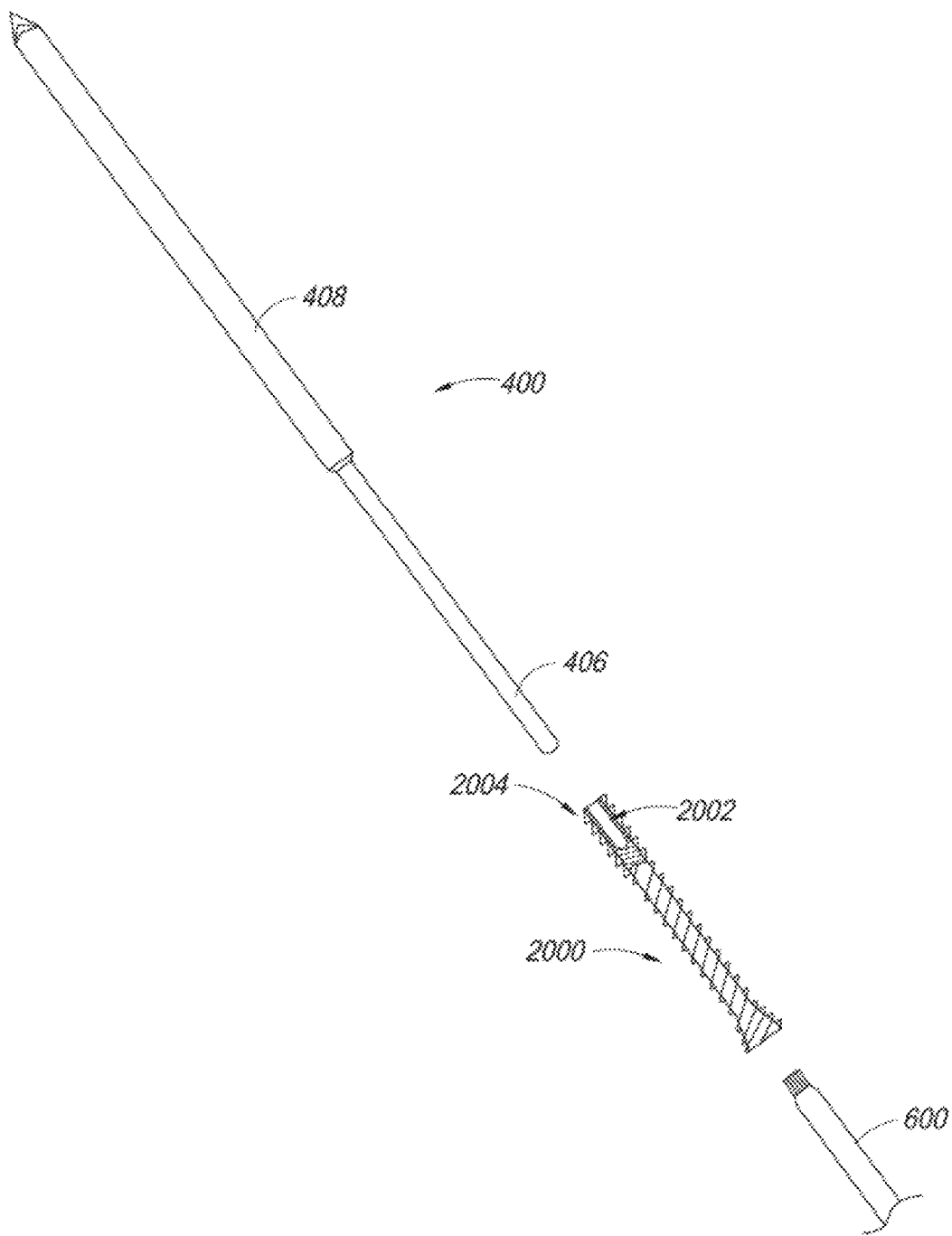

As shown in FIG. 20, a guide wire 400 similar or substantially the same as the guide wire 400 described above can be used for delivering an implant 2000 that includes a blind hole 2002 (rather than a through-cannulation) at its leading end 2004. In other words, the implant 2000 may have any of the features of the implant 100 or the lag screw 1300 except that the implant 2000 is not fully cannulated. The blind hole 2002 can be sized to slidably receive the thinner first portion 406 of the guide wire 400. The implant 2000 can engage the thinner first portion 406 of the guide wire 400 after the thicker second portion 408 has been inserted into a bone or bone fragment and has prepared an implant pathway in the bone or bone fragment. After the implant 2000 engages the guide wire 400 at the blind hole 2002, the driver 600 disclosed herein or any other suitable driver (for example, a non-cannulated driver) can be used to insert the implant 2000 into the bone for fracture fixation.

Figure 21A:
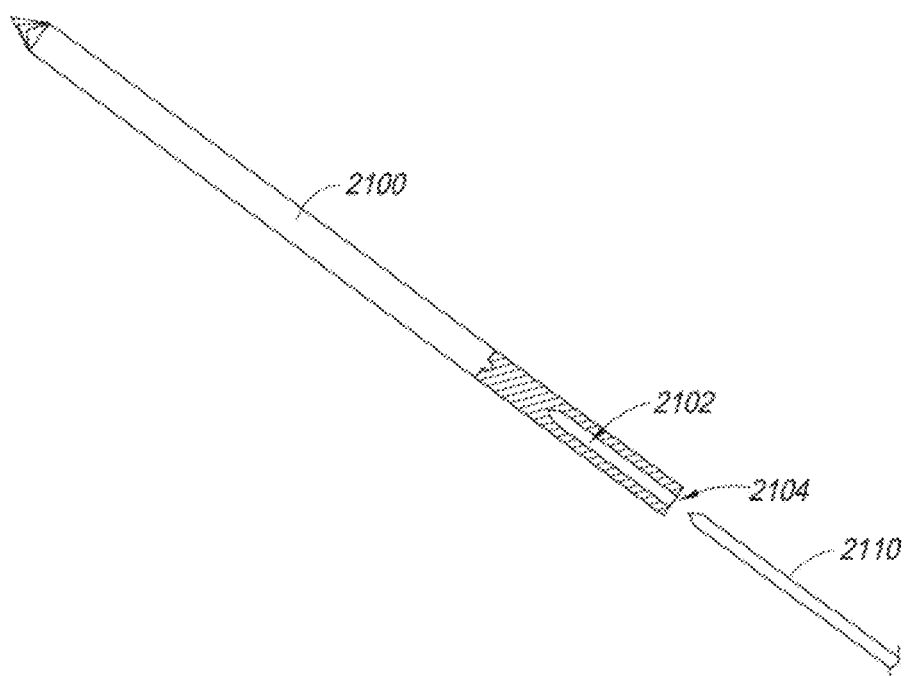
Figure 21B:
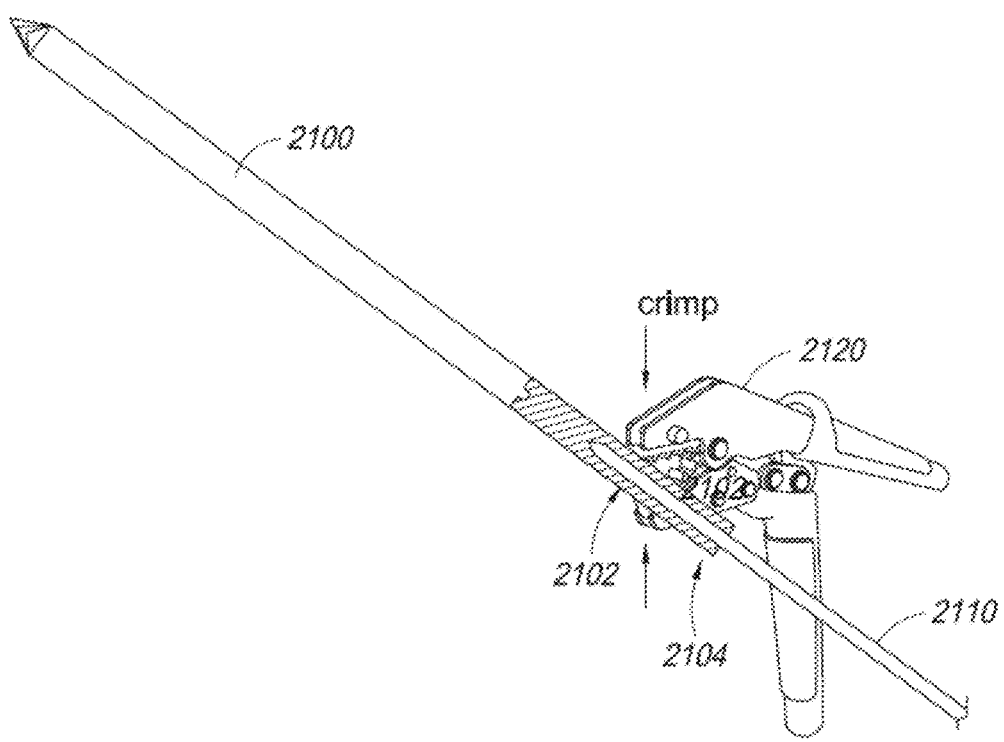

The thicker second portion and thinner first portion of the guide wire disclosed herein can be removably connected for delivering a cannulated implant during fracture fixation. FIGS. 21A and 21B illustrate a partially cannulated drill 2100 including a blind hole 2102 at its trailing end 2104. The outer diameter of the drill 2100 can be substantially the same as the outer diameter of the second portion 408 of the guide wire 400 described above. The blind hole 2102 can receive a K-wire 2110 with a smaller diameter (for example, any conventional, off-the-shelf K-wire with an outer diameter smaller than about 0.7 mm). When the drill 2100 is inserted into a bone to prepare an implant away and pulled through the implant pathway on a far side of the bone, the K-wire 2110 can be pulled into the bone and through the implant pathway. After the drill 2100 is pulled through the bone, the K-wire 2110 can remain in the implant pathway to maintain fracture reduction and provide guidance for implanting a cannulated implant (screw, nail, or otherwise) over the K-wire 2110. As shown in FIG. 21B, to improve the strength of connection between the blind hole 2102 of the drill 2100 and the K-wire 2110, a needle driver 2120 or any other suitable tool can optionally crimp the drill 2100 at the blind hole 2102 and the K-wire 2110 together before pulling the drill 2100 through the bone.

Figure 22B:
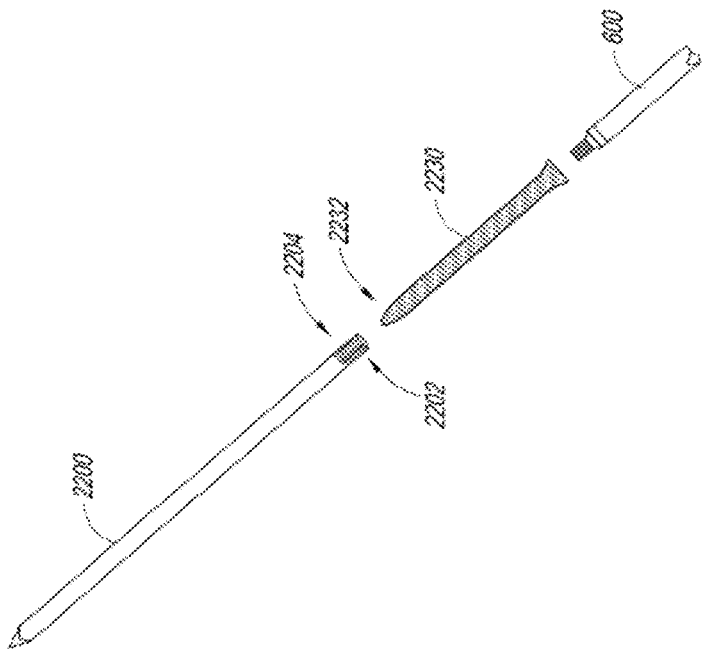
Figure 22A:
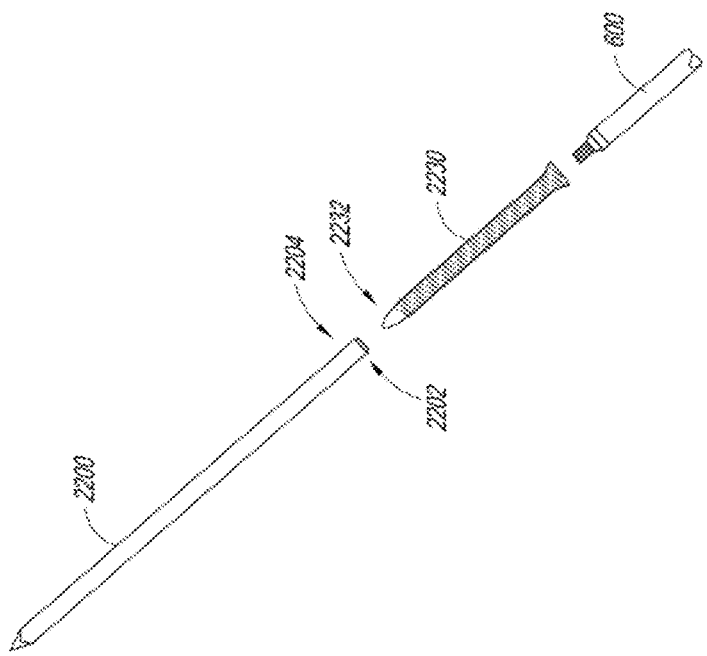

As shown in FIG. 22A, instead of a blind hole, a drill 2200 can include a female recess 2202 at its trailing end 2204. The implant 2230 (screw, nail, or otherwise) can have a mating male part 2232 at its leading end to nest into the female recess 2202. The implant 2230 may not be cannulated. The outer diameter of the drill 2200 can be substantially the same as a minor or root diameter of the implant 2230. When the drill 2200 is pulled through the implant pathway on a far side of the bone, the implant 2230 can be pushed along, for example, using the driver 600 or any other driver, with the drill 2200 as the male part 2232 remains nested in the female recess 2202. After the drill 2100 is pulled through the bone, the implant 2230 can remain in the implant pathway to maintain fracture reduction and provide fixation of a fractured bone. As shown in FIG. 22B, the female recess 2202 can be internally threaded and the mating male part 2232 can include a corresponding external thread to improve coupling strength between the implant 2230 and the drill 2200 as the implant 2230 is inserted along with the drill 2200 into a bone or bone fragment. After implantation of the implant 2230, the drill 2200 can be unscrewed from the implant 2230 and removed.

Figure 22C:
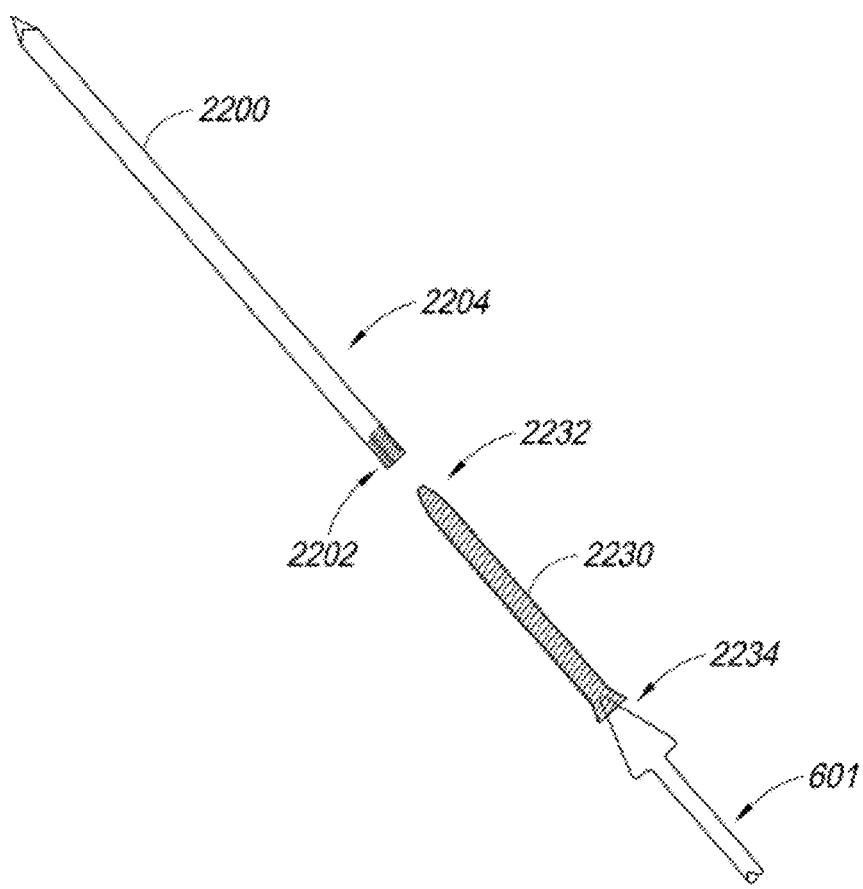

As shown in FIG. 22C, rather than using a hex/hexalobe driver 600 to drive the implant 2230 as shown in FIGS. 22A-22B, the head of the implant 2230 can alternatively be manufactured with a break-away or snap-off connection 2234 that can be driven by a wire driver 601. The snap-off feature 2234 can break away from the wire driver 601 at a specific torque or by bending the wire driver 601 back and forth. The wire driver 601 can be broken off from the implant 2230 after the implant 2230 is inserted into a desired location in the bone or bone fragment using the drill 2200.

Figure 23:
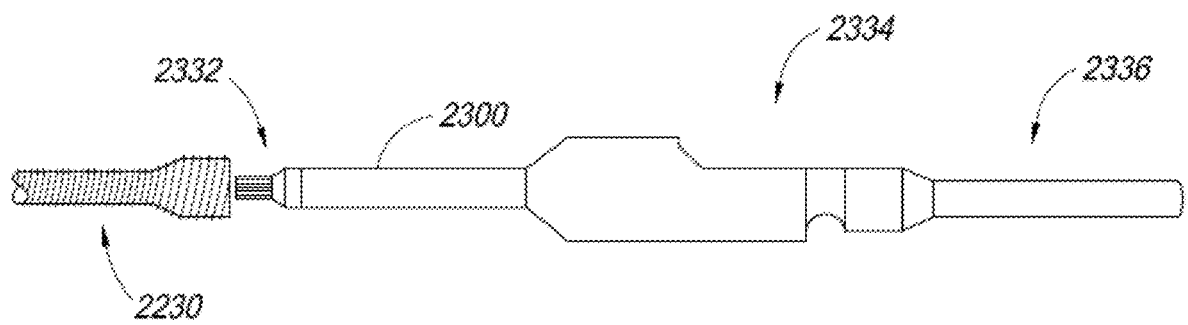

As shown in FIG. 23, when using the drill or guide wire 2200 in FIGS. 22A-22B to deliver the implant 2300, the hex driver 2300 may optionally include an AO (Association for Osteosynthesis) feature 2334 and/or a smaller diameter wire driver portion on its trailing end (opposite the hex or hexalobe driver interface end 2332). The AO feature 2334 can allow for powered insertion using a wire driver 2336 or another power source with an AO quick-connect feature. Alternatively, the driver 2300 can be used by hand without any power.

Figure 24:
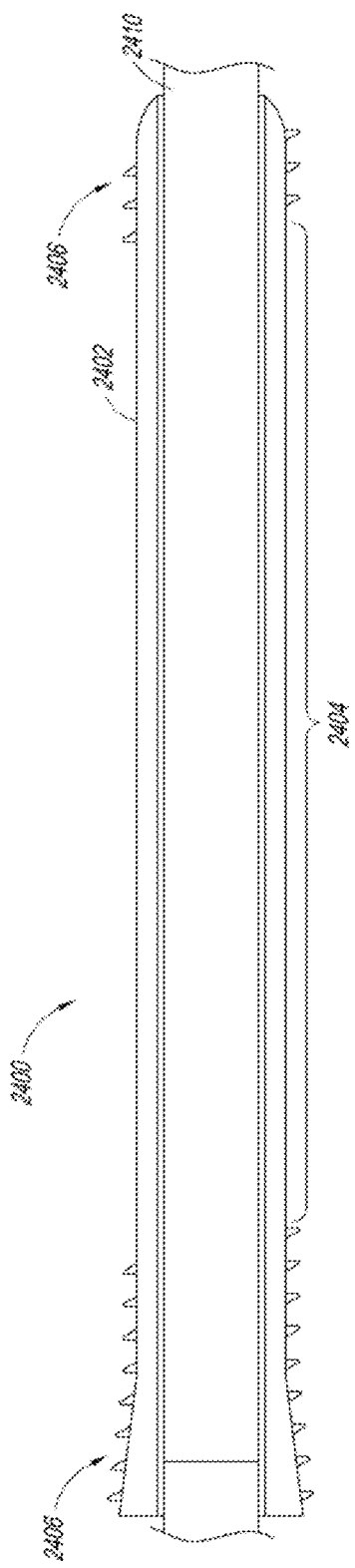

As shown in FIG. 24, a solid guide wire 2410 with an outer diameter (for example, about 1.0 mm) that is larger than a conventional K-wire can be used as an alternative to using a stepped guidewire. One way to use a slightly larger guide wire, which requires a larger cannulation diameter of the implant, is to increase the outer minor diameter (root) of the implant to maintain the desired implant strength. However, if one wants to keep the same overall outer profile (that is, the same outer diameter) of the implant, the thread depth on the implant would need to be decreased. To address the issue of reduced thread depth, as shown in FIG. 24, an implant 2400 can eliminate threads along a middle portion 2404 of the shaft 2402 (for example, for about 80% of the length of the shaft). The outer diameter of the unthreaded middle portion 2402 can be the same as the major diameter of the threaded portion(s) of the shaft of the implant. The implant 2400 can act as a strong tube or strut, while having threads 2406 at the leading and trailing ends to provide bone engagement. Although the implant 2400 may have a thinner wall thickness, the implant 2400 can be of similar strength as the implant 100 due to the greater amount of material in the non-threaded middle portion 2404 than if the middle portion were threaded.

Figure 25A:
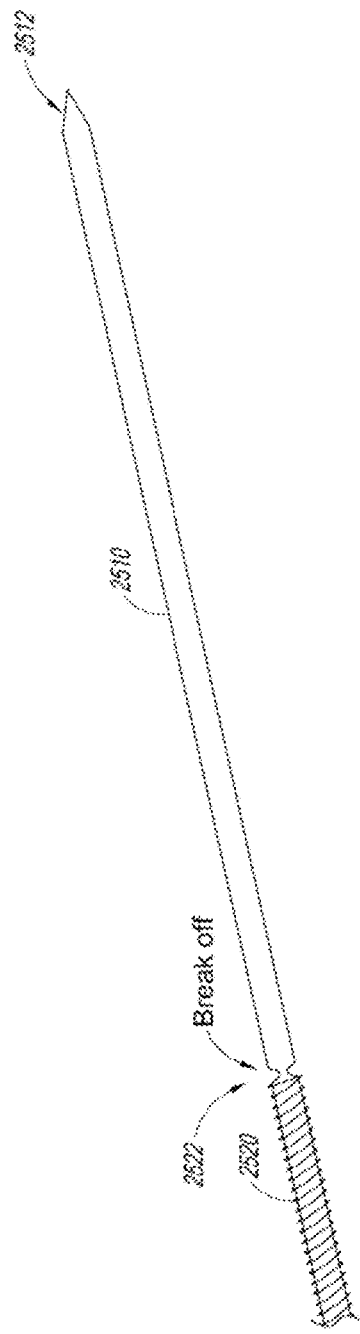
Figure 25B:
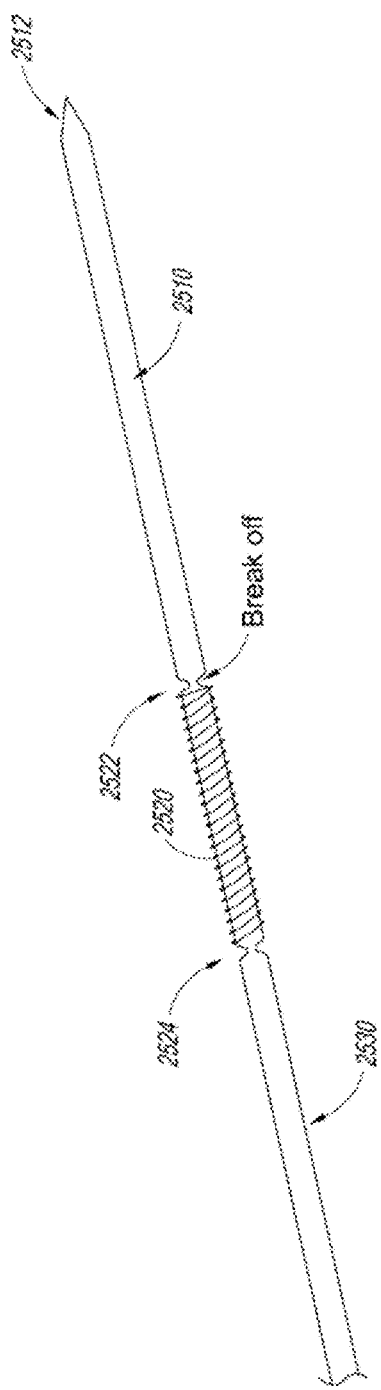

As shown in FIGS. 25A and 25B, a guide wire 2510 with an outer diameter that is larger than a conventional K-wire can be connected (for example, rigidly connected) to a leading end 2522 of an implant 2520. The outer diameter of the guide wire 2510 can be substantially the same as the minor diameter of the implant 2520. The connection between the guide wire 2510 and the implant 2520 can allow for axial movement of the guide wire 2510 and the implant 2520 as a single component. The implant 2520 can be any of the implant or screw examples disclosed herein, or any other implant configured to be inserted into a bone and/or bone fragments. The guide wire 2510 can be non-cannulated. The leading end 2512 of the guide wire 2510 can include a sharp tip. When in use, the leading end 2512 of the guide wire 2510 can facilitate reaming of a bone tunnel through the bone or bone fragment, with the implant 2520 connected to the guide wire 2510. Once the implant 2520 has been inserted to a desired location, for example, via confirmation using radiography, the guide wire 2510 can be broken off at the leading end 2522 of the implant 2520. The interface between the leading end 2522 of the implant 2520 and the guide wire 2510 can include a thinned section to allow ease of breaking away of the guide wire 2520 at the thinned section. Accordingly, the combination of the guide wire 2510 and the implant 2520 can eliminate the pre-drilling step and the need for a separate reamer (or drill) for inserting the implant 2520 into the bone or bone fragment.

As shown in FIG. 25B, in addition to the leading guide wire 2510, a trailing guide wire 2530 can be connected (for example, rigidly connected) to a trailing end 2524 of the implant 2520. The connection between the trailing guide wire 2530 and the implant 2520 can allow an axial force imparted onto the trailing guide wire 2530 to be transmitted axially along the implant 2520 and the leading guide wire 2510. The guide wire 2530 can have an outer diameter that is larger than a conventional K-wire, for example, having an outer diameter that is substantially the same as the minor diameter of the implant 2520. During insertion of the implant 2520 and the leading guide wire 2510 into the bone or bone fragment, the trailing guide wire 2530 can act as a driver. Once the implant 2520 has been inserted to a desired location, the guidewire 2530 can be broken off at the trailing end 2524 of the implant 2520. The interface between the trailing end 2524 of the implant 2520 and the trailing guide wire 2530 can include a thinned section to allow ease of breaking away of the trailing guide wire 2530 at the thinned section. The addition of the trailing guide wire 2530 to the combination of the implant 2520 and the leading guide wire 2510 can further eliminate the need for a separate driver. The combination of the implant 2520 and the leading guide wire 2510, and/or the combination of the implant 2520, the leading guide wire 2510, and the trailing guide wire 2530, can be made available in different sizes. The different sizes can accommodate different outer diameters of the implant 2520.

Terminology

Although this disclosure has been described in the context of certain embodiments and examples, it will be understood by those skilled in the art that the disclosure extends beyond the specifically disclosed embodiments to other alternative embodiments and/or uses and obvious modifications and equivalents thereof. In addition, while several variations of the embodiments of the disclosure have been shown and described in detail, other modifications, which are within the scope of this disclosure, will be readily apparent to those of skill in the art. It is also contemplated that various combinations or sub-combinations of the specific features and aspects of the embodiments may be made and still fall within the scope of the disclosure. For example, features described above in connection with one embodiment can be used with a different embodiment described herein and the combination still fall within the scope of the disclosure. It should be understood that various features and aspects of the disclosed embodiments can be combined with, or substituted for, one another in order to form varying modes of the embodiments of the disclosure. Thus, it is intended that the scope of the disclosure herein should not be limited by the particular embodiments described above. Accordingly, unless otherwise stated, or unless clearly incompatible, each embodiment of this invention may comprise, additional to its essential features described herein, one or more features as described herein from each other embodiment of the invention disclosed herein.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a sub combination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

What is claimed is:

1. A guide wire having at least two diameters and configured to deliver a cannulated orthopedic implant, the guide wire comprising:
   a first portion having a first generally uniform outer diameter; and
   a second portion, the second portion including at least a first segment and a second segment, the first segment having a second generally uniform outer diameter that is greater than the first generally uniform outer diameter, the second segment having a third outer diameter that is smaller than the second generally uniform outer diameter,
   wherein the first segment is disposed between the second segment and the first portion,
   wherein the cannulated orthopedic implant is configured to be slidably mounted onto the first portion of the guide wire, the second generally uniform outer diameter being substantially the same as a minor or root diameter of the cannulated orthopedic implant,
   wherein the guide wire comprises a first free end and a second free end opposite the first free end,
   wherein the first portion includes the first free end of the guide wire.

2. The guide wire of claim 1, wherein a free end of the second portion comprises a sharp tip, wherein the second free end is the free end of the second portion.

3. The guide wire of claim 1, wherein the first generally uniform outer diameter is between 0.7 mm to 0.9 mm, and the second generally uniform outer diameter is between 1.5 mm to 2.0 mm.

4. The guide wire of claim 1, wherein the first and second segments are separated by a third segment, an outer diameter of the third segment transitioning from the third outer diameter to the second outer diameter.

5. The guide wire of claim 1, wherein the first and second portions are removably connected.

6. The guide wire of claim 5, wherein the second portion comprises a cannulation configured to receive the first portion.

7. The guide wire of claim 6, wherein the cannulation extends along an entire length or a partial length of the second portion.

8. The guide wire of claim 5, wherein one of the first or second portions includes a hook and the other one of the first or second portions includes a loop.

9. A method of delivering an elongate threaded orthopedic implant into a bone, the implant being at least partially cannulated, the method comprising:
   using the second portion of the guide wire of claim 1, preparing a pathway in the bone, the pathway having a diameter substantially the same as the root or minor diameter of the elongate threaded orthopedic implant;
   inserting the first portion of the guide wire into a cannulation of the implant; and
   driving the implant through the pathway guided by the first portion of the guide wire.

10. A method of intramedullary fracture fixation, the method comprising:
    delivering a guide wire having at least two diameters across fractured portions of a fractured bone, the guide wire comprising a first, trailing portion having a first diameter and a second, leading portion including at least a first segment and a second segment, the first segment having a second diameter greater than the first diameter, the second segment having a third outer diameter that is smaller than the second diameter, wherein the first segment is disposed between the second segment and the first portion, wherein the guide wire comprises a first free end and a second free end opposite the first free end, wherein the first portion includes the first free end of the guide wire, wherein the delivering comprises extending the second portion of the guide wire across a medullary canal of the bone until a leading tip of the guide wire is substantially flush with an outer surface of the bone;
    selecting a cannulated elongate implant by determining a length of the cannulated elongate implant based on a position of the guide wire in the bone;
    slidably mounting the cannulated elongate implant onto the first portion of the guide wire;
    inserting the cannulated elongate implant into the bone guided by the guide wire, wherein ends of the cannulated elongate implant do not protrude from the outer surface of the bone; and
    removing the guide wire from the bone.

11. A method of intramedullary fracture fixation, the method comprising:
    delivering a first guide wire having at least two diameters across fractured portions of a fractured bone, the first guide wire comprising a first, trailing portion having a first diameter and a second, leading portion having a second diameter greater than the first diameter, wherein the delivering comprises extending the second portion of the first guide wire across a medullary canal of the bone until a leading tip of the first guide wire is substantially flush with an outer surface of the bone;

selecting a first cannulated elongate implant by determining a length of the first cannulated elongate implant based on a position of the first guide wire in the bone;

slidably mounting the first cannulated elongate implant onto the first portion of the first guide wire;

inserting the first cannulated elongate implant into the bone guided by the first guide wire;

removing the first guide wire from the bone;

delivering a second guide wire having at least two diameters across fractured portions of a fracture bone, the second guide wire comprising a first, trailing portion having the first diameter and a second, leading portion having the second diameter greater than the first diameter, wherein the delivering comprises extending the second portion of the second guide wire across the medullary canal of the bone until a leading tip of the second guide wire is substantially flush with the outer surface of the bone;

selecting a second cannulated elongate implant by determining a length of the second cannulated elongate implant based on a position of the second guide wire in the bone;

slidably mounting the second cannulated elongate implant onto the first portion of the second guide wire;

inserting the second cannulated elongate implant into the bone guided by the second guide wire; and removing the second guide wire from the bone, wherein a root diameter surface of the first implant is in contact with a root diameter surface of the second implant, and wherein delivering the second guide wire is performed after removing the first guide wire from the bone.

12. The method of claim 11, wherein each of the first and second implants are bi-cortical.

13. The method of claim 11, wherein each of the first and second implants terminates at or prior to the outer surface of the bone.

14. The method of claim 11, wherein ends of each of the first and second implants do not protrude into tissue surrounding the bone.

15. The method of claim 11, wherein delivering the second guide wire is performed after delivering the first guide wire and before inserting the first implant.

16. The method of claim 11, wherein the delivering comprises extending the second portion of the second guide wire across the medullary canal of the bone in a cross pattern with the tunnel in the bone created by the second portion of the first guide wire.

17. The method of claim 11, wherein the delivering comprises extending the second portion of the second guide wire across the medullary canal of the bone to be substantially parallel with the tunnel in the bone created by the second portion of the first guide wire.

18. The method of claim 11, wherein the first and/or second cannulated elongate implants include a thread, the thread in a middle portion having a greater pitch than the thread at or around a driver head or the leading tip.

19. The method of claim 11, wherein a major outer diameter of the first and/or second cannulated elongate implants is smaller in the middle portion than at or around the driver head or the leading tip.

* * * * *